(12) United States Patent
Garovoy et al.

(10) Patent No.: US 10,793,893 B2
(45) Date of Patent: Oct. 6, 2020

(54) METHODS OF ADMINISTERING 3,4-DIAMINOPYRIDINE

(75) Inventors: Marvin R. Garovoy, San Anselmo, CA (US); Peter E. Haroldsen, Pacifica, CA (US); Donald G. Musson, Greenbrae, CA (US)

(73) Assignee: SERB SA, Brussels (BE)

( * ) Notice: Subject to any disclaimer, the term of this patent is extended or adjusted under 35 U.S.C. 154(b) by 647 days.

(21) Appl. No.: 14/128,672

(22) PCT Filed: Jun. 29, 2012

(86) PCT No.: PCT/US2012/044904
§ 371 (c)(1),
(2), (4) Date: May 7, 2014

(87) PCT Pub. No.: WO2013/003708
PCT Pub. Date: Jan. 3, 2013

(65) Prior Publication Data
US 2014/0255380 A1 Sep. 11, 2014

Related U.S. Application Data

(60) Provisional application No. 61/553,045, filed on Oct. 28, 2011, provisional application No. 61/503,553, filed on Jun. 30, 2011.

(51) Int. Cl.
*C12Q 1/48* (2006.01)
*A61K 31/44* (2006.01)
*A61K 38/45* (2006.01)
*C12Q 1/6883* (2018.01)
*G01N 33/564* (2006.01)

(52) U.S. Cl.
CPC ............ *C12Q 1/48* (2013.01); *A61K 31/44* (2013.01); *A61K 38/45* (2013.01); *C12Q 1/6883* (2013.01); *G01N 33/564* (2013.01)

(58) Field of Classification Search
None
See application file for complete search history.

(56) References Cited

U.S. PATENT DOCUMENTS

| | | |
|---|---|---|
| 3,896,083 A | 7/1975 | Gerber |
| 3,943,125 A | 3/1976 | Gerber |
| 4,079,039 A | 3/1978 | Gerber |
| 4,386,095 A | 5/1983 | Gibson et al. |
| 5,540,938 A | 7/1996 | Masterson et al. |
| 5,939,553 A | 8/1999 | Reichwein et al. |
| 2004/0106651 A1 | 6/2004 | Guyon et al. |
| 2009/0181094 A1 | 7/2009 | Sheu |
| 2011/0052675 A1 | 3/2011 | Sheu |

FOREIGN PATENT DOCUMENTS

| | | |
|---|---|---|
| EP | 0484186 B1 | 12/1999 |
| EP | 1732548 B1 | 6/2011 |
| WO | WO-8401160 A1 | 3/1984 |
| WO | WO-8401161 A1 | 3/1984 |
| WO | WO-8401162 A1 | 3/1984 |
| WO | WO-8504178 A1 | 9/1985 |
| WO | WO-8700844 A1 | 2/1987 |
| WO | WO-0047210 A1 | 8/2000 |
| WO | WO-02072025 A2 | 9/2002 |
| WO | WO-2004082684 A1 | 9/2004 |
| WO | WO-2009018502 A2 | 2/2009 |
| WO | WO-2009018504 A1 | 2/2009 |
| WO | WO-2011019845 A1 | 2/2011 |
| WO | WO-2012103471 A1 | 8/2012 |

OTHER PUBLICATIONS

Ma (Biomedical and Environmental Sciences, 2004, 17:291-298).*
Mcdonagh (Pharmacogenetic Genomics, 2014, 24(8): 409-415).*
Erichsen et al. (Br J. Cancer, 2004, vol. 90, pp. 747-751).*
Ionnidis (Plost Med, 2005, 2(8):e124).*
Hirschhorn et al. (Genetics in Medicine, 2002, 4(2): 45-61).*
Osborne et al. Biochemical Genetics, 2003, vol. 41, No. 11/12, pp. 405-411.*
DbSNP rs1041983 (available at ncbi.nlm.nih.gov, ss342253601, pp. 1-2, printed Jan. 24, 2020).*
DbSNP rs 1801280 (available at ncbi.nlm.nih.gov, ss342253602, pp. 1-2, printed Jan. 24, 2020).*
Molgo, J., et al: "3,4-Diaminopyridine, an Arphan Drug, in the Symptomatic Treatment of Lambert-Eaton Myasthenic Syndrome", Pfluegers Arch: European Journal of Physiology, Springer-Verlag, Berlin, DE, vol. 431, No. 6, Suppl. 02, Sep. 23, 1995 (Sep. 23, 1995), XP001030624, ISSN: 0031-6768, DOI: 10.1007/BF02346385.
Bever, C. T. Jr., et al: "Preliminary Trial of 3,4-Diaminopyridine in Patients With Multiple Sclerosis", Annals of Neurology, John Wiley and Sons, Boston, US, vol. 27, No. 4, Jan. 1, 1990 (Jan. 1, 1990), pp. 421-427, XP009163039, ISSN: 0364-5134, DOI: 10.1002/ANN. 410270411.
Wirtz, Paul W., et al: "3,4-Diaminopyridine for the Treatment of Lambert-Eaton Myasthenic Syndrome", Expert Review of Clinical Immunology, England, vol. 6, No. 6, Nov. 1, 2010 (Nov. 1, 2010), pp. 867-874, XP009163036, ISSN: 1744-8409.
Komai, Kiyonobu, et al: "Pharmacokinetics and Tissue Distribution of 3,4-Diaminopyridine", Neurology, Lippincott Williams & Wilkins, Philadelphia, US, vol. 9, no. Suppl. 4, Mar. 1, 2011 (Mar. 1, 2011), p. A282, XP009163033, ISSN: 0028-3878.
Haroldsen, Peter et al: "Genetic Regulation of Amifampridine Phosphate (Firdapse (R)) Metabolism Produces Significant Differences in Pharmacokinetics and Side Effects", Neurology, Lippincott Williams & Wilkins, Philadelphia, US, vol. 78. No, Suppl. 1, Apr. 1, 2012 (Apr. 1, 2012), p. P04095, XP009163034, ISSN: 0028-3878.

(Continued)

*Primary Examiner* — Sarae L Bausch
(74) *Attorney, Agent, or Firm* — Sterne, Kessler, Goldstein & Fox P.L.L.C.

(57) ABSTRACT

Provided herein are methods of determining NAT acetylation status of a subject with a 3,4-DAP-sensitive disease, methods of selecting a dose of 3,4-DAP or a pharmaceutically acceptable salt thereof adjusted to a subject's acetylation status, methods of administering 3,4-diaminopyridine or a pharmaceutically acceptable salt thereof to a patient in need thereof, and methods of treating 3,4-DAP sensitive diseases.

15 Claims, 37 Drawing Sheets

(56) References Cited

OTHER PUBLICATIONS

Murray, N. M. et al., "Treatment with oral 4-aminopyrideine in disorders of neuromuscular transmission", Neurology (Ny) Mar. 1981, 31, 265-27.

McEvoy, K. M. et al., "3,4-Diaminopyridine in the Treatment of Lambert-Eaton Myasthenic Syndrome", N Engl. J. Med. 1989, vol. 321, No. 23, pp. 1567-1571.

International Search Report, International Application No. PCT/US2012/044904, International Filing Date Jun. 29, 2012.

Sheean, et al., "An open-labelled clinical and electrophysiological study of 3,4 diaminopyridine in the treatment of fatigue in multiple sclerosis", Brain 1998, 121, pp. 967-975.

Wirtz et al., "Efficacy of 3,4-Diaminopyridine and Pyridostigmine in the Treatment of Lambert-Eaton Myasthenic Syndrome: A Randomized, Double-Blind, Placebo-Controlled, Crossover Study", Nature publishing group, 2009, 86(1), pp. 44-48.

Bever, et al., "Treatment with oral 3,4 diaminopyridine improves leg strength in multiple sclerosis patients: Results of a randomized, double-blind, placebo-controlled, crossover trial", Neurology, American Academy of Neurology, 1996, 47, pp. 1457-1462.

Rothen, et al, "Acetaminophen is an inhibitor of hepatic N-acetyltransferase 2 in vitro and in vivo", Lippincott Williams & Wilkins, Pharmacogenetics 1998, 8:553-559.

Written Opinion, International Application No. PCT/US2012/044904, International Filing Date Jun. 29, 2012, 7 pages.

Bolt, et al., "Re-investigation of the concordance of human NAT2 phenotypes and genotypes", Archives of Toxicology 2005, 79(4), 196-200.

Rowland and Tozer, Clinical Pharmacokinetics, Concepts and Applications, 3rd Edition, 20 1995,Absorption Ch 9, Lippincott Williams and Wilkins Publishers, pp. 119-136.

Hiratsuka, et al., "Genotyping of the N-acetyl transferase 2 polymorphism in the prediction of adverse drug reactions to Isoniazid in Japanese patients", Drug Metabol. Pharmacokin, 17 (4): pp. 357-362 (2002).

Rychlik-Sych, et. al., "Acetylation genotype and phenotype in patients with systemic lupus erythematosus", Pharmacological Reports, ISSN 1734-1140, 2006, 58, pp. 2-29.

Casarett & Doull's, 30 Toxicology, The Basic Science of Poisons 7th Ed. (2008) Chapter 6: Biotransformation of Xenobiotics. pp. 161-304.

Cascorbi, et al., "Arylamine N-acetyltransferase (NAT2) Mutations and Their Allelic Linkage in Unrelated Caucasian Individuals: Correlation with Phenotypic Activity", Am. J. Hum. Genet., 57:581-592, 1995.

Jetter, et al., "Phenotyping of N-acetyltransferase type 2 and xanthine oxidase with caffeine: when should urine samples be collected?" Eur J Pharmacol (2009) 65: pp. 411-417, DOI 10.1007/s00228-008-0597-0.

Jetter, et al., "Phenotyping of N -acetyltransferase type 2 by caffeine from uncontrolled dietary exposure", Eur J Clin Pharmacol 2004, 60: pp. 17-21, DOI 10.1007/s00228-003-0718-8.

Eidus, et. al., "Simplification of isoniazid phenotyping procedure to promote its application in the chemotherapy of tuberculosis*", Bull Org. mond. Sante, Bull. World Health Organ., 1973, 49, pp. 507-516.

Welfare, et al., "The effect of NAT2 genotype and gender on the metabolism of caffeine in nonsmoking subjects", Blackwell Science Ltd., Br J Clin Pharmacol., 2000, 49(3), 240-243.

Schneider, et. al., "Extractionless method for the determination of urinary caffeine metabolites using high-performance liquid chromatography coupled with tandem mass spectrometry", J. Chromatog. B, 2003, 789, 227-237.

Lin, et. al., "Ethnic distribution of slow acetylator mutations in the polymorephic N-acetyltransferase (NAT2) gene", Pharmacogenetics 1994, 4, pp. 125-134.

Cascorbi I, Drakoulis N, Brockmoller J, Maurer A, Sperling K, Roots 1(1995) Arylamine N-acetyltransferase (NAT2) mutations and their allelic linkage in unrelated caucasian individuals: correlation with phenotypic activity, Am J Hum Genet 57:581-592.

McDonagh EM, et. al. "PharmGKB Summary: very important pharmacogene information on N-acetyltransferase 2." Pharmacogenet Genomics 2014 24(8) p. 409-425 (doi:10.1097/FPC.0000000000000062).

Agundez, J.A.G., et al., "Slow allotypic variants of the NAT2 gene and susceptibility to early-onset Parkinson's disease," Neurology, 51(6):1587-1592, Lippincott Williams & Wilkins, United States (Dec. 1998).

Benziane, H., et al., "[Formulation and stability of hospital preparation of 3,4-diaminopyridine capsules]," Annales Pharmaceutiques Francaises, 61(6): Abstract, Elsevier, France (2003).

Bever, C.T, "The current status of studies of aminopyridines in patients with multiple sclerosis," Annals of Neurology, 36(S1):S118-S121, John Wiley & Sons, United States (1994).

Borlak, J. and Reamon-Buettner, S.M., "N-acetyltransferase 2 (NAT2) gene polymorphisms in Parkinson's disease," BMC Medical Genetics, 7:30, pp. 1-9, BioMed Central, England (2006).

Donnelly, R.F, "Chemical Stability of 4-Aminopyridine Capsules," The Canadian Journal of Hospital Pharmacy, 57:283-287, The Canadian Society of Hospital Pharmacists, Ontario (2004).

Gibaud, S., et al., "Preparation of 3,4-diaminopyridine microparticles by solvent-evaporation methods," International Journal of Pharmaceutics, 242(1-2):197-201, Elsevier/North-Holland Biomedical Press, Netherlands, (2002).

Kaes, C., et al., "Bipyridine: the Most Widely Used Ligand. A Review of Molecules Comprising at Least Two 2,2'-bipyridine Units," Chemical Reviews, 100(10):3553-3590, American Chemical Society, United States, (2000).

Maerker, G. and Case, F.H, "The Synthesis of Some 4,4'-Disubstituted 2,2'-Bipyridines," Journal of the American Chemical Society, 80(11):2745-2748, American Chemical Society, United States(1958).

Raust, J.A., et al., "Stability studies of ionised and non-ionised 3,4-diaminopyridine: Hypothesis of degradation pathways and chemical structure of degradation products," Journal of Pharmaceutical and Biomedical Analysis, 43(1):83-88, Elsevier Science, England, (2007).

Rice, C.R., et al., "The Coordination Chemistry of 3,3'-Diamino-2,2'-bipyridine and Its Dication: Exploring the Role of the Amino Groups by X-ray Crystallography," European Journal of Inorganic Chemistry, 2002(8):1985-1997, Wiley-VCH Verlag GmbH & Co. KGaA, Weinheim (2002).

Rocha, L., et al., "N-Acetyltransferase (NAT2) genotype and susceptibility to sporadic Alzheimer's disease," Pharmacogenetics, 9:9-15, Chapman & Hall, England (1999).

Von Schmiedeberg, S., et al., "Polymorphisms of the xenobiotic-metabolizing enzymes CYP1A1 and NAT-2 in systemic sclerosis and lupus erythematosus, " RHEUMADERM: Current Issues in Rheumatology and Dermatology, Mallia, C., and Uitto, J., ed., Chapter 21, pp. 147-152, Kluwer Academic/Plenum Publishers, United States (1999).

Schwalbe, C.H., et al., "A Neutron Diffraction Study of 2,6-Diaminopyridine* at 20 K," Acta Crystallographica, C43:2191-2195, International Union of Crystallography, England (1987).

Sinha, V.R., et al., "Poly-ϵ-caprolactone microspheres and nanospheres: an overview," International Journal of Pharmaceutics, 278(1):1-23, Elsevier/North-Holland Biomedical Press, Netherlands, (2004).

Solari, A., et al., "Aminopyridines for symptomatic treatment in multiple sclerosis," The Cochrane Database of Systematic Reviews, 4:CD001330, Wiley, England, (2002).

Wu, R. and Brutschy, B., "Infrared Depletion Spectroscopy and Structure of the 2-Aminopyridine Dimer," The Journal of Physical Chemistry A, 108(45):9715-9720, American Chemical Society, United States (2004).

Do, B., et al., "HPLC Method for Determination of 3,4-Diaminopyridine in the Presence of Related Substances and Degradation Products Formed Under Stress Conditions," Chromatographia, 63(11/12):599-603, Vieweg & Sohn/GWV Fachverlage GmbH, Weisbaden, Germany (2006).

(56) References Cited

OTHER PUBLICATIONS

Anderson, F.P., et al., "Redetermination or para-aminopyridine (fampridine, EL-970) at 150K," *Acta Crystallographica Section E*, E61:01350-01353, International Union of Crystallography, England (2005).

Katritzky, A.R., *Advances in Heterocyclic Chemistry*, vol. 44, Academic Press, Inc., San Diego, United States (1988).

Chatterjee, N., et al., "Powerful Multilocus Tests of Genetic Association in the Presence of Gene-Gene and Gene-Environment Interactions," Am. J. Hum. Genet. 79:1002-1016, American Journal of Human Genetics, Cell Press, United States (2006).

Deitz, A.C., et al., "Impact of Misclassification in Genotype-Exposure Interaction Studies: Example of N-Acetyltransferase 2 (NAT2), Smoking, and Bladder Cancer," Cancer Epidemiology, Biomarkers & Prevention 13(9):1543-1546, American Association for Cancer Research, United States (2004).

Hein, D.W., et al., "Metabolic activation and deactivation of arylamine carcinogens by recombinant human NAT1 and polymorphic NAT2 acetyltransferases," Carcinogenesis 14(8):1633-1638, Oxford University Press, England (1993).

Hein, D.W., et al., "Molecular Genetics and Epidemiology of the NAT1 and NAT2 Acetylation Polymorphisms," Cancer Epidemiology, Biomarkers & Prevention 9:29-42, American Association for Cancer Research, United States (2000).

Hein, D.W., et al., "N-Acetyltransferase SNPs: emerging concepts serve as a paradigm for understanding complexities of personalized medicine," Expert Opin. Drug Metab. Toxicol. 5(4): 353-366, Taylor & Francis, United States (2009).

Jones, A.E., et al., "Variability in drug metabolizing enzyme activity in HIV-infected patients," Eur J. Clin Pharmacol 66(5):475-485, Springer+Science Business Media, Germany (May 2010).

Kuznetsov, I.B., et al., "A web server for inferring the human N-acetyltransferase-2 (NAT2) enzymatic phenotype from NAT2 genotype," Bioinformatics 25(9):1185-1186, Oxford Journals, England (2009).

Moslehi, R., et al., "Cigarette smoking, N-acetyltransferase genes and the risk of advanced Colorectal adenoma," Pharmacogenomics 7(6): Abstract, Future Medicine, United Kingdom (2006).

Sabbagh, A., et al., "Inferring haplotypes at the NAT2 locus: the computational approach," BMC Genetics 6(30):1-13, BioMed Central, United Kingdom (2005).

Sabbagh, A., et al., "Worldwide distribution of NAT2 diversity: Implications for NAT2 evolutionary history," BMC Genetics 9(21):1-14, Biomed Central United Kingdom (2008).

Wu, H., et al., "Structural Basis of Substrate-binding Specificity of Human Arylamine N-Acetyltransferases," Journal of Biological Chemistry 282(41):30189-30197, American Society for Biochemistry and Molecular Biology Inc., United States (2007).

Smith C.A.D., et al., "A simplified assay for the arylamine N-acetyltransferase 2 polymorphism validated by phenotyping with isoniazid," J. Med. Genet. 34:758-760, BMJ Publishing Group Ltd., United States (1997).

\* cited by examiner $C_{max}$ and AUC Ratio of *N*-(4-aminopyridin-3-yl)acetamide metabolite to 3,4-Diaminopyridine for the Experiment Described in Example 4 in rats after the first dose in a fasted state

| Dose | Ratio Metabolite / 3,4-DAP | |
|---|---|---|
| mg/kg | $C_{max}$ | AUC |
| 2 | 17 | 48 |
| 8 | 4.8 | 14 |
| 25 | 2.6 | 5.4 |

FIG. 5

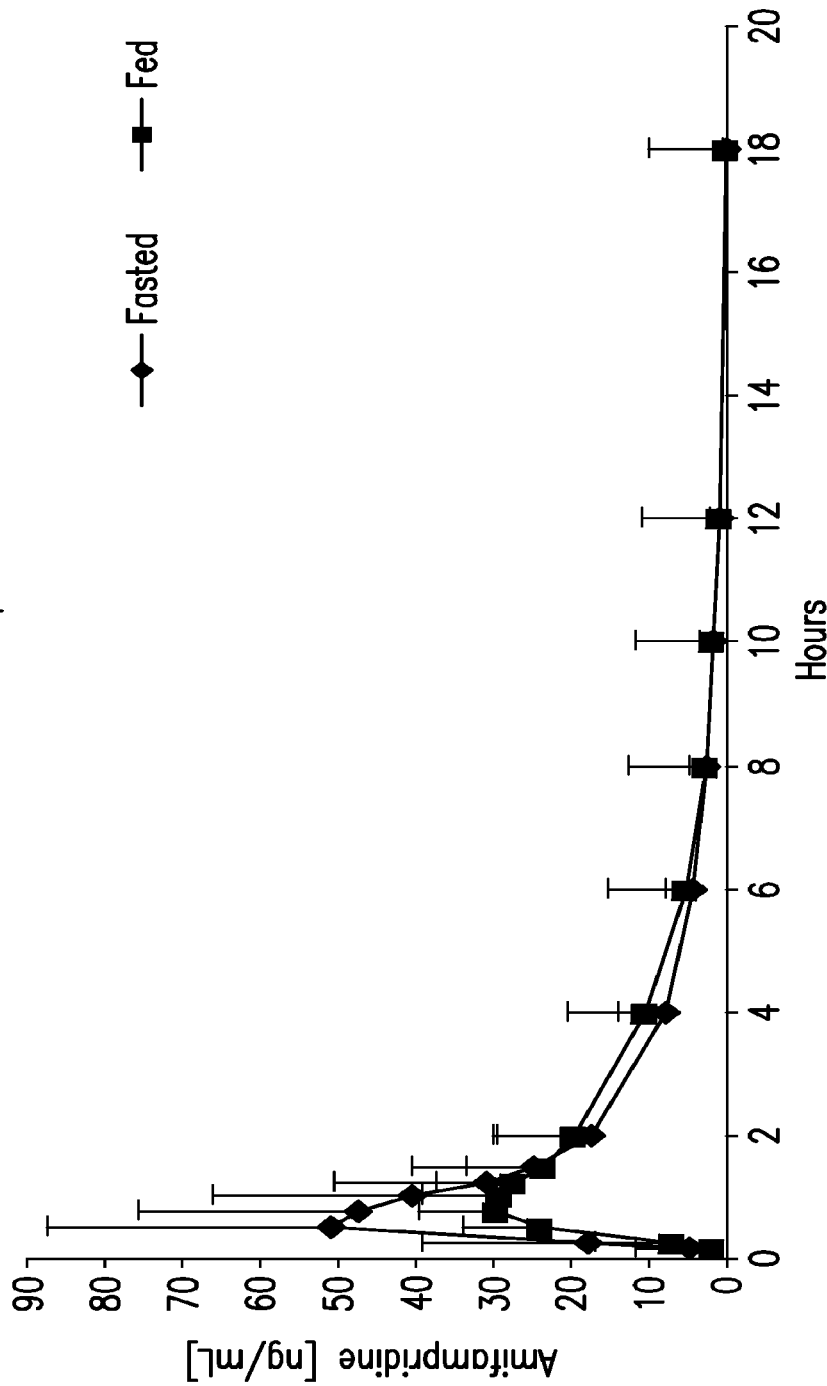

Mean PK Parameters for 3,4-DAP in Fed and Fasted Subjects Following Administration of Oral 3,4-DAP Phosphate for the Experiment Described in Example 10

|  | Treatment | | | | | |
|---|---|---|---|---|---|---|
|  | Fed (N=46) | SD | %CV | Fasted (N=45) | SD | %CV |
| $AUC_{0-t}$ (ng·h/mL) <br> Arithmetic Mean <br> Geometric Mean <br> Median <br> Min-Max | <br> 103 <br> 68.6 <br> 114 <br> 8.30 – 282 | <br> 74.8 | <br> 72.6 | <br> 113 <br> 84.6 <br> 113 <br> 20.6 – 267 | <br> 75.0 | <br> 66.2 |
| $AUC_{0-inf}$ (ng·h/mL) <br> Arithmetic Mean <br> Geometric Mean <br> Median <br> Min-Max | <br> 109 <br> 75.1 <br> 119 <br> 9.66 – 292 | <br> 76.4 | <br> 70.1 | <br> 117 <br> 88.2 <br> 116 <br> 22.1 – 271 | <br> 76.6 | <br> 65.5 |
| $C_{max}$ (ng/mL) <br> Arithmetic Mean <br> Geometric Mean <br> Median <br> Min-Max | <br> 40.6 <br> 27.1 <br> 35.5 <br> 2.81 – 132 | <br> 31.3 | <br> 77.1 | <br> 59.1 <br> 48.5 <br> 57.5 <br> 16.0 – 137 | <br> 34.4 | <br> 58.2 |
| $T_{max}$ (h) <br> Arithmetic Mean <br> Geometric Mean <br> Median <br> Min-Max | <br> 1.31 <br> 1.10 <br> 1.00 <br> 0.50 – 4.00 | <br> 0.880 | <br> 67.1 | <br> 0.637 <br> 0.597 <br> 0.500 <br> 0.25 – 1.50 | <br> 0.247 | <br> 38.7 |
| $t_{1/2}$ (h) <br> Arithmetic Mean <br> Geometric Mean <br> Median <br> Min-Max | <br> 2.28 <br> 2.16 <br> 2.44 <br> 0.822 – 3.78 | <br> 0.704 | <br> 30.9 | <br> 2.50 <br> 2.39 <br> 2.51 <br> 1.23 – 4.31 | <br> 0.730 | <br> 29.2 |
| $\lambda_z$ (1/h) <br> Arithmetic Mean <br> Geometric Mean <br> Median <br> Min-Max | <br> 0.341 <br> 0.321 <br> 0.284 <br> 0.183 – 0.843 | <br> 0.133 | <br> 39.0 | <br> 0.303 <br> 0.290 <br> 0.276 <br> 0.161 – 0.563 | <br> 0.095 | <br> 31.5 |

$AUC_{0-t}$, area under the plasma concentration–time curve from time zero up to the last measurable concentration; $AUC_{0-inf}$, area under the plasma concentration–time curve from time zero to infinity; $C_{max}$, maximum observed plasma concentration; $T_{max}$, time of the maximum observed plasma concentration; $t_{1/2}$, apparent plasma terminal elimination half-life; $\lambda_z$, apparent terminal elimination rate constant; CV, coefficient of variation; SD, standard deviation; h, hour; ng, nanogram; mL, milliliter; N, number of subjects.

2 tablets of 3,4-DAP phosphate (equivalent of 10 mg of 3,4-DAP each) administered

FIG. 11

Mean Pharmacokinetic Parameters for N-(4-aminopyridin-3-yl)acetamide in Fed and Fasted Subjects Following Administration of Oral 3,4-DAP Phosphate (2 x 10 mg tablets) for the Experiment Described in Example 10

| | Treatment | | | | | |
|---|---|---|---|---|---|---|
| | Fed (N=46) | SD | %CV | Fasted (N=45) | SD | %CV |
| $AUC_{0-t}$ (ng·h/mL)<br>Arithmetic Mean<br>Geometric Mean<br>Median<br>Min-Max | 1193<br>1148<br>1132<br>703 - 2364 | 350 | 29.3 | 1415<br>1371<br>1342<br>816 - 2534 | 372 | 26.3 |
| $AUC_{0-inf}$ (ng·h/mL)<br>Arithmetic Mean<br>Geometric Mean<br>Median<br>Min-Max | 1220<br>1174<br>1157<br>715 - 2408 | 355 | 29.1 | 1444<br>1400<br>1381<br>835 - 2595 | 378 | 26.2 |
| $C_{max}$ (ng/mL)<br>Arithmetic Mean<br>Geometric Mean<br>Median<br>Min-Max | 189<br>176<br>167<br>90.1 - 406 | 79.3 | 41.9 | 267<br>253<br>251<br>119 - 609 | 93.4 | 34.9 |
| $T_{max}$ (h)<br>Arithmetic Mean<br>Geometric Mean<br>Median<br>Min-Max | 2.12<br>1.86<br>2.00<br>0.750 - 4.02 | 1.14 | 53.8 | 1.27<br>1.225<br>1.25<br>0.750 - 2.00 | 0.348 | 27.4 |
| $t_{1/2}$ (h)<br>Arithmetic Mean<br>Geometric Mean<br>Median<br>Min-Max | 4.03<br>3.98<br>4.09<br>2.48 - 5.62 | 0.646 | 16.0 | 4.10<br>4.04<br>4.08<br>2.47 - 6.22 | 0.682 | 16.6 |
| $\lambda_z$ (1/h)<br>Arithmetic Mean<br>Geometric Mean<br>Median<br>Min-Max | 0.177<br>0.174<br>0.169<br>0.123 - 0.279 | 0.032 | 18.1 | 0.174<br>0.171<br>0.170<br>0.281 - 0.112 | 0.032 | 18.3 |

$AUC_{0-t}$, area under the plasma concentration-time curve from time zero up to the last measurable concentration; $AUC_{0-inf}$, area under the plasma concentration-time curve from time zero to infinity; $C_{max}$, maximum observed plasma concentration; $T_{max}$, time of the maximum observed plasma concentration; $t_{1/2}$, apparent plasma terminal elimination half-life; $\lambda_z$, apparent terminal elimination rate constant; CV, coefficient of variation; SD, standard deviation; h, hour; ng, nanogram; mL, milliliter; N, number of subjects.

2 tablets of 3,4-DAP phosphate (equivalent of 10 mg of 3,4-DAP each) administered

FIG. 13

Mean, Maximal and Minimal Urinary Excretion of Amifampridine and
3-N-Acetyl Amifampridine in Fed and Fasted Subjects Receiving Oral Amifampridine
Phosphate for the Experiment Described in Example 10

|  | Urinary Excretion in Dose (fe%) | | | | Total % Dose Urinary Excretion | |
|---|---|---|---|---|---|---|
|  | Amifampridine | | 3-N-Acetyl Amifampridine | | Amifampridine and 3-N-Acetyl Amifampridine | |
|  | Fed | Fasted | Fed | Fasted | Fed | Fasted |
| Arithmetic Mean | 19.2 | 18.8 | 74.0 | 81.7 | 93.2 | 100 |
| SD | 12.8 | 11.8 | 18.3 | 15.3 | 12.4 | 11.7 |
| %CV | 67.0 | 62.8 | 24.7 | 18.8 | 13.3 | 11.6 |
| Minimum | 0.936 | 2.34 | 26.9 | 42.7 | 54.6 | 69.8 |
| Maximum | 42.2 | 36.3 | 104 | 122 | 121 | 126 |

CV, coefficient of variation; SD, standard deviation; fe, fraction of dose excreted in urine 2 tablets of amifampridine phosphate (equivalent of 10 mg of amifampridine each) administered

FIG. 14

Schedule of Events for the Experiment Described in Example 10

| Event | Screening Days −28 to −2 | Treatment Period 1 Day −1 (Check-in) | Treatment Period 1 Day 1 | Treatment Period 1 Day 2 | Washout Days 2 to 7 | Treatment Period 2 Day 7 (Check-in) | Treatment Period 2 Day 8 | Treatment Period 2 Day 9 | Follow-up Days 13 to 15[l] | Early Termination |
|---|---|---|---|---|---|---|---|---|---|---|
| Informed consent[a] | X | | | | | | | | | |
| Randomization | | X | | | | | | | | |
| Clinic days[b] | X | X | X | X | | X | X | X | X | X |
| Medical history | X | | | | | | | | | |
| Complete physical examination[c] | X | | | | | | | | X | X |
| Height, weight, BMI | X | | | | | | | | | |
| Vital signs | X | | X[d] | X | | | X[d] | X | X | X |
| Urine drug and cotinine screen and alcohol breath test[e] | X | X | | | | X | | | | |
| Pregnancy test[f] | X | X | | | | X | | | X | X |
| Thyroid panel, HIV, and hepatitis B and C tests | X | | | | | | | | | |
| ECG measurement | X | | X[g] | | | | X[g] | | | X[m] |
| Clinical laboratory tests (Hematology, chemistry, urinalysis)[h] | X | X | | | | | X | | X | X |
| Blood and urine PK sampling[i] | | | X | X | | | X | X | | |
| Dosing with investigational product[j] | | | X | | | | X | | | |
| Adverse event assessment[k] | | X | X | X | | X | X | X | X | X |
| Begin fasting (fast) | | X | | | | X | | | | |
| Meal served (fed)[n] | | | X | | | | X | | | |
| Concomitant medication assessment | X | X | X | X | | X | X | X | X | X |

BMI, body mass index; CRU, Clinical Research Unit; ECG, electrocardiogram; HIV, humanimmunodeficiency virus; PK, pharmacokinetic; SAE, serious adverse event

FIG. 15 a Informed consent was obtained before any study procedures were performed.
b Subjects resided in the CRU from the afternoon of Day −1 through the morning of Day 2 (approximately 24 hours post dose) and from the afternoon of Day 7 to the morning of Day 9. A washout period of 6 (up to 10) days separated each dose administration.
c Complete physical examinations included the evaluation of all major body systems.
d Vital signs were obtained in the dominant arm, thereby saving the non-dominant arm for blood draws. Vital signs were recorded ≤ 90 min prior to dose and post dose at 0.5, 1, 2, 4, 8, and 24 hours.
e Urine drug abuse screens included testing for amphetamines, methadone, benzodiazepines, barbiturates, cocaine, tetrahydrocannabinol (cannabinoids), opiates, cotinine, and tricyclic antidepressants.
f Serum pregnancy tests were performed at Screening, at all other time points urine pregnancy tests were performed. A hormone panel was performed if the urine pregnancy test result was considered to be a false positive.
g ECGs were collected twice on Days 1 and 8 at ≤ 90 min pre dose and approximately 30 (±5) min post dose (estimated time of the maximum observed plasma concentration [$T_{max}$]).
h Clinical laboratory tests included hematology, chemistry, urinalysis, thyroid panel, hepatitis B and C, and HIV at Screening. Hematology, chemistry, and urinalysis only were repeated prior to dosing administration on dosing days and at the Follow-up visit or Early Termination.
i Blood samples for PK analyses were taken at the following time points during each study period: 90 ± 5 min prior to dose, 10, 15, 30, 45, 60, 75 min, 1.5, 2, 4, 6, 8, 10, 12, 18, and 24 hours post dose for blood samples. Urine samples were collected at the following times and intervals: ≤ 90 min prior to dose (single sample), 0 to 4 hours, 4 to 8 hours, and 8 to 24 hours. Plasma samples generated from blood and urine (40 to 50 mL) sample aliquots from each collection period were divided into duplicate samples of approximately equal proportion for each collection period, labelled (A and B), and stored on dry ice or at −70°C until transfer to a Good Laboratory Practice freezer environment for storage until analysis.
j Investigational product was administered with 240 mL of water and was ingested 30 (±5) min after the start of the high fat meal in Treatment B.
k The reporting period for non-serious AEs was the period from the first administration of study drug to the final visit. The reporting period for SAEs began when informed consent was signed and was followed until resolution, even if this extended beyond the study-reporting period.
l A post study assessment was performed 5 to 7 days (Days 13 to 15) after the last dose.
m ECG at Early Termination visit only occurred if abnormalities were detected on previous ECGs.
n Day 1 meal was served to Group 2 only. Day 8 meal was served to Group 1 only.

FIG. 15 continued

Mean PK parameters (arithmetic values) for the clinical trial described in Example A.

Results expressed as mean SD, [95% CI], (median) and {geometric mean}

|  | Administration A (free base) N=26 | Administration B (free base) N=26 |
|---|---|---|
| AUC [h·ng/mL] | 121.2±62.1 [96.2–146.3] (108.6) {106.4} CV: 51.2% | 127.3±77.1 [96.1–158.4] (115.9) {109.3} 60.6% |
| %AUC [%] | 4.9±6.2 [2.4–7.4] (3.4) {3.5} | 3.5±1.9 [2.8–4.3] (3.3) {3.1} |
| AUC(0–tn)[h·ng/mL] | 115.8±61.2 [91.1–140.5] (104.6) {101} | 122.7±74.6 [92.6–152.8] (112) {105.4} |
| $C_{max}$ [ng/mL] | 64.8±39.7 [48.8–80.9] (61.7) {51.8} CV: 61.2% | 57±38.6 [41.4–72.6] (48.6) {44.7} 67.7% |
| $\lambda z$ [h−1] | 0.8±0.8 [0.5–1.2] (0.5) {0.6} | 0.9±1.0 [0.5–1.3] (0.6) {0.6} |
| $t_{max}$ [h] | 0.6±0.3 [0.4–0.7] (0.5) {0.5} | 0.9±0.4 [0.7–1] (0.8) {0.8} |
| $t_{1/2}$ [h] | 1.8±1.9 [1.0–2.6] (1.4) {1.2} | 1.6±1.2 [1.1–2.1] (1.3) {1.2} |

CV: Coefficient of variation

FIG. 16

Mean values of 3,4-DAP phosphate and free base (ng/mL) at time sampling for the clinical trial described in Example A.
(values below LOQ are fixed at zero)

| Time (min) | Phosphate | | Free Base | |
|---|---|---|---|---|
| | Mean | SEM | Mean | SEM |
| 0 | 0 | 0 | 0 | 0 |
| 5 | 0 | 0 | 0.56 | 0.56 |
| 10 | 0 | 0 | 12.32 | 3.90 |
| 15 | 4.36 | 1.03 | 29.84 | 7.54 |
| 20 | 14.55 | 4.56 | 38.32 | 7.98 |
| 30 | 32.62 | 6.39 | 44.36 | 6.85 |
| 45 | 39.17 | 8.47 | 36.11 | 6.52 |
| 60 | 36.00 | 6.03 | 24.35 | 6.37 |
| 75 | 26.29 | 5.09 | 21.98 | 4.32 |
| 90 | 20.24 | 4.90 | 17.16 | 3.97 |
| 120 | 12.31 | 3.38 | 8.50 | 2.06 |
| 240 | 4.84 | 0.98 | 4.03 | 0.87 |
| 306 | 2.27 | 0.73 | 2.41 | 0.69 |
| 480 | 0.94 | 0.45 | 0.97 | 0.46 |
| 660 | 0.57 | 0.40 | 0 | 0 |
| 1440 | 0 | 0 | 0 | 0 |

SEM: standard erroe of the mean;
LOQ: limit of quantitation (5 ng/mL)

FIG. 17

3,4-DAP as phosphate salt or free base: arithmetic means for the clinical trial described in Example A.

3,4-DAP as phosphate salt or free base: arithmetic means for the clinical trial described in Example A.

90% CI for AUCs and $C_{max}$ Free base/Phosphate salt Ratio for the clinical trial described in Example A.

|  |  | No transformed data | | Log-transformed data | |
| --- | --- | --- | --- | --- | --- |
|  |  | Point estimate | Shortest IC 90 % | Point estimate | Shortest IC 90 % |
| Ratio | $\frac{AUC_{0\to\infty}B}{AUC_{0\to\infty}S}$ x 100 | 107.1 | 96.0–118.1 | 102.7 | 93.1–113.3 |
| Ratio | $\frac{C_{max}Base}{C_{max}Sel}$ x 100 | 94.1 | 81.0–107.2 | 86.3 | 73.9–100.8 |

FIG. 19A

Time to reach $C_{max}$ for the clinical trial described in Example A.

|  | Median | 95 % CI | p |
| --- | --- | --- | --- |
| Δ t max B – t max S (min) | 15 | 10–25 | 0.0005* |
| Δ t' max B – t' max S (min) | 10 | 0–20 | 0.0013** | t' = tmax – tlag
* No pramateric sign test
** Wilcoxon test

FIG. 19B

Concentration Response Data for 3,4-DAP Phosphate and 3-N-acetyl DAP HCl in CHO Cells Transiently Transfected with hKv1.7

| Test Article | Concentration (μM) | Percent Inhibition | | | IC$_{50}$ (μM) |
|---|---|---|---|---|---|
| | | Mean | SD | N | |
| 3,4-DAP Phosphate | 1 | 0.5% | 0.2% | 2 | 338.4 |
| | 10 | 3.7% | 1.1% | 2 | |
| | 30 | 10.6% | 1.3% | 2 | |
| | 100 | 23.9% | 0.6% | 2 | |
| | 300 | 50.2% | 4.2% | 2 | |
| | 1000 | 74.2% | 0.1% | 2 | |
| | 3000 | 81.0% | 0.1% | 2 | |
| 3-N-acetyl DAP HCl | 100 | 1.0% | 0.1% | 2 | > 3000 |
| | 1000 | 2.8% | 0.8% | 2 | |
| | 3000 | 8.4% | 1.8% | 2 | |

FIG. 20

Concentration Response Data for 3,4-DAP Phosphate and 3-N-acetyl DAP HCl in CHO or HEK293 Cells Transiently Transfected with hKv1.1, hKv1.2, and hKv1.3

| Channel | Test Article | Concentration (µM) | % Inhibition Mean | % Inhibition SD | N | IC$_{50}$ (µM) |
|---|---|---|---|---|---|---|
| hKv1.1 | 3,4-DAP phosphate | 1 | 1.4 % | 5.0 % | 2 | 767.5 |
| | | 10 | 4.6 % | 1.6 % | 2 | |
| | | 30 | 8.9 % | 4.9 % | 2 | |
| | | 100 | 22.1 % | 3.2 % | 2 | |
| | | 300 | 37.6 % | 1.4 % | 2 | |
| | | 1000 | 53.6 % | 1.8 % | 2 | |
| | | 3000 | 69.6 % | 5.4 % | 2 | |
| | 3-N-acetyl 3,4-DAP HCl | 100 | 1.6 % | 0.8 % | 2 | > 3000 |
| | | 1000 | 0.5 % | 2.0 % | 2 | |
| | | 3000 | 4.0 % | 3.6 % | 2 | |
| hKv1.2 | 3,4-DAP phosphate | 1 | 0.8 % | 1.1 % | 2 | 1278.8 |
| | | 10 | -0.1 % | 1.5 % | 2 | |
| | | 30 | -3.4 % | 5.1 % | 2 | |
| | | 100 | 6.4 % | 7.4 % | 2 | |
| | | 300 | 24.3 % | 1.8 % | 2 | |
| | | 1000 | 43.3 % | 0.7 % | 2 | |
| | | 3000 | 68.6 % | 4.8 % | 2 | |
| | 3-N-acetyl 3,4-DAP HCl | 100 | -2.2 % | 2.7 % | 2 | > 3000 |
| | | 1000 | 5.0 % | 5.7 % | 2 | |
| | | 3000 | 2.2 % | 0.2 % | 2 | |
| hKv1.3 | 3,4-DAP phosphate | 1 | 0.1 % | 1.6 % | 2 | 524.8 |
| | | 10 | 7.4 % | 3.2 % | 2 | |
| | | 30 | 3.8 % | 1.7 % | 2 | |
| | | 100 | 19.0 % | 0.5 % | 2 | |
| | | 300 | 43.2 % | 6.9 % | 2 | |
| | | 1000 | 61.2 % | 10.0 % | 2 | |
| | | 3000 | 79.7 % | 1.5 % | 2 | |
| | 3-N-acetyl 3,4-DAP HCl | 100 | -2.0 % | 1.8 % | 2 | > 3000 |
| | | 1000 | -0.1 % | 3.2 % | 2 | |
| | | 3000 | 19.5 % | 3.9 % | 2 | |

FIG. 21A

Concentration Response Data for 3,4-DAP Phosphate and 3-N-acetyl DAP HCl in CHO or HEK293 Cells Transiently Transfected with hKv1.4 and hKv1.5

| Channel | Test Article | Concentration (μM) | % Inhibition Mean | SD | N | IC$_{50}$ (μM) |
|---|---|---|---|---|---|---|
| hKv1.4 | 3,4-DAP phosphate | 1 | -1.8 % | 2.0 % | 2 | 1860.3 |
| | | 10 | 3.8 % | 0.6 % | 2 | |
| | | 30 | -0.5 % | 4.6 % | 2 | |
| | | 100 | 0.0 % | 1.8 % | 2 | |
| | | 300 | 12.1 % | 2.6 % | 2 | |
| | | 1000 | 24.4 % | 4.7 % | 2 | |
| | | 3000 | 69.2 % | 1.4 % | 2 | |
| | 3-N-acetyl 3,4-DAP HCl | 100 | 7.1 % | 4.8 % | 2 | > 3000 |
| | | 1000 | 13.6 % | 0.3 % | 2 | |
| | | 3000 | 21.5 % | 3.6 % | 2 | |
| hKv1.5 | 3,4-DAP phosphate | 1 | 0.8 % | 2.7 % | 2 | 490.8 |
| | | 10 | 6.2 % | 2.0 % | 2 | |
| | | 30 | 8.7 % | 5.2 % | 2 | |
| | | 100 | 30.4 % | 3.5 % | 2 | |
| | | 300 | 39.3 % | 2.7 % | 2 | |
| | | 1000 | 59.8 % | 8.6 % | 2 | |
| | | 3000 | 77.8 % | 2.2 % | 2 | |
| | 3-N-acetyl 3,4-DAP HCl | 100 | -0.3 % | 0.2 % | 2 | > 3000 |
| | | 1000 | 4.5 % | 4.3 % | 2 | |
| | | 3000 | 2.7 % | 4.7 % | 2 | |

FIG. 21B

Mean Pharmacokinetic Parameters (±SD) of 3,4-DAP in Healthy Subjects after Single Oral Doses of Firdapse® (5-30 mg 3,4-DAP base equivalents) in Slow and Fast acetylator Phentoypes for the Trial Described in Example 18, Part 1

| 3,4-DAP PhosphateDose (mg base equiv) | | 5 | | 10 |
|---|---|---|---|---|
| FIR001 Part 1 | Values (+/-SD) | Values (+/-SD) | Values (+/-SD) | Values (+/-SD) |
| Subjects (N) | 6 | 6 | 6 | 6 |
| Acetylator Phenotype | Fast | Slow | | Fast |
| Caffeine Acetylation Ratio | 0.408 (0.031) | 0.172 (0.023) | | 0.408 (0.031) |
| Mean 3,4-DAP PK Parameters | | | | |
| $AUC_{0-t}$ (ng·h/mL) | 2.89 (0.660) | 30.1 (7.25) | | 9.55 (1.77) |
| $AUC_{0-inf}$ (ng·h/mL) | 3.57 (0.585) | 32.1 (7.34) | | 11.1 (1.90) |
| $C_{max}$ (ng·h/mL) | 3.98 (1.71) | 17.9 (4.43) | | 9.91 (5.28) |
| $T_{max}$ (h) | 0.750 (0.387) | 0.830 (0.408) | | 0.805 (0.411) |
| $t_{1/2}$ (h) | 0.603 (0.304) | 2.22 (0.855) | | 1.21 (0.279) |
| CL/F (L/h) | 1431 (234) | 163 (37.4) | | 920 (155) |
| Vdz/F (L) | 1254 (622) | 509 (199) | | 1575 (343) |
| Vdss/F (L) | 1763 (780) | 434 (142) | | 1577 (516) |

Note: CL/F, Vdz/F and Vdss/F were calculated in mL and converted to Liters.

FIG. 24A

|  | | 20 | | 30 | |
| --- | --- | --- | --- | --- | --- |
| Values (+/-SD) | Values (+/-SD) | Values (+/-SD) | Values (+/-SD) | Values (+/-SD) | Values (+/-SD) |
| 6 | 6 | 6 | 6 | 6 | 6 |
| Slow | Fast | Fast | Slow | Fast | Slow |
| 0.172 (0.023) | 0.408 (0.031) | 0.408 (0.031) | 0.172 (0.023) | 0.408 (0.031) | 0.172 (0.023) |
| 66.3 (12.8) | 24.7 (2.47) | 43.5 (6.39) | 142 (32.1) | 43.5 (6.39) | 230 (44.9) |
| 68.9 (12.8) | 26.2 (2.62) | 45.2 (6.44) | 146 (31.4) | 45.2 (6.44) | 234 (44.7) |
| 34.4 (21.6) | 16.2 (4.56) | 25.5 (7.17) | 56.7 (16.1) | 25.5 (7.17) | 89.6 (9.05) |
| 1.14 (0.492) | 1.04 (0.368) | 0.810 (0.411) | 1.07 (0.543) | 0.810 (0.411) | 1.29 (0.459) |
| 2.60 (0.688) | 1.23 (0.309) | 1.65 (0.634) | 2.93 (0.588) | 1.65 (0.634) | 3.11 (0.572) |
| 150 (32.1) | 770 (67.5) | 675 (98.5) | 143 (32.3) | 675 (98.5) | 132 (20.5) |
| 577 (252) | 1363 (337) | 1621 (703) | 607 (211) | 1621 (703) | 592 (146) |
| 459 (175) | 1682 (365) | 1590 (374) | 481 (181) | 1590 (374) | 430 (79.9) |

FIG. 24A continued

Mean Pharmacokinetic Parameters (±SD) of N-(4-aminopyridin-3-yl)acetamide in Healthy Subjects after Single Oral Doses of Firdapse® (5-30 mg BMN125 base equivalents) in Slow and Fast acetylator Phentoypes

| 3NAc-DAP Dose (mg base equivalents) | 5 | | | | 10 | |
|---|---|---|---|---|---|---|
| FIR001 Part 1 | Values (+/-SD) | | Values (+/-SD) | | Values (+/-SD) | |
| Subjects (N) | 6 | | 6 | | 6 | |
| Acetylator Phenotype | Fast | | Slow | | Fast | |
| Caffeine Acetylation Ratio | 0.408 (0.031) | | 0.172 (0.023) | | 0.408 (0.031) | |
| Mean 3NAcDAP PK Parameters | | | | | | |
| AUC$_{0-t}$ (ng·h/mL) | 286 (33.9) | | 205 (37.4) | | 609 (82.6) | |
| AUC$_{0-inf}$ (ng·h/mL) | 295 (33.0) | | 212 (35.6) | | 619 (83.5) | |
| C$_{max}$ (ng·h/mL) | 82.3 (21.8) | | 43.2 (14.5) | | 162 (56.2) | |
| T$_{max}$ (h) | 1.13 (0.565) | | 1.21 (0.401) | | 1.25 (0.447) | |
| t$_{1/2}$ (h) | 3.06 (0.569) | | 3.72 (1.11) | | 3.78 (1.25) | |
| CL/F (L/h) | 17.1 (1.72) | | 24.1 (3.64) | | 16.4 (2.02) | |
| Vdz/F (L) | 75.9 (16.9) | | 131 (49.3) | | 90.2 (34.7) | |
| Vdss/F (L) | 76.3 (15.1) | | 138 (51.3) | | 80.9 (25.8) | |

Note: CL/F, Vdz/F and Vdss/F were calculated in mL and converted to Liters. 3NAc-DAP = 3-N-acetyldiaminopyridine.

FIG. 24B

|  | | 20 | | 30 | |
| --- | --- | --- | --- | --- | --- |
| Values (+/-SD) | Values (+/-SD) | Values (+/-SD) | Values (+/-SD) | Values (+/-SD) | Values (+/-SD) |
| 6 | 6 | 6 | 6 | 6 | 6 |
| Slow | Fast | Fast | Slow | Fast | Slow |
| 0.172 (0.023) | 0.408 (0.031) | 0.408 (0.031) | 0.172 (0.023) | 0.408 (0.031) | 0.172 (0.023) |
| 422 (81.2) | 1199 (120) | 1213 (119) | 801 (128) | 1687 (190) | 1115 (185) |
| 434 (79.6) | 1213 (119) | | 818 (130) | 1706 (190) | 1140 (185) |
| 80.6 (12.7) | 268 (57.5) | | 138 (21.1) | 350 (40.5) | 189 (31.8) |
| 1.50 (0.632) | 1.58 (0.465) | | 1.75 (0.418) | 1.50 (0.418) | 1.67 (0.408) |
| 4.29 (1.21) | 3.63 (1.01) | | 4.31 (0.630) | 3.63 (0.640) | 4.35 (0.500) |
| 23.6 (3.92) | 16.6 (1.68) | | 25.0 (3.84) | 17.8 (1.91) | 26.9 (4.27) |
| 146 (48.5) | 86.7 (25.4) | | 155 (34.8) | 92.9 (19.8) | 171 (42.3) |
| 140 (29.1) | 83.0 (18.1) | | 153 (26.4) | 90.8 (16.4) | 171 (42.5) |

FIG. 24B continued

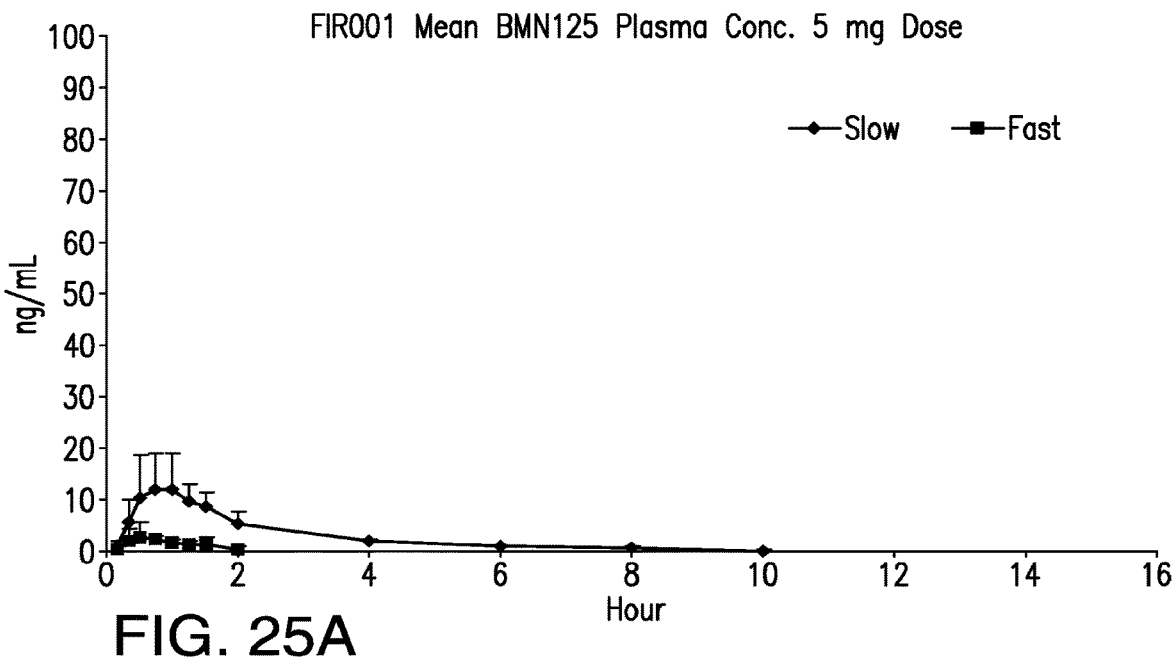

Mean Plasma Concentration-Time Profiles of BMN125 After Single Oral Doses of Firdapse® at 5, 10, 20 and 30 mg (base equivalents) in Healthy Subjects with Slow and Fast Acetylator Phenotypes for the Trial Described in Example 18, Part 1

FIG. 25A

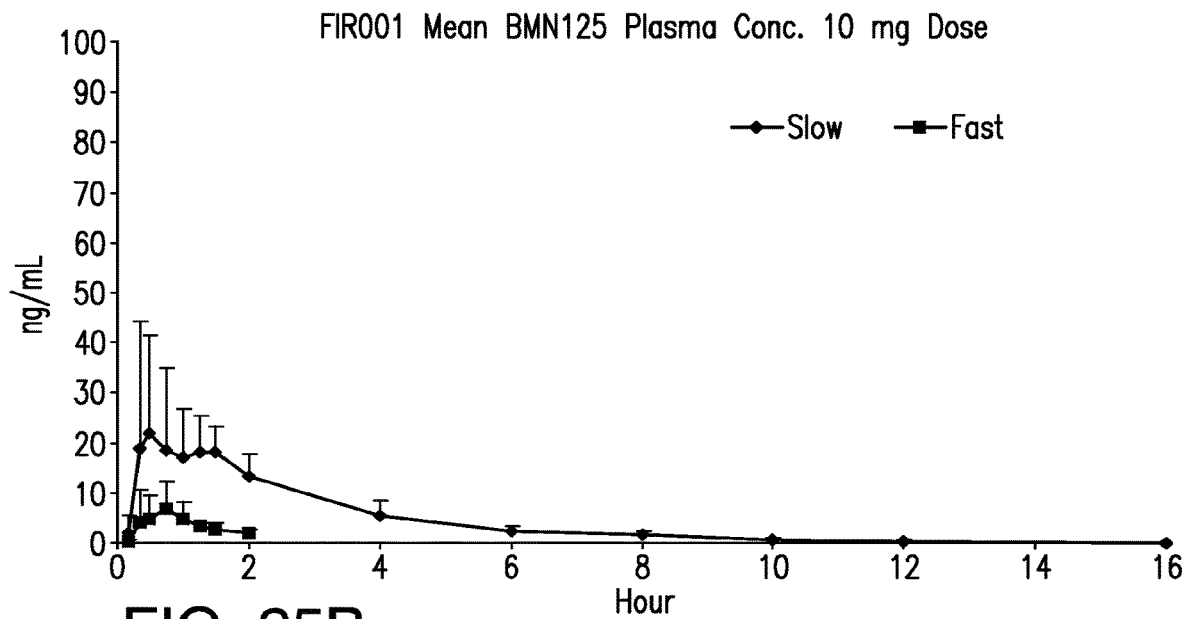

Mean Plasma Concentration-Time Profiles of BMN125 After Single Oral Doses of Firdapse® at 5, 10, 20 and 30 mg (base equivalents) in Healthy Subjects with Slow and Fast Acetylator Phenotypes for the Trial Described in Example 18, Part 1

FIG. 25B

Mean Plasma Concentration-Time Profiles of BMN125 After Single Oral Doses of Firdapse® at 5, 10, 20 and 30 mg (base equivalents) in Healthy Subjects with Slow and Fast Acetylator Phenotypes for the Trial Described in Example 18, Part 1

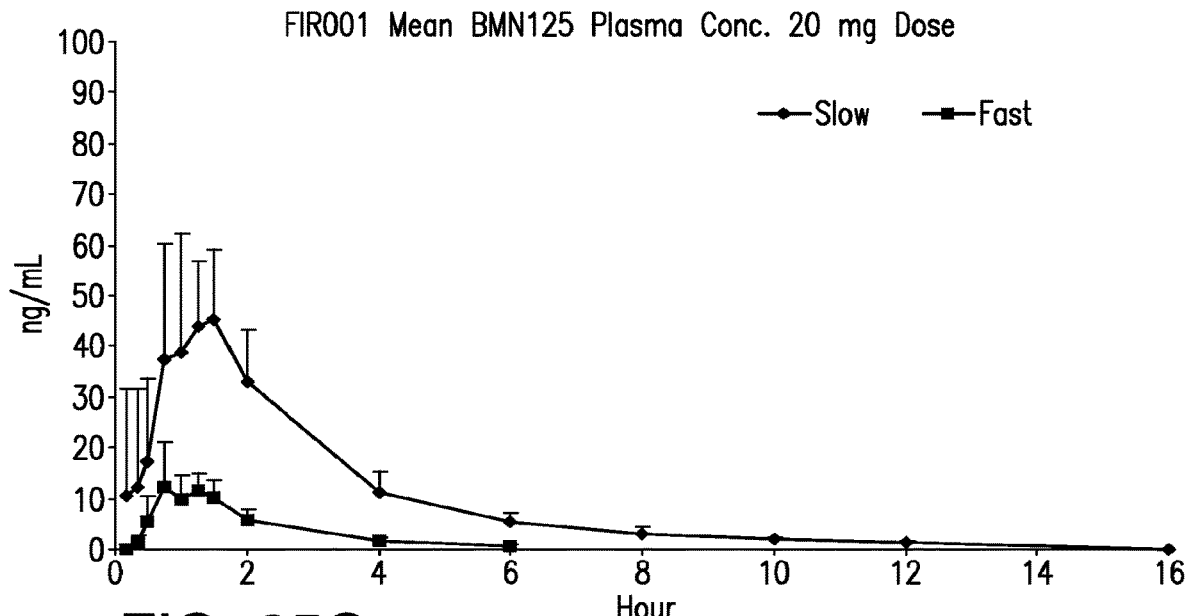

FIG. 25C

Mean Plasma Concentration-Time Profiles of BMN125 After Single Oral Doses of Firdapse® at 5, 10, 20 and 30 mg (base equivalents) in Healthy Subjects with Slow and Fast Acetylator Phenotypes for the Trial Described in Example 18, Part 1

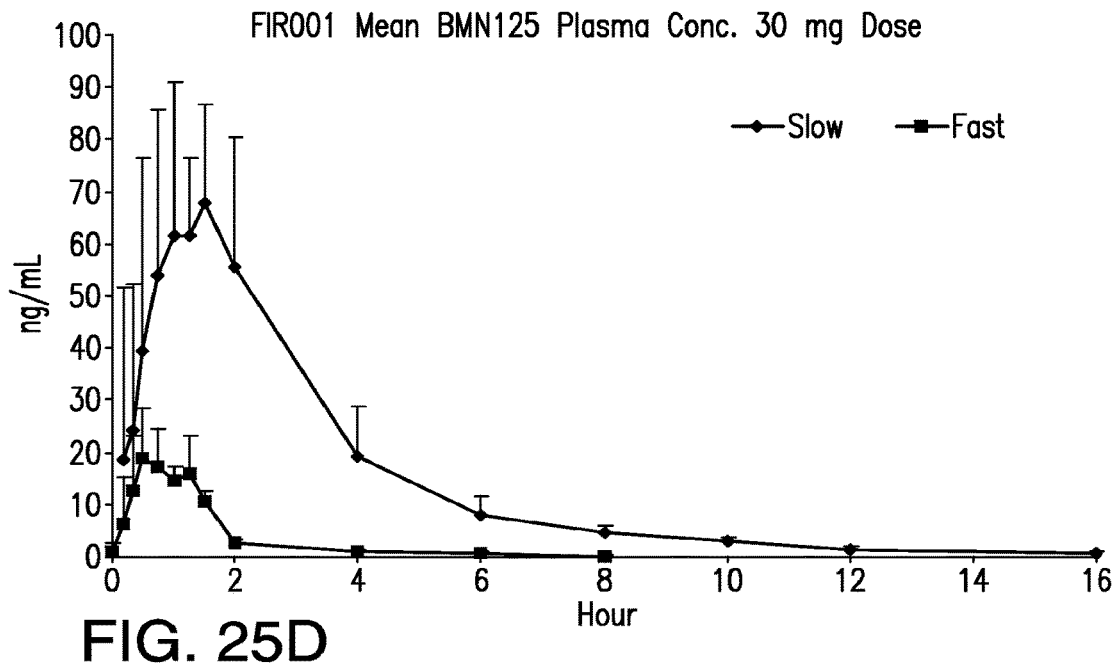

FIG. 25D

Mean Plasma Concentrations of 3,4-DAP in Slow and Fast Acetylators, QID Dosing of Firdapse® (20 mg base equiv), Day 1, 3 and 4 for the Trial Described in Example 18, Part 2.

Mean Plasma Concentrations of 3,4-DAP in Slow and Fast Acetylators, QID Dosing of Firdapse® (20 mg base equiv), Day 1, 3 and 4 for the Trial Described in Example 18, Part 2.

Mean Plasma Concentrations of N-(4-aminopyridin-3-yl)acetamide in Slow and Fast Acetylators, QID Dosing of Firdapse® (20 mg base equiv) on Day 1, 3, and 4 for the Trial Described in Example 18, Part 2.

Mean Plasma Concentrations of N-(4-aminopyridin-3-yl)acetamide in Slow and Fast Acetylators, QID Dosing of Firdapse® (20 mg base equiv) on Day 1, 3, and 4 for the Trial Described in Example 18, Part 2.

Mean Plasma Concentrations of N-(4-aminopyridin-3-yl)acetamide in Slow and Fast Acetylators, QID Dosing of Firdapse® (20 mg base equiv) on Day 1, 3, and 4 for the Trial Described in Example 18, Part 2.

Treatment-emergent drug-related adverse events by treatment and phenotype for Part 1 of the Study in Example 18.

| System/organ class /preferred term | Day 1, 5 mg | | | | | | Day 2, 10 mg | | | | | | Day 3, 20 mg | | | | | | Day 4-7, 30 mg | | | | | |
|---|---|---|---|---|---|---|---|---|---|---|---|---|---|---|---|---|---|---|---|---|---|---|---|---|
| | fast (N=6) | | | slow (N=6) | | | fast (N=6) | | | slow (N=6) | | | fast (N=6) | | | slow (N=6) | | | fast (N=6) | | | slow (N=6) | | |
| | E | n | % | E | n | % | E | n | % | E | n | % | E | n | % | E | n | % | E | n | % | E | n | % |
| Total | | | | 1 | 1 | 17 | | | | | | | | | | 14 | 5 | 83 | | | | 13 | 6 | 100 |
| Eye disorders | | | | | | | | | | | | | | | | 1 | 1 | 17 | | | | 1 | 1 | 17 |
| conjunctivitis | | | | | | | | | | | | | | | | | | | | | | 1 | 1 | 17 |
| blurred vision | | | | | | | | | | | | | | | | 1 | 1 | 17 | | | | | | |
| Gastrointestinal disorders | | | | | | | | | | | | | | | | | | | | | | 1 | 1 | 17 |
| diarrhea | | | | 1 | 1 | 17 | | | | | | | | | | | | | | | | | | |
| Nervous system disorders | | | | | | | | | | | | | | | | 12 | 5 | 83 | | | | 11 | 6 | 100 |
| postural dizziness | | | | | | | | | | | | | | | | 1 | 1 | 17 | | | | 1 | 1 | 17 |
| headache | | | | 1 | 1 | 17 | | | | | | | | | | 1 | 1 | 17 | | | | | | |
| paraesthesia | | | | | | | | | | | | | | | | 6 | 5 | 83 | | | | 5 | 4 | 67 |
| paraesthesia, oral | | | | | | | | | | | | | | | | 4 | 4 | 67 | | | | 5 | 5 | 83 |
| Psychiatric disorders | | | | | | | | | | | | | | | | 1 | 1 | 17 | | | | | | |
| anxiety | | | | | | | | | | | | | | | | 1 | 1 | 17 | | | | | | |

FIG. 28

Treatment-emergent drug-related adverse events by treatment and phenotype for Part 2 of the Study in Example 18.

| | Group 1, 20 mg QID | | | | | | Group 2, 20 mg | | | | | | Total | | | | | |
|---|---|---|---|---|---|---|---|---|---|---|---|---|---|---|---|---|---|---|
| | fast (N=2) | | | slow (N=2) | | | fast (N=5) | | | slow (N=5) | | | fast (N=7) | | | slow (N=7) | | |
| System/organ class /preferred term | E | n | % | E | n | % | E | n | % | E | n | % | E | n | % | E | n | % |
| Total | 4 | 1 | 50 | 11 | 2 | 100 | 2 | 2 | 40 | 34 | 4 | 80 | 6 | 3 | 43 | 45 | 6 | 86 |
| Gastrointestinal disorders | | | | | | | | | | | | | | | | | | |
| abdominal discomfort | | | | | | | 1 | 1 | 20 | 1 | 1 | 20 | | | | 1 | 1 | 14 |
| nausea | | | | | | | 1 | 1 | 20 | | | | 1 | 1 | 14 | | | |
| Nervous system disorders | 4 | 1 | 50 | 11 | 2 | 100 | 1 | 1 | 20 | 33 | 4 | 80 | 5 | 2 | 29 | 44 | 6 | 86 |
| dizziness | | | | | | | | | | 1 | 1 | 20 | | | | 1 | 1 | 14 |
| paraesthesia | 2 | 1 | 50 | 5 | 2 | 100 | | | | 10 | 4 | 80 | 2 | 1 | 14 | 15 | 6 | 86 |
| paraesthesia, oral | 2 | 1 | 50 | 6 | 2 | 100 | 1 | 1 | 20 | 22 | 4 | 80 | 3 | 2 | 29 | 28 | 6 | 86 |

FIG. 29

METHODS OF ADMINISTERING 3,4-DIAMINOPYRIDINE

CROSS REFERENCE TO RELATED APPLICATIONS

This application claims priority to and is a national stage filing under 35 U.S.C. § 371 of International Patent Application No. PCT/US2012/044904, filed on Jun. 29, 2012 which claims priority to U.S. provisional patent application 61/553,045, filed on Oct. 28, 2011 and U.S. provisional patent application 61/503,553 filed on Jun. 30, 2011; the disclosures of which are incorporated by reference in their entirety.

FIELD

Provided herein are methods of determining NAT acetylation status of a subject with a 3,4-DAP-sensitive disease, methods of selecting a dose of 3,4-DAP or a pharmaceutically acceptable salt thereof adjusted to a subject's acetylation status, methods of administering 3,4-diaminopyridine or a pharmaceutically acceptable salt thereof to a patient in need thereof, and methods of treating 3,4-DAP sensitive diseases.

BACKGROUND

It has been described that 3,4-diaminopyridine can be used for the treatment of myasthenia gravis and myasthenic syndromes (including Lambert-Eaton myasthenic syndrome, congenital myasthenia, and myasthenic syndromes of medicinal or toxic origin) because it improves neuromuscular transmission by increasing the entry of cellular calcium, which promotes the release of acetylcholine in the nerve endings (Murray N. M. et al., *Neurology* 1981, 31, 265-27; McEvoy K. M. et al., *N. Engl. J. Med.* 1989, 321, 1567-1571). The ability of 3,4-diaminopyridine to increase the release of acetylcholine in the nerve endings also makes it possible to envisage its use in improving the cognitive functions during aging (U.S. Pat. No. 4,386,095). 3,4-Diaminopyridine may also be useful for the symptomatic treatment of fatigue related to a neurological pathology, such as, for example, multiple sclerosis (Bever et al., *Annals of Neurology* 1990, 27, 421-427 and Sheean et al., *Brain* 1998, 121, 967-975). Finally the use of 3,4-diaminopyridine has been described for the treatment of diseases affecting motor neuron cells, such as acute infectious poliomyelitis and its effects, Creutzfeldt-Jakob syndrome, some toxic and nutritional disorders, such as those related to vitamin B deficiency, degeneration of motor neurons as a result of exposure to certain compounds, such as aluminum, or degenerative diseases, such as amyotrophic lateral sclerosis, primary lateral sclerosis, pre-senile dementia with attack on motor neurons, spinal muscular atrophies, olivoponto-cerebellar atrophy, Joseph's disease, Parkinson's disease, Huntington's chorea or Pick's disease.

Lambert-Eaton myasthenic syndrome (LEMS) is a rare autoimmune disease with the primary symptom of proximal muscle weakness. Muscle weakness resulting from LEMS is caused by auto-antibodies to voltage-gated calcium channels leading to a reduction in the amount of acetylcholine released from nerve terminals. The first clinical symptom of LEMS is typically proximal muscle weakness that may impact ability to walk and climb stairs.

The treatment options available for patients with LEMS can be classified into 3 main categories, each targeting different aspects of the pathogenesis of the disease: 1) anti-tumor treatment (e.g., chemotherapy) in the paraneoplastic form, 2) immunologic treatments (e.g., intravenous immunoglobulin (IVIG), plasma exchange, immunoadsorption, prednisone, azathioprine) suppressing the autoimmune reaction, and 3) symptomatic treatment (e.g., pyridostigmine, amifampridine). The treatment strategies may include the above options individually or in different combinations; however, there are no data from published randomized controlled trials to support the use of the various combinations.

The applicants have demonstrated that the pharmacokinetic profile of orally administered 3,4-DAP is highly variable between patients with up to 10-fold differences in maximum observed plasma concentration ($C_{max}$), area under the plasma concentration-time curve (AUC) and apparent plasma terminal elimination half-life ($t_{1/2}$) between subjects. Similar variability has been demonstrated in the literature (Wirtz et al., *Nature* 2009, 86(1), 44-48; Bever et al., *Ann Neurol* 1990, 27, 421-427; and Bever et al., *Neurology* 1996, 47, 1457-1462). However, no rationale has been provided previously for this variability. Further, no methods have been described in the literature for determining how a patient will respond to 3,4-DAP without actually administering 3,4-DAP with the attendant risks of side effects and lack of efficacy. This variability suggests that the method of administering and/or amount of 3,4-DAP should be adjusted to each patient. Thus, there exists a need for alternative and improved methods of administering 3,4-diaminopyridine.

SUMMARY

Provided herein are methods of determining NAT acetylation status of a subject with a 3,4-DAP-sensitive disease, methods of selecting a dose of 3,4-DAP or a pharmaceutically acceptable salt thereof adjusted to a subject's acetylation status, methods of administering 3,4-diaminopyridine or a pharmaceutically acceptable salt thereof to a patient in need thereof, and methods of treating 3,4-DAP sensitive diseases, in a manner that improves or maximizes its efficacy, and/or improves or maximizes its oral bioavailability, and/or improves or optimizes the consistency of oral bioavailability from one administration to the next, and/or decreases the frequency or severity of adverse events. Such methods can be applied in the treatment of any 3,4-diaminopyridine-responsive disorder, including, but not limited to, myasthenia gravis and myasthenic syndromes (including Lambert-Eaton myasthenic syndrome, congenital myasthenia, and myasthenic syndromes of medicinal or toxic origin), multiple sclerosis, improving the cognitive functions during aging, treatment of fatigue related to a neurological pathology, diseases affecting motor neuron cells, such as acute infectious poliomyelitis and its effects, Creutzfeldt-Jakob syndrome, some toxic and nutritional disorders, such as those related to vitamin B deficiency, degeneration of motor neurons as a result of exposure to certain compounds, such as aluminum, or degenerative diseases, such as amyotrophic lateral sclerosis, primary lateral sclerosis, pre-senile dementia with attack on motor neurons, spinal muscular atrophies, olivoponto-cerebellar atrophy, Joseph's disease, Parkinson's disease, Huntington's chorea or Pick's disease. The methods provided herein advantageously allow better control of clinical symptoms, e.g., fewer and/or less severe adverse events or other clinical parameters.

As used herein, 3,4-DAP refers to 3,4-diaminopyridine and amifampridine. The term 3,4-DAP as used herein includes a pharmaceutically acceptable salt of 3,4-diaminopyridine, unless the context dictates otherwise. 3-N-AcDAP, 3-N-acetyl DAP, and 3-N-acetyl amifampridine refer to N-(4-aminopyridin-3-yl)acetamide.

In a first aspect, provided herein is a method comprising administering 3,4-diaminopyridine or a pharmaceutically acceptable salt thereof, to a human in need thereof, and informing said human that the frequency and/or severity of side effect(s) of said 3,4-diaminopyridine or pharmaceutically acceptable salt thereof are decreased when it is ingested with food compared to when ingested without food.

In a second aspect, provided herein is a method comprising determining whether a subject is a slow acetylator or fast acetylator of 3,4-DAP.

In a third aspect, provided herein is a method of selecting a dose of 3,4-DAP or a pharmaceutically acceptable salt thereof in an amount that is adjusted to the subject's acetylator status.

In a fourth aspect, provided herein is a method of administering a dose of 3,4-DAP or a pharmaceutically acceptable salt thereof in an amount that is adjusted to the subject's acetylator status.

In a fifth aspect, provided herein is a method of selecting a dose of 3,4-DAP or a pharmaceutically acceptable salt thereof for a subject who is a fast acetylator and informing the fast acetylator to take said 3,4-DAP without food.

In a sixth aspect, provided herein is a method of treating a 3,4-DAP-sensitive disease comprising determining whether a subject is a slow acetylator or fast acetylator; selecting a dose of 3,4-DAP or a pharmaceutically acceptable salt thereof based on the subject's acetylator status; and administering the dose of 3,4-DAP to the subject in need thereof.

In a seventh aspect, provided herein is a method of treating a 3,4-DAP-sensitive disease comprising administering a dose of 3,4-DAP to the subject in need thereof in an amount adjusted to the subject's acetylator status.

In an eighth aspect, provided herein is a method of treating a 3,4-DAP-responsive disorder with 3,4-DAP or a pharmaceutically acceptable salt thereof in a subject who is a fast acetylator in a dose of 80 mg or more per day.

In a ninth aspect, provided herein is a method of treating a 3,4-DAP-responsive disorder with 3,4-DAP or a pharmaceutically acceptable salt thereof in combination with an inhibitor of an NAT enzyme.

BRIEF DESCRIPTION OF THE DRAWINGS

FIG. 5 shows the $C_{max}$ and AUC ratio of the metabolite N-(4-aminopyridin-3-yl)acetamide to 3,4-diaminopyridine in rats after the first dose in a fasted state for the experiment described in Example 4.

FIG. 10 depicts mean plasma concentrations (+SD) of 3,4-DAP following oral administration of 3,4-DAP phosphate to all subjects in a fed or fasted state for the clinical trial described in Example 10.

FIG. 11 depicts mean PK parameters for 3,4-DAP in fed and fasted subjects following administration of oral 3,4-DAP phosphate for the clinical trial described in Example 10.

FIG. 13 depicts mean pharmacokinetic parameters for N-(4-aminopyridin-3-yl)acetamide in fed and fasted subjects following administration of oral 3,4-DAP phosphate for the clinical trial described in Example 10.

FIG. 14 depicts mean, maximal and minimal urinary excretion of 3,4-DAP and N-(4-aminopyridin-3-yl)acetamide in fed and fasted subjects receiving oral 3,4-DAP phosphate for the clinical trial described in Example 10.

FIG. 15 shows the schedule of events for the evaluation of safety for the clinical trial described in Example 10.

FIG. 16 depicts mean PK parameters (arithmetic values) for treatment groups A and B in the clinical trial described in Example A.

FIG. 17 depicts mean values of 3,4-DAP phosphate or free base (ng/mL) at time sampling for the clinical trial described in Example A.

FIG. 19a depicts 90% CI for AUCs and $C_{max}$ free base/phosphate salt ratio for the clinical trial described in Example A.

FIG. 19b depicts time to reach $C_{max}$ for the clinical trial described in Example A.

FIG. 20 depicts concentration response data for 3,4-DAP Phosphate and N-(4-aminopyridin-3-yl)acetamide HCl in CHO Cells Transiently Transfected with hKv1.7 for the experiment described in Example 5.

FIG. 21a and FIG. 21b depict concentration response data for 3,4-DAP phosphate and N-(4-aminopyridin-3-yl)acetamide HCl in CHO or HEK293 Cells transiently transfected with hKv1.1, hKv1.2, hKv1.3, hKv1.4, or hKv1.5 for the experiment described in Example 6.

FIGS. 24a and 24b depict mean pharmacokinetic parameters (±SD) of 3,4-DAP and 3-N-acetyl (5-30 mg 3,4-DAP base equivalents) in healthy subjects after single oral doses of Firdapse® in slow and fast acetylator phentoypes for the trial described in Example 18, Part 1.

FIG. 25 depicts mean plasma concentration-time profiles of BMN125 after single oral doses of Firdapse® at 5, 10, 20 and 30 mg (base equivalents) in healthy subjects with slow and fast acetylator phenotypes for the trial described in Example 18, Part 1.

FIG. 28 depicts treatment-emergent drug-related adverse events by treatment and phenotype for Part 1 of the Study in Example 18.

FIG. 29 depicts treatment-emergent drug-related adverse events by treatment and phenotype for Part 2 of the study in Example 18.

DETAILED DESCRIPTION

Provided herein are methods of administering a purified preparation of 3,4-diaminopyridine (3,4-DAP, amifampridine) including a pharmaceutically acceptable salt thereof. The Applicants have found that the PK profile of administered 3,4-DAP is highly variable between patients with up to 10-fold differences in maximum observed plasma concentration ($C_{max}$), area under the plasma concentration-time curve (AUC) and apparent plasma terminal elimination half-life ($t_{1/2}$) between subjects (Example A, FIG. 16). The Applicants have discovered that the variability between patients is explained by the surprising metabolic disposition of amifampridine through N-acetyl transferases (NAT) to form the major 3-N-acetyl metabolite, depicted below

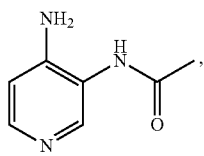

3-N-acetyl-3,4-diaminopyridine and herein identified for the first time.

NAT enzymes are present in most mammalian species. However, dogs lack NAT and acetylation pathways entirely. In mouse and rat, NAT1, NAT2, NAT3 subtypes are present. In humans, NAT1 and NAT2 subtypes are present. NAT2 is located primarily in liver and intestine and NAT1 is ubiquitous and present in virtually all tissues. NAT enzymes are highly polymorphic in humans, and individuals can be classified as slow and rapid acetylators (Casarett & Doull's Toxicology, The Basic Science of Poisons 7th Ed. (2008) Chapter 6: Biotransformation of Xenobiotics. pp. 278-282). The polymorphism of the NAT enzymes is well characterized in the Caucasian population, where the slow acetylator phenotype is present in 50-59% of Caucasians (Casarett & Doull's Toxicology, The Basic Science of Poisons 7th Ed. (2008) Chapter 6: Biotransformation of Xenobiotics. pp. 278-282). Acetylator subtype varies considerably with ethnicity (Casarett & Doull's Toxicology, The Basic Science of Poisons 7th Ed. (2008) Chapter 6: Biotransformation of Xenobiotics. pp. 278-282). An individual's acetylator phenotype can be determined by using procedures described in Example 15 and Example 15a. An individual's acetylator genotype can be determined by using procedures described in Example 16. For isoniazid, a half life of 1 to 2 hours indicates a rapid acetylator and a half life of 2 to 5 hours indicates a slow acetylator. Acetylator phenotype affects the overall PK parameters and disposition of amifampridine in individual humans. In particular, high $C_{max}$ in animals (including, but not limited to fasted rats) has correlated to toxicity.

Figure 1:
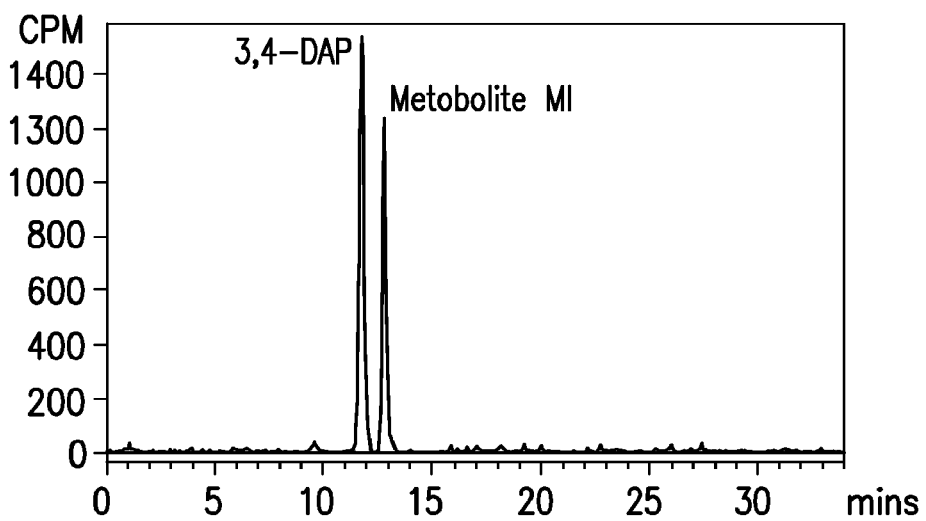
FIG. 1 shows concentrations of 3,4-diaminopyridine and its metabolite N-(4-aminopyridin-3-yl)acetamide in rat hepatocytes for the experiment described in Example 1.
Figure 2:
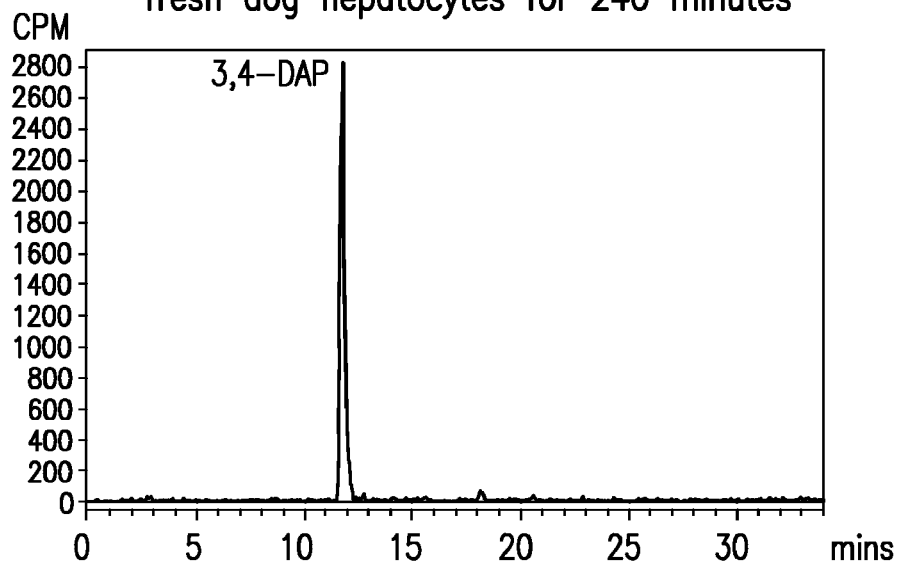
FIG. 2 shows concentrations of 3,4-diaminopyridine in dog hepatocytes for the experiment described in Example 2.
Figure 3:
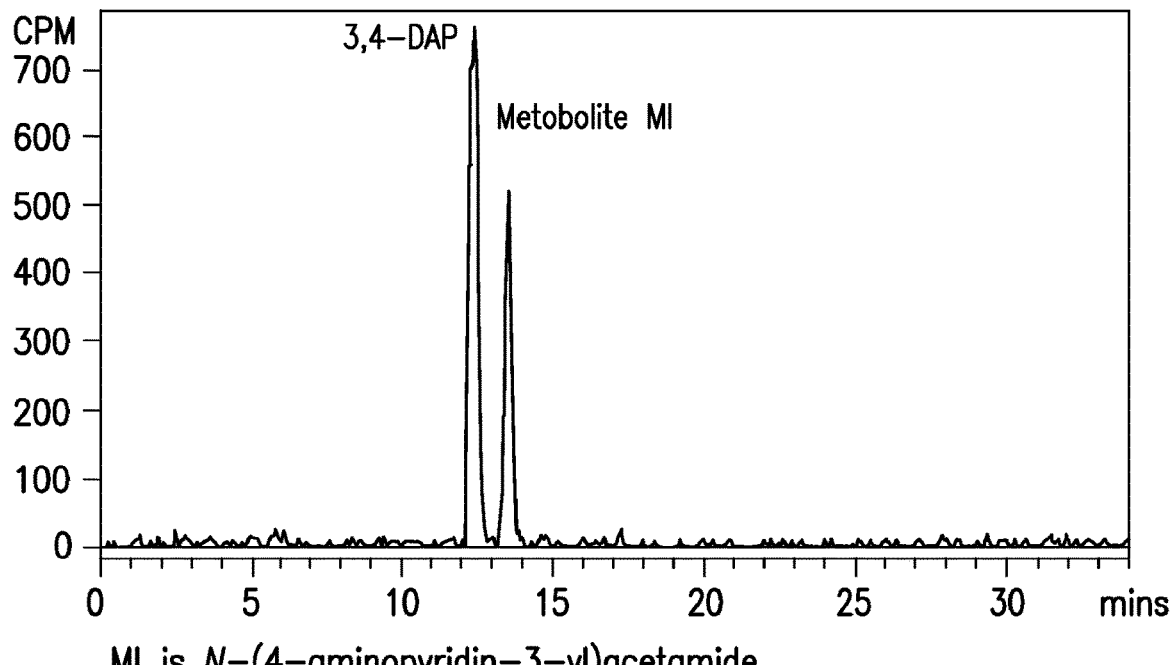
FIG. 3 shows concentrations of 3,4-diaminopyridine and its metabolite N-(4-aminopyridin-3-yl)acetamide in human hepatocytes for the experiment described in Example 3.

In vitro comparative metabolism studies conducted in hepatocytes demonstrated the formation of a single major acetylated amifampridine metabolite in rat (extensive) and human hepatocytes (variable) (Examples 1 and 3, respectively and FIGS. 1 and 3, respectively), but not dog (Example 2 and FIG. 2). This is consistent with the lack of the N-acetyl transferase (NAT) enzyme and acetylation pathway in dog. Thus, the dog with its lack of amifampridine metabolism (corresponding to the slow human acetylator population) and the rat with its rapid rate of metabolism (corresponding to the fast human acetylator population) are representative models for parent and metabolite exposure in humans. As indicated in FIGS. 1 and 3, $^{14}$C-3,4-diaminopyridine phosphate rat and human hepatocytes metabolism studies indicate conversion to N-(4-aminopyridin-3-yl)acetamide. No conversion of 3,4-DAP to its metabolite was seen in dog hepatocytes (FIG. 2). In multiple human hepatocyte donor incubations variable metabolism/conversion N-(4-aminopyridin-3-yl)acetamide is observed (FIG. 3, for example).

In a rat pharmacokinetic study (Example 4, FIGS. 4 and 5), it was demonstrated that the N-(4-aminopyridin-3-yl) acetamide metabolite, the major circulating metabolite, is more abundant than 3,4-DAP and is a model for rapid metabolism. Exposure to N-(4-aminopyridin-3-yl)acetamide demonstrates a dose related dependence and a first pass effect (liver). In vitro metabolic studies in rat hepatocytes (Example 1) correctly predict in vivo observations. Additional in vitro pharmacodynamic studies indicate the N-(4-aminopyridin-3-yl)acetamide metabolite is inactive in the evaluated K+ channels (FIGS. 20 and 21).

Figure 7:
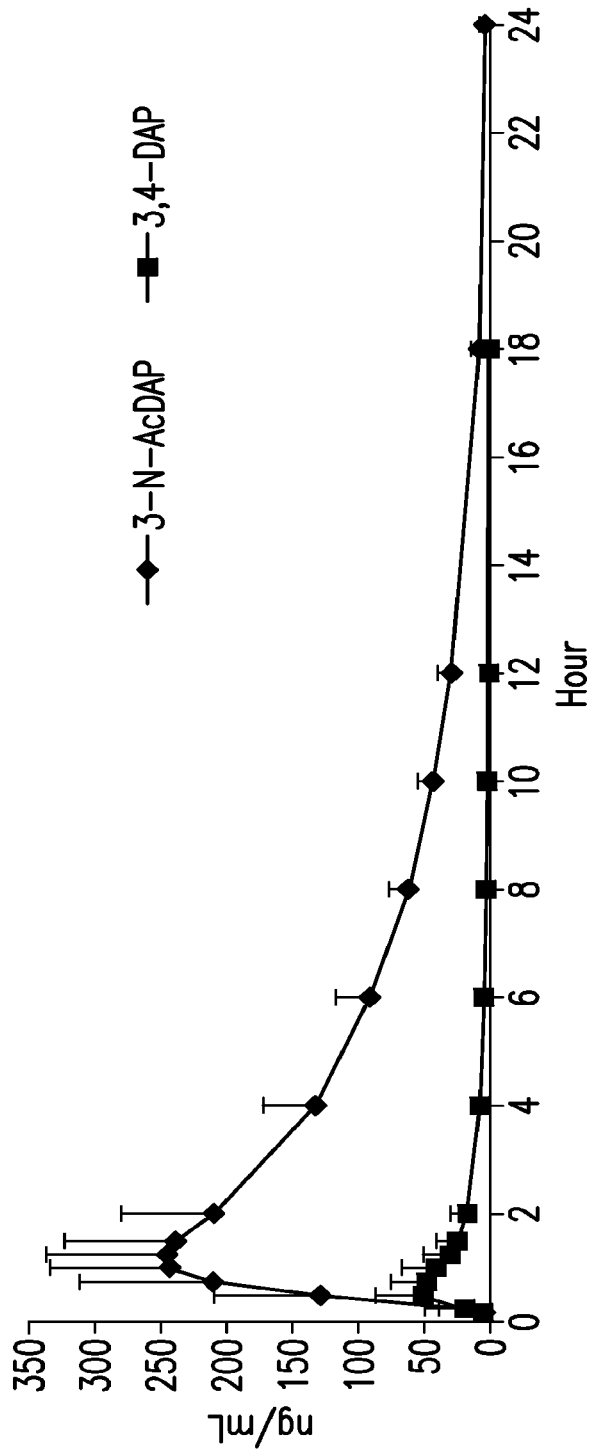
FIG. 7 shows the mean plasma concentrations (+SD) of 3,4-DAP and N-(4-aminopyridin-3-yl)acetamide following oral administration of 3,4-DAP phosphate to all subjects in a fasted state for the clinical trial described in Example 10.
Figure 8:
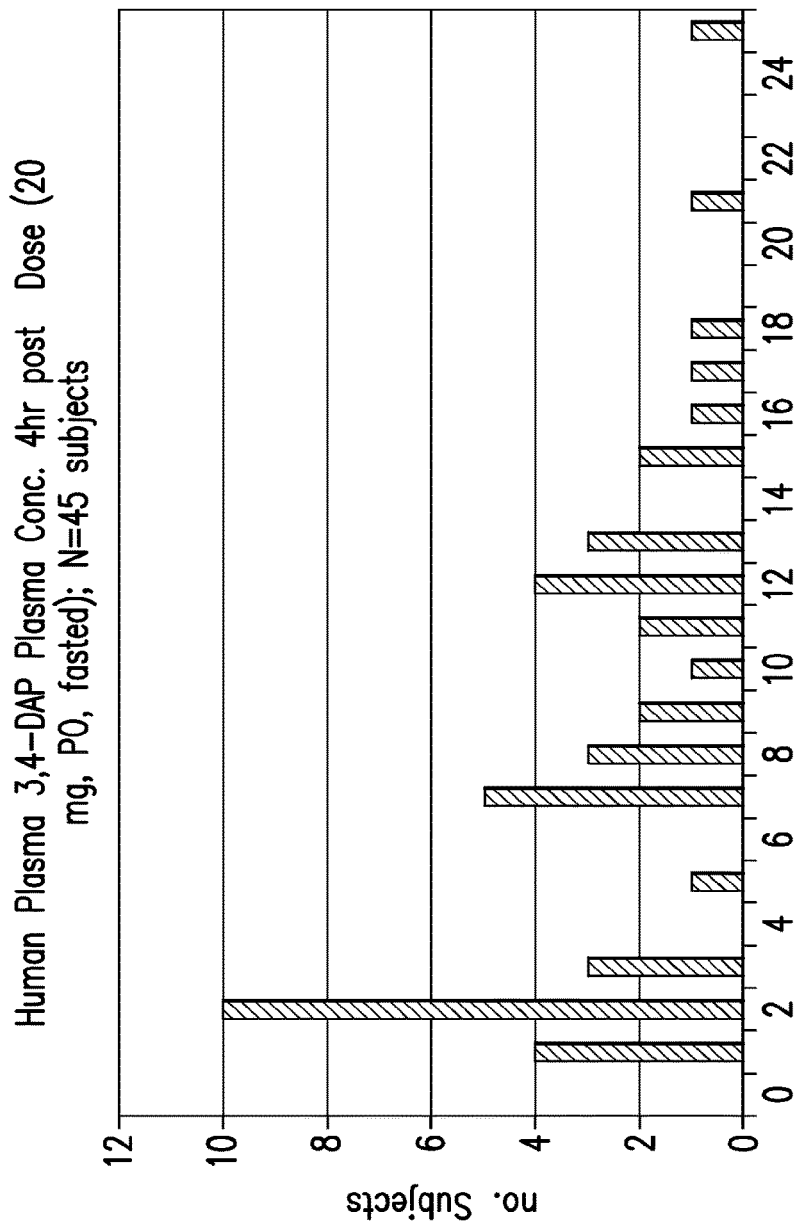
FIG. 8 shows the human plasma 3,4-diaminopyridine plasma concentration at four hours post dose in a fasted state for the clinical trial described in Example 10.

In a human clinical trial (Example 10), N-(4-aminopyridin-3-yl)acetamide concentration in vivo is significantly higher than 3,4-DAP at all time points (FIG. 6, fed state and FIG. 7, fasted state) and with high level of variability (FIG. 8). This is the first demonstration in human that 3,4-diaminopyridine undergoes extensive metabolic conversion to the major circulating metabolite N-(4-aminopyridin-3-yl)acetamide.

Figure 6:
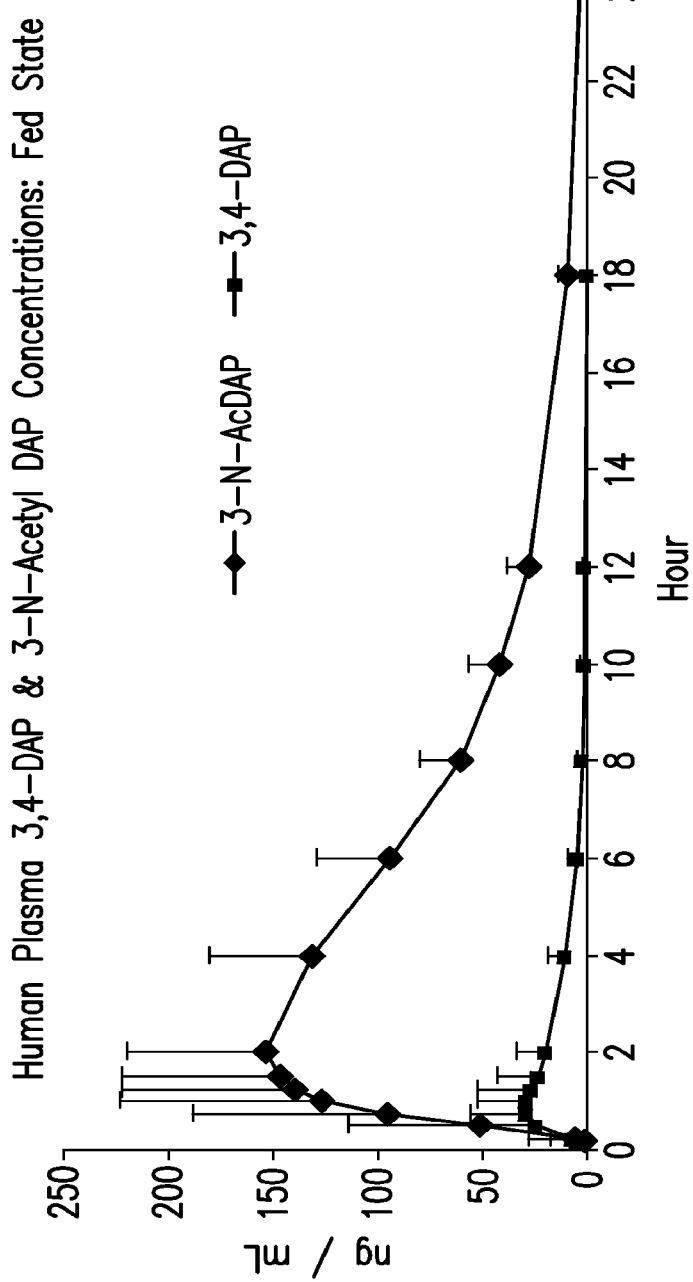
FIG. 6 shows the mean plasma concentrations (+SD) of 3,4-DAP and N-(4-aminopyridin-3-yl)acetamide following oral administration of amifampridine phosphate to all subjects in a fed state for the clinical trial described in Example 10.

FIG. 6 depicts the concentration in vivo of 3,4-DAP and its metabolite N-(4-aminopyridin-3-yl)acetamide in a fed state. FIG. 7 depicts the concentration in vivo of 3,4-DAP and its metabolite N-(4-aminopyridin-3-yl)acetamide in a fasted state. A comparison of FIGS. 6 and 7 demonstrate that administering 3,4-DAP with food reduces the concentration of the compound which reduces the potential for associated side effects.

In the clinical study described in Example 10, the 3,4-DAP plasma levels at 4 hours post dose suggests emerging bimodal distribution by plasma concentration in fasted subjects (FIG. 8). Subjects in this study were not tested to determine whether they were fast or slow metabolizers. Retrospectively, fast acetylators were likely in the region of 0-5 ng/mL 3,4-DAP at 4 hours post dose and slow acetylators were likely in the broad region of 10-26 ng/mL 3,4-DAP at 4 hours post dose. Intermediate acetylators were likely in the region of 5-10 ng/mL at 4 hours post dose. Intermediate acetylators are categorized as fast acetylators.

Figure 9:
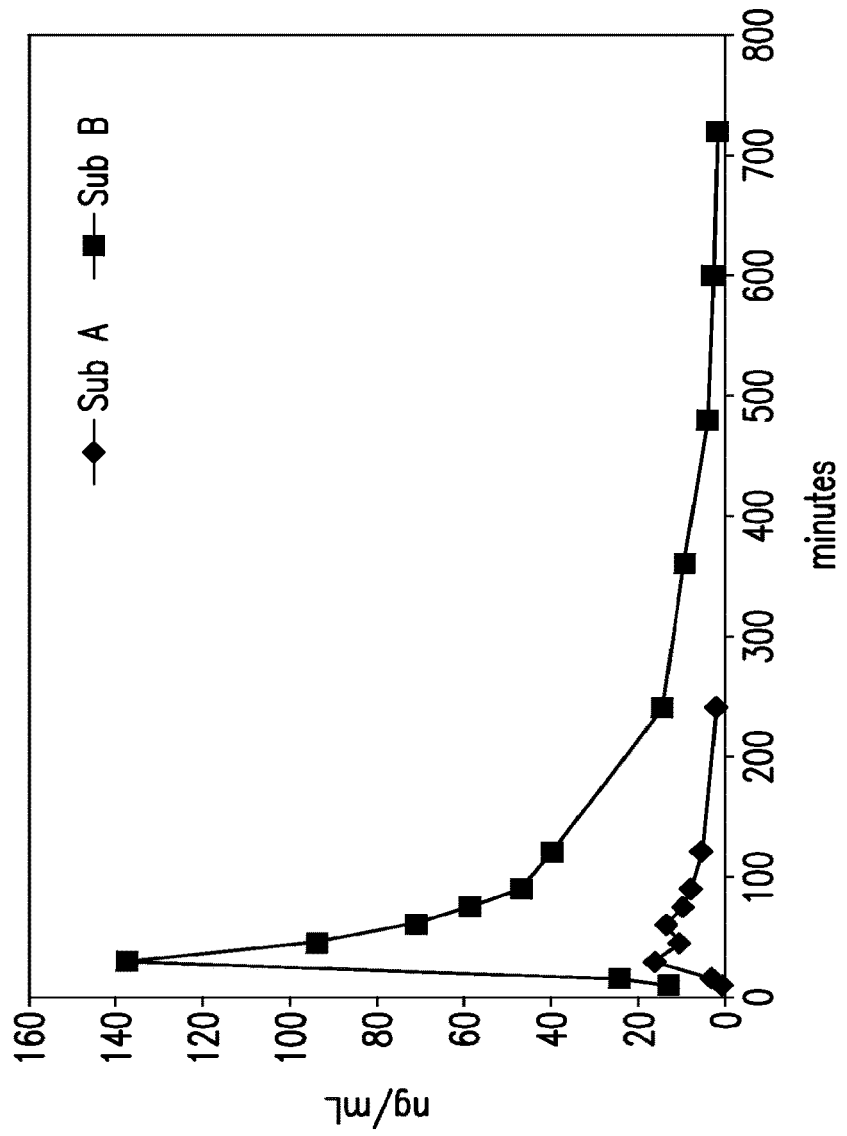
FIG. 9 shows the 3,4-diaminopyridine phosphate exposure in two human patients after a single oral dose in a fasted state for the clinical trial described in Example 10.

Examples of PK for two patients from Example 10 after a single oral dose of 3,4-DAP are depicted in FIG. 9. Subject A was likely to be a fast acetylator with a 3,4-DAP phosphate half life of 74 min and a low $C_{max}$ of 18 ng/mL for measurable 3,4-DAP phosphate levels of up to 4 hours post dose. Subject B was likely to be a slow acetylator with a 3,4-DAP phosphate half life of 152 min and a $C_{max}$ of 138 ng/mL for measurable 3,4-DAP phosphate levels of up to 12 hours post dose. High PK variability poses significant issues for attempting to achieve maximum efficacy and safety. Dosing subject B too often (e.g., more than once a day) and/or with too much drug has the potential for increased side effects. Dosing subject A too infrequently and/or with too little drug (e.g., only once or twice a day) has the potential for reduced or lack of efficacy thus delaying relief for a patient from the symptoms of their disease.

In a second study described in Example 18, it was confirmed that there are slow and fast acetylators of 3,4-DAP. See Table 5 for phenotyping and genotyping data for each subject in Part 1 and 2 of the trial in Example 18 which data categorizes each subject as slow or fast. In Part 1 of the study in Example 18, across each of the single dose groups, the ratio of mean $C_{max}$ values for slow acetylators ranged from 3.5 to 4.5 fold greater than for fast acetylators (FIG. 22 and FIG. 24) demonstrating that there are large differences in metabolism among subjects.

Slow acetylators have higher plasma levels, exaggerated pharmacology, and more severe and/or more frequent adverse events (FIG. 22 through FIG. 29). Slow acetylators of 3,4-diaminopyridine are more likely than fast acetylators to have drug-related adverse events and also have a greater number of drug-related adverse events (Example 18, FIGS. 28 and 29). Fast acetylators have lower plasma levels of 3,4 DAP (FIGS. 25 and 26) and higher levels of the metabolite (FIG. 27), reduced exposure, and the potential for lower or lack of efficacy.

Determining a patient's status as a fast or slow acetylator allows for the optimization of exposure and efficacy and minimization of adverse events and adds significant value for treating a LEMS patient.

EMBODIMENTS

Any of the following embodiments or embodiments within embodiments may be combined with any other embodiment disclosed herein.

For the compositions and methods described herein, exemplary components, and compositional ranges thereof, can be selected from the various examples provided herein.

Other features and advantages of the invention will become apparent from the following detailed description. It should be understood, however, that the detailed description and the specific examples, while indicating embodiments of the invention, are given by way of illustration only, because various changes and modifications within the spirit and scope of the invention will become apparent to those skilled in the art from this detailed description.

In some or any embodiments, the methods disclosed herein can be practiced with 3,4-diaminopyridine or a pharmaceutically acceptable salt thereof or with 4-aminopyridine or a pharmaceutically acceptable salt thereof. A person of ordinary skill in the art would understand that a disease which is sensitive to treatment with 3,4-DAP will also be sensitive to treatment with 4-aminopyridine.

To maximize efficacy in fast acetylators, 3,4-DAP can be taken on an empty stomach (e.g., 1 hour before or 2 hours after a meal) or the dose can be increased and optionally taken with food at the higher dose. To reduce the frequency and/or severity of adverse events, in slow acetylators, 3,4-DAP can be taken with food or the dose can be decreased.

In some or any embodiments, the human is female. In some or any embodiments, the human is female and is told to take 3,4-DAP with food. In some or any embodiments, the human is female and is told she has a greater risk of frequency and/or severity of side effects as compared to a male.

In some or any embodiments, 3,4-DAP is administered at a specified time including but not limited to morning, day, night, same time of the day, and/or one or more times a day.

In some or any embodiments, the disclosed methods also comprise the step of providing to the patient in need thereof a therapeutically effective amount of 3,4-diaminopyridine. The therapeutically effective amount will vary depending on the condition to be treated, and can be readily determined by the treating physician based on improvement in desired clinical symptoms.

In any or all embodiments, the disease or 3,4-DAP-sensitive disease is LEMS, myasthenia gravis, multiple sclerosis, or congenital myasthenia.

In some or any embodiments, 3,4-diaminopyridine is administered as a phosphate salt. In some or any embodiments, 3,4-diaminopyridine is administered as a tartrate salt. In some or any embodiments, 3,4-diaminopyridine is administered as a free base.

Disclosed herein is a method comprising administering 3,4-diaminopyridine or a pharmaceutically acceptable salt thereof, to a human in need thereof, and informing said human that the frequency and/or severity of side effect(s) of said 3,4-DAP or pharmaceutically acceptable salt thereof are decreased when it is ingested with food compared to when ingested without food. In some embodiments or any embodiments, the 3,4-DAP is administered with food and the food is a high-fat, high-calorie meal. In some or any embodiments, the method can be practiced in combination with any of the methods in embodiment 1.

Embodiment 1

In some or any embodiments, the 3,4-DAP is administered shortly following food.

In some or any embodiments, the composition is administered to the patient when the stomach is full, for example, concurrently with ingestion of food, 5 min or less after ingestion of food, 10 min or less after ingestion of food, 30 min or less after ingestion of food, 35 min or less after ingestion of food, 40 min or less after ingestion of food, 45 min or less after ingestion of food, 60 min or less after ingestion of food, 75 min or less after ingestion of food, 90 min or less after ingestion of food, 105 min or less after ingestion of food, or 120 min or less after ingestion of food. In some or any of the above embodiments, the composition is administered to the patient when the stomach is full, for example, concurrently with ingestion of food, 5 min or less after ingestion of food, 10 min or less after ingestion of food, 30 min or less after ingestion of food, 35 min or less after ingestion of food, 40 min or less after ingestion of food, 45 min or less after ingestion of food, or 60 min or less after ingestion of food. In some or any embodiments, the composition is administered to the patient when the stomach is full, for example, concurrently with ingestion of food, 5 min or less after ingestion of food, 10 min or less after ingestion of food, 30 min or less after ingestion of food, or 35 min or less after ingestion of food.

In some or any embodiments, the 3,4-DAP and the food may be ingested at approximately the same time, or the 3,4-DAP may be ingested before or after the food. The period of time between consuming the food and taking 3,4-DAP may be about 5 min or less. For example, 3,4-DAP may be administered before food in an interval of 30 min or less, 25 min or less, 20 min or less, 15 min or less, 10 min or less, or 5 min or less.

In some or any embodiments, the 3,4-DAP is administered with food and the food is a high-fat, high-calorie meal.

In some or any embodiments, there is a decrease in any one, two, three or all of the following parameters when 3,4-DAP is ingested with food compared to when ingested without food: mean plasma concentration, $C_{max}$, $AUC_{(0-t)}$ and/or $AUC_{(0-inf)}$. In exemplary embodiments, the patient is informed that administration of 3,4-diaminopyridine with a meal decreases $C_{max}$ and AUC compared to administration of 3,4-diaminopyridine without food (in a fasting condition). In some embodiments, the relative decrease in $C_{max}$ can be at least about 50%, in another example about 40% or less, in another example by about 35% or less, in another example by about 30% or less, in another example by about 30% or less, in another example by about 25% or less, in another example by about 20% or less, in another example by about 15% or less, in another example by about 10% or less. In some embodiments, the relative decrease in AUC(0-t) can be at least about 50%, in another example about 40% or less, in another example by about 35% or less, in another example by about 30% or less, in another example by about 30% or less, in another example by about 25% or less, in another example by about 20% or less, in another example by about 15% or less, in another example by about 10% or less. In some embodiments, the relative decrease in AUC(0-inf) can be at least about 50%, in another example about 40% or less, in another example by about 35% or less, in another example by about 30% or less, in another example by about 30% or less, in another example by about 25% or less, in another example by about 20% or less, in another example by about 15% or less, in another example by about 10% or less.

In some or any embodiments, the patient is informed that ingestion shortly following a meal results in a decrease in side effect(s). In some or any embodiments, the side effect(s) to be reduced in frequency or severity is described in any of the embodiments or examples, for example the following embodiments.

In some or any embodiments, the side effect(s) to be reduced in frequency or severity is independently selected from a nervous system disorder, a gastrointestinal disorder, general disorder, infection or infestation, skin and subcutaneous tissue disorder, vascular disorder, cardiac disorder, and musculoskeletal and connective tissue disorder.

In some or any embodiments, the frequency of side effect(s) is reduced by about 30-35%. In some or any embodiments, the frequency of side effect(s) is reduced by about at least a third. In some or any embodiments, the frequency of side effect(s) is reduced by about 25-30%. In some or any embodiments, the frequency of side effect(s) is reduced by about 20-25%. In some or any embodiments, the frequency of side effect(s) is reduced by about 15-20%. In some or any embodiments, the frequency of side effect(s) is reduced by about 10-15%. In some or any embodiments, the frequency of side effect(s) is reduced by about 5-10%.

In some or any embodiments, the side effect is a nervous system disorders and is decreased by about at least 30%. In some or any embodiments, the frequency of side effects was reduced by about 25-30%. In some or any embodiments, the frequency of side effects was reduced by about 20-25%. In some or any embodiments, the frequency of side effects was reduced by about 15-20%. In some or any embodiments, the frequency of side effects was reduced by about 10-15%. In some or any embodiments, the frequency of side effects was reduced by about 5-10%. In some or any embodiments, the nervous system disorder that is decreased is paraesthesia, e.g. oral or skin.

In some or any embodiments, the side effect is paraesthesia and the frequency is decreased by at least about 35%, in another example by about 30-35%, in another example by about 25-30%, in another example by about 20-25%, in another example by about 15-20%, in another example by about 15-20%, in another example by 10-15%.

In some or any embodiments, the side effect is dizziness and the frequency is decreased by at least about 60%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is oral headache and the frequency is decreased by at least about 75%, in another example by about 70-75%, in another example by about 65-70%, in another example by about 60-65%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is hypoaesthesia and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is facial hypoaesthesia and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by 35-40%, in another example by 30-35%, in another example by about 25-30%, in another example by about 20-25%, in another example by about 15-20%, in another example by about 10-15%, in another example by about 5-10%.

In some or any embodiments, the side effect is a gastrointestinal disorder and is decreased by at least about 80% amount, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is a nausea and is decreased by at least about 65% amount, in another example by about two thirds, in another example by about 60-65%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is abdominal pain and/or tenderness and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any embodiments, the side effect is diarrhea and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

Phenotyping Methods

Caffeine Methods:

In some or any embodiments, a subject is determined to be a slow or fast acetylator by administering caffeine to the subject, taking a urine sample, and measuring the metabolites of caffeine ("caffeine test"). In some or any embodiments of the caffeine test, 150 mg caffeine is administered. In some or any embodiments of the caffeine test, the following ratio is determined: (AFMU+AAMU)/(AFMU+AAMU+1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments of the caffeine test, a fast acetylator has a ratio of greater than about 0.2, in another example between about 0.2 to about 0.3, and a slow acetylator has a ratio of about 0.2 or less, for example between about 0.1 and about 0.2 (inclusive). In some or any embodiments, the caffeine test is administered substantially as described in Example 15a.

In some or any embodiments, a subject's phenotype is determined substantially as described in Example 15, including any of the cited references, the disclosure of each of which is herein incorporated by reference in its entirety.

In some or any embodiments, a subject's NAT polymorphism phenotype is determined using the caffeine test as described in any embodiments or examples herein.

3,4-DAP Test:

In some or any embodiments, the subject is determined to be a slow or fast acetylator by administering 3,4-DAP, or a pharmaceutically acceptable salt thereof, to the subject and measuring the amount of 3,4-DAP and N-(4-aminopyridin-3-yl)acetamide. In some or any embodiments, the fast acetylator has an $AUC_{0-inf}$ ratio of N-(4-aminopyridin-3-yl)acetamide/3,4-DAP of greater than about 20. In some or any embodiments, a slow acetylator has a ratio of N-(4-aminopyridin-3-yl)acetamide/3,4-DAP of less than about 20. In some or any embodiments, the fast acetylator has an $AUC_{0-inf}$ ratio of N-(4-aminopyridin-3-yl)acetamide/3,4-DAP of greater than about 25. In some or any embodiments, a slow acetylator has a ratio of N-(4-aminopyridin-3-yl)acetamide/3,4-DAP of less than about 15. In some or any embodiments, the fast acetylator has an $AUC_{0-inf}$ ratio of N-(4-aminopyridin-3-yl)acetamide/3,4-DAP of greater than about 30. In some or any embodiments, a slow acetylator has a ratio of N-(4-aminopyridin-3-yl)acetamide/3,4-DAP of less than about 10. In some or any embodiments, the fast acetylator has an $AUC_{0-inf}$ ratio of N-(4-aminopyridin-3-yl)acetamide/3,4-DAP of greater than about 30 when dosed with a single dose of 5-30 mg equivalent of free base. In some or any embodiments, a slow acetylator has a ratio of N-(4-aminopyridin-3-yl)acetamide/3,4-DAP of less than about 10 when dosed with a single dose of 5-30 mg equivalent of free base.

Genotyping Methods

NAT Genotyping Methods: In some or any embodiments, a subject's NAT polymorphism genotype is determined by screening a subject's NAT2 gene using one or both of the following molecular probes: C282T and T341C. In some or any embodiments, the subject's NAT1 gene is examined for one of the following seven SNPs *3, *10, *11, *14, *15, *17. In some or any embodiments, the subject's NAT2 gene is examined for one of the following four SNPs *5, *6, *7, and *14. In some or any embodiments, a subject with no fast alleles is a slow metabolizer. In some or any embodiments, the subject whose genotype includes at least one fast allele is a fast acetylator. In some or any embodiments, the subject whose genotype includes two fast alleles is a fast acetylator. In some or any embodiments, a subject is genotyped substantially according to Table 4. In some or any embodiments, a subject's genotype is determined substantially as described in Example 16.

Embodiment 2

Disclosed herein is a method of treating comprising determining whether a subject is a slow acetylator or fast acetylator; selecting a dose of 3,4-DAP or a pharmaceutically acceptable salt thereof; and administering the dose of 3,4-DAP to the subject in need thereof. In some or any of the above embodiments in embodiment 2, the method further comprises informing said human who is a slow acetylator to take said 3,4-DAP or pharmaceutically acceptable salt thereof with food or informing said human who is a fast acetylator to take said 3,4-DAP or pharmaceutically acceptable salt thereof without food. In some or any of the above embodiments in embodiment 2, the method further comprises informing said human who is a slow acetylator that the frequency and/or severity of side effect(s), as described in any of the embodiments or examples herein, of said 3,4-DAP or pharmaceutically acceptable salt thereof are decreased when it is ingested with food compared to when ingested without food; or informing said human who is a fast acetylator that the efficacy of said 3,4-DAP or pharmaceutically acceptable salt thereof is increased when it is ingested without food compared to when ingested with food. In some or any of the above embodiments in embodiment 2, a subject is determined to be a slow or fast acetylator by performing any of the phenotyping methods as described by any of the embodiments or examples herein. In some or any of the above embodiments in embodiment 2, a subject is determined to be a slow or fast acetylator by determining a subject's genotype as described by any of the embodiments or examples herein. In some or any embodiments in embodiment 2, a subject is determined to be a slow or fast acetylator by administering caffeine to the subject and measuring the metabolites of caffeine. In some or any embodiments in embodiment 2, 150 mg caffeine is administered. In some or any embodiments in embodiment 2, the following ratio is determined: (AFMU+AAMU)/(AFMU+AAMU+1×+1U), wherein AFMU is the concentration of 5-acetylamino-6-formylamino-3-methyluracil, AAMU is the concentration of 5-acetylamino-6-amino-3-methyluracil, 1× is the concentration of 1-methylxanthine; and 1U is the concentration of 1 methylurate. In some or any embodiments in embodiment 2, a fast acetylator has a ratio of greater than about 0.2, in another example between about 0.2 to about 0.3, and a slow acetylator has a ratio of about 0.2 or less, for example between about 0.1 and about 0.2 (inclusive).

Embodiment 3

Disclosed herein is a method comprising a) determining a subject's NAT polymorphism phenotype; b) selecting a dose of 3,4-DAP or a pharmaceutically acceptable salt thereof based on the subject's acetylator status; and c) administering the dose of 3,4-DAP to a subject in need thereof. In some or any of the above embodiments in embodiment 3, the method further comprises informing said human whose phenotype is slow acetylation to take said 3,4-DAP or pharmaceutically acceptable salt thereof with or informing said human whose phenotype is fast acetylation to take said 3,4-DAP or pharmaceutically acceptable salt thereof without food. In some or any of the above embodiments in embodiment 3, the method further comprises informing the subject 1) whose phenotype is slow acetylation that the frequency and/or severity of side effect(s) of said 3,4-DAP or pharmaceutically acceptable salt thereof are decreased when it is ingested with food compared to when ingested without food; or 2) whose phenotype is fast acetylation that the efficacy of said 3,4-DAP or pharmaceutically acceptable salt thereof is increased when it is ingested without food compared to when ingested with food. In some or any of the above embodiments in embodiment 3, a subject's phenotype is determined by performing any of the phenotyping methods as described by any of the embodiments or examples herein. In some or any embodiments in embodiment 3, a subject's phenotype is determined by administering caffeine to the subject and measuring the metabolites of caffeine. In some or any embodiments in embodiment 3, 150 mg caffeine is administered. In some or any embodiments in embodiment 3, the following ratio is determined: (AFMU+AAMU)/(AFMU+AAMU+1×+1U), wherein AFMU is the concentration of 5-acetylamino-6-formylamino-3-methyluracil, AAMU is the concentration of 5-acetylamino-6-amino-3-methyluracil, 1× is the concentration of 1-methylxanthine; and 1U is the concentration of 1 methylurate. In some or any embodiments in embodiment 3, a fast acetylator has a ratio of greater than about 0.2, in another example between about 0.2 to about 0.3, in another example greater than or equal to about 0.3, and a slow acetylator has a ratio of about 0.2 or less, for example between about 0.1 and about 0.2 (inclusive).

Embodiment 4

Disclosed herein is a method comprising a) determining a subject's NAT2 polymorphism genotype; b) selecting a dose of 3,4-DAP or a pharmaceutically acceptable salt thereof based on the number of fast alleles the subject has; and c) administering the dose of 3,4-DAP to a subject in need thereof. In some embodiments or any of the above embodiments in embodiment 4, the method further comprises informing said human to take said 3,4-DAP or pharmaceutically acceptable salt thereof without food if the subject has two fast alleles or with food if the subject has no fast alleles. In some embodiments or any of the above embodiments in embodiment 4, the method further comprises informing the subject a) who has no fast alleles that the frequency and/or severity of side effect(s) of said 3,4-DAP or pharmaceutically acceptable salt thereof are decreased when it is ingested with food compared to when ingested without food; or b) who has two fast alleles that the efficacy of said 3,4-DAP or pharmaceutically acceptable salt thereof is increased when it is ingested without food compared to when ingested with food. In some embodiments or any of the above embodiments in embodiment 4, a subject's NAT2 genotype is determined using a method as described in any of the embodiments or examples herein. In some embodiments or any embodiments in embodiment 4, a subject's NAT2 gene is screened for mutations using one or both of the following molecular probes: C282T and T341C. In some embodiments or any embodiments in embodiment 4, the subject's NAT1 gene is examined for one of the following seven SNPs *3, *10, *11, *14, *15, *17. In some embodiments or any embodiments in embodiment 4, the subject's NAT2 gene is examined for one of the following four SNPs *5, *6, *7, and *14. In some embodiments or any embodiments in embodiment 4, a subject is genotyped substantially according to Table 4.

Embodiment 5

Disclosed herein is a method comprising selecting a dose of 3,4-DAP or a pharmaceutically acceptable salt thereof for a subject who is a fast acetylator; and administering the dose of 3,4-DAP to the subject in need thereof without food. In another embodiment, the dose is selected according to any of the embodiments and examples as described herein.

Embodiment 6

Disclosed herein is a method comprising selecting a dose of 3,4-DAP or a pharmaceutically acceptable salt thereof for a subject who is a slow acetylator; administering the dose of 3,4-DAP to the subject in need thereof with food. In another embodiment, the dose is selected according to any of the embodiment and examples as disclosed herein.

Embodiment 7

Disclosed herein is a method comprising determining whether a subject is a slow acetylator or fast acetylator; and administering 3,4-diaminopyridine (3,4-DAP), comprising administering to a human in need thereof 3,4-DAP or a pharmaceutically acceptable salt thereof in an amount that is adjusted to the subject's acetylator status. In some or any of the above embodiments in embodiment 7, the subject is determined to be a slow or fast acetylator by performing a phenotyping method as described by any of the embodiments or examples herein. In some or any embodiments in embodiment 7, the subject is determined to be a slow or fast acetylator by administering caffeine to the subject and measuring the metabolites of caffeine. In some or any embodiments in embodiment 7, 150 mg caffeine is administered. In some or any embodiments in embodiment 7, the following ratio is determined: (AFMU+AAMU)/(AFMU+ AAMU+1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments in embodiment 7, a fast acetylator has a ratio of greater than about 0.2, in another example between about 0.2 to about 0.3, in another example greater than or equal to about 0.3, and a slow acetylator has a ratio of about 0.2 or less, for example between about 0.1 and about 0.2 (inclusive).

Embodiment 8

Disclosed herein is a method comprising selecting a dose of 3,4-DAP or a pharmaceutically acceptable salt thereof for a subject who is a fast acetylator; and administering the dose of 3,4-DAP to the subject in need thereof without food. In another embodiment, the dose is selected according to any of the embodiments and examples as described herein.

Embodiment 9

Disclosed herein is a method comprising determining whether a subject is a slow acetylator or fast acetylator; selecting a dose of 3,4-DAP or a pharmaceutically acceptable salt thereof in an amount that is adjusted to the subject's acetylator status; and administering the dose of 3,4-DAP to the subject in need thereof. In some or any of the above embodiments in embodiment 9, the subject is determined to be a slow or fast acetylator by performing a phenotyping method as described by any of the embodiments or examples herein. In some or any embodiments in embodiment 9, the subject is determined to be a slow or fast acetylator by administering caffeine to the subject and measuring the metabolites of caffeine. In some or any embodiments in embodiment 9, 150 mg caffeine is administered. In some or any embodiments in embodiment 9, the following ratio is determined: (AFMU+AAMU)/(AFMU+AAMU+1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments in embodiment 9, a fast acetylator has a ratio of greater than about 0.2, in anther example between about 0.2 to about 0.3, in another example greater than or equal to about 0.3, and a slow acetylator has a ratio of about 0.2 or less, for example between about 0.1 and about 0.2 (inclusive).

Embodiment 10

Disclosed herein is a method of determining whether a subject who has a 3,4-DAP-sensitive disease is a slow or fast acetylator. In some or any embodiments of embodiment 10, the subject is determined to be a slow or fast acetylator by performing a phenotyping method as described by any of the embodiments or examples herein. In some or any embodiments of embodiment 10, the subject is determined to be a slow or fast acetylator by administering caffeine to the subject and measuring the metabolites of caffeine. In some or any embodiments, the slow acetylator has a ratio of caffeine metabolites of about 0.2 or less as calculated with the following formula: (AFMU+AAMU)/(AFMU+AAMU+ 1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments, the fast acetylator has a ratio of caffeine metabolites of greater than about 0.2, in another example between about 0.2 to about 0.3, in another example greater than or equal to about 0.3, as calculated with the following formula: (AFMU+AAMU)/(AFMU+AAMU+1x+1U). In some or any embodiments of embodiment 10, the subject is determined to be a slow or fast acetylator by determining the subject's NAT polymorphism genotype using methods as described in any of the embodiments or examples herein. In some or any embodiments, the fast acetylator has two fast alleles. In some of any embodiments, the slow acetylator has no fast alleles. In some or any embodiments, a subject's NAT2 gene is screened for mutations using one or both of the following molecular probes: C282T and T341C.

Embodiment 11

Disclosed herein is a method of treating a 3,4-DAP-sensitive disease comprising determining whether a subject is a slow acetylator or fast acetylator; selecting a dose of 3,4-DAP or a pharmaceutically acceptable salt thereof in an amount that is adjusted to the subject's acetylator status; and administering the dose of 3,4-DAP to the subject in need thereof.

Embodiment A

Provided herein is a method of determining whether a subject who has a 3,4-DAP-sensitive disease is a slow or fast acetylator. In some or any embodiments, the subject is determined to be a slow or fast acetylator by determining a subject's phenotype using one of the phenotyping methods as described in any of the embodiments or examples herein including any of the references which are herein are incorporated by reference, in another example by administering the caffeine test as described by any of the embodiments or examples herein, for example in Example 15a. In some or any embodiments, the subject is determined to be a slow or fast acetylator by administering caffeine to to the subject and measuring the metabolites of caffeine. In some or any embodiments, the slow acetylator has a ratio of caffeine metabolites of about 0.2 or less as calculated with the following formula: (AFMU+AAMU)/(AFMU+AAMU+ 1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments, the fast acetylator has a ratio of caffeine metabolites of greater than about 0.2 as calculated with the following formula: (AFMU+AAMU)/(AFMU+AAMU+1x+1U), wherein AFMU is the concentration of 5-acetylamino-6-formylamino-3-methyluracil, AAMU is the concentration of 5-acetylamino-6-amino-3-methyluracil, 1x is the concentration of 1-methylxanthine; and 1U is the concentration of 1 methylurate. In some or any embodiments, the subject is determined to be a slow or fast acetylator by determining the subject's NAT polymorphism genotype using any one of the genotyping methods as described in any of the embodiments and examples including any references which are herein are incorporated by reference. In some or any embodiments, the subject's genotype is determined using one or both of the molecular probes C282T and T341C. In some or any embodiments, the subject whose genotype includes no fast alleles is a slow acetylator. In some or any embodiments, the subject whose genotype includes at least one fast allele is a fast acetylator. In some or any embodiments, the subject whose genotype includes two fast alleles is a fast acetylator. In some or any embodiments, the subject is determined to be a slow or fast acetylator by administering the 3,4-DAP test. In some or any embodiments, the subject is determined to be a slow or fast acetylator by administering 3,4-DAP, or a pharmaceutically acceptable salt thereof, to the subject and measuring the amount of 3,4-DAP and N-(4-aminopyridin-3-yl)acetamide. In some or any embodiments, the fast acetylator has an $AUC_{0-inf}$ ratio of N-(4-aminopyridin-3-yl)acetamide/3,4-DAP of greater than about 20. In some or any embodiments, a slow acetylator has a ratio of N-(4-aminopyridin-3-yl)acetamide/3,4-DAP of less than about 20. In some or any embodiments, the fast acetylator has an $AUC_{0-inf}$ ratio of N-(4-aminopyridin-3-yl)acetamide/3,4-DAP of greater than about 25. In some or any embodiments, a slow acetylator has a ratio of N-(4-aminopyridin-3-yl)acetamide/3,4-DAP of less than about 15. In some or any embodiments, the fast acetylator has an $AUC_{0-inf}$ ratio of N-(4-aminopyridin-3-yl)acetamide/3,4-DAP of greater than about 30. In some or any embodiments, a slow acetylator has a ratio of N-(4-aminopyridin-3-yl)acetamide/3,4-DAP of less than about 10. In some or any embodiments, the fast acetylator has an $AUC_{0-inf}$ ratio of N-(4-aminopyridin-3-yl)acetamide/3,4-DAP of greater than about 30 when dosed with a single dose of 5-30 mg equivalent of free base. In some or any embodiments, a slow acetylator has a ratio of N-(4-aminopyridin-3-yl)acetamide/3,4-DAP of less than about 10 when dosed with a single dose of 5-30 mg equivalent of free base.

Embodiment B

Disclosed herein is a method which comprises selecting a dose of 3,4-DAP or a pharmaceutically acceptable salt thereof in an amount that is adjusted to the subject's acetylator status which method optionally further comprises any of the embodiments in Embodiment A. In some or any embodiments, for example any of embodiment A, the dose is selected to achieve $C_{max}$ (maximum plasma concentration) of 3,4-DAP of about 15 ng/mL or less about 20 ng/mL or less, about 25 ng/mL or less, about 30 ng/mL or less, about 35 ng/mL or less, about 40 ng/mL or less, about 45 ng/mL or less, about 50 ng/mL or less, about 55 ng/mL or less, about 60 ng/mL or less, about 65 ng/mL or less, about 70 ng/mL or less, about 75 ng/mL or less, about 80 ng/mL or less, about 85 ng/mL or less, or about 90 ng/mL or less. In some or any embodiments, for example any of embodiment A, the dose is selected to achieve $C_{max}$ of 3,4-DAP of about 25 ng/mL or less, about 30 ng/mL or less, about 35 ng/mL or less, about 40 ng/mL or less, about 45 ng/mL or less, about 50 ng/mL or less, about 55 ng/mL or less, or about 60 ng/mL or less. In some or any embodiments, for example any of embodiment A, the dose is selected to achieve $C_{max}$ of 3,4-DAP of about 40 ng/mL or less, about 45 ng/mL or less, about 50 ng/mL or less, or about 55 ng/mL or less. In some or any embodiments, for example any of embodiment A, the dose is selected to achieve $C_{max}$ of 3,4-DAP of less than or equal to about 50 ng/mL and greater than or equal to about 10 ng/mL. In some or any embodiments, for example any of embodiment A, the dose is selected to achieve $C_{max}$ of 3,4-DAP of less than or equal to about 50 ng/mL and greater than or equal to about 15 ng/mL. In some or any embodiments, for example any of embodiment A, the dose is selected to achieve $C_{max}$ of 3,4-DAP of less than or equal to about 50 ng/mL and greater than or equal to about 20 ng/mL. In some or any embodiments, for example any of embodiment A, the dose is selected to achieve $C_{max}$ of 3,4-DAP of less than or equal to about 40 ng/mL and greater than or equal to about 10 ng/mL. In some or any embodiments, for example any of embodiment A, the dose is selected to achieve $C_{max}$ of 3,4-DAP of less than or equal to about 40 ng/mL and greater than or equal to about 15 ng/mL. In some or any embodiments, for example any of embodiment A, the dose is selected to achieve $C_{max}$ of 3,4-DAP of less than or equal to about 40 ng/mL and greater than or equal to about 20 ng/mL. In some or any embodiments, for example any of embodiment A, the dose is selected to achieve $C_{max}$ of 3,4-DAP of less than or equal to about 35 ng/mL and greater than or equal to about 25 ng/mL. In some or any embodiments, for example any of embodiment A, the dose is selected to achieve $C_{max}$ of 3,4-DAP of about 30 ng/mL. In another embodiment, any embodiments A can be practiced with any of embodiments B.

Embodiment C

In some or any embodiments, disclosed herein is a method which comprises administering the dose of 3,4-DAP or a pharmaceutically acceptable salt thereof which method optionally further comprises any of the embodiments in embodiment A and/or B. In some or any embodiments, for example any of embodiment A and/or B, the dose is administered to a slow acetylator with food and to a fast acetylator without food. In another embodiment, any embodiment of embodiments A and/or B can be practiced with any of embodiments C.

Embodiment D

In some or any embodiments, disclosed herein is a method which comprises informing said subject who is a slow acetylator to take said 3,4-DAP or a pharmaceutically acceptable salt thereof with food or informing said subject who is a fast acetylator to take said 3,4-DAP or pharmaceutically acceptable salt thereof without food which method optionally further comprises any of the embodiments in embodiment A, B, and/or C. In some or any embodiments, for example any of embodiment A, B and/or C, the method comprises informing said subject who is a slow acetylator that the frequency and/or severity of side effect(s) of said 3,4-DAP or pharmaceutically acceptable salt thereof are decreased when it is ingested with food compared to when ingested without food; or informing said subject who is a fast acetylator that efficacy of said 3,4-DAP or pharmaceutically acceptable salt thereof is increased when it is ingested without food compared to when ingested with food. In another embodiment, any embodiment of embodiments A, B, and/or C can be practiced with any of embodiments D.

Embodiment E

In some or any embodiments, for example any of embodiment C and/or D, the food is a high-fat, high-calorie meal.

In another embodiment, any embodiment of embodiments C and/or D can be practiced with any of embodiments E.

Embodiment F

In some or any embodiments, for example any of embodiment D and/or E, the slow acetylator is informed that the frequency of side effect(s) is decreased by about 30% when ingested with food. In another embodiment, any embodiment of embodiments D and/or E can be practiced with any of embodiments F.

Embodiment G

In some or any embodiments, for example any of embodiment D, E and/or F, at least one side effect is a nervous system disorder. In some or any embodiments, for example any of embodiment D, E and/or F, at least one side effect is gastrointestinal disorder. In another embodiment, any embodiment of embodiments D, E, and/or F can be practiced with any of embodiments G.

Embodiment H

Provided herein is a method of selecting a dose of 3,4-DAP or a pharmaceutically acceptable salt thereof in an amount that is adjusted to the subject's acetylator status. In some or any embodiments, the dose is selected to achieve $C_{max}$ of 3,4-DAP of about 15 ng/mL or less about 20 ng/mL or less, about 25 ng/mL or less, about 30 ng/mL or less, about 35 ng/mL or less, about 40 ng/mL or less, about 45 ng/mL or less, about 50 ng/mL or less, about 55 ng/mL or less, about 60 ng/mL or less, about 65 ng/mL or less, about 70 ng/mL or less, about 75 ng/mL or less, about 80 ng/mL or less, about 85 ng/mL or less, or about 90 ng/mL or less. In some or any embodiments, the dose is selected to achieve $C_{max}$ of 3,4-DAP of about 25 ng/mL or less, about 30 ng/mL or less, about 35 ng/mL or less, about 40 ng/mL or less, about 45 ng/mL or less, about 50 ng/mL or less, about 55 ng/mL or less, or about 60 ng/mL or less. In some or any embodiments, the dose is selected to achieve $C_{max}$ of 3,4-DAP of about 40 ng/mL or less, about 45 ng/mL or less, about 50 ng/mL or less, or about 55 ng/mL or less. In some or any embodiments, the dose is selected to achieve $C_{max}$ of 3,4-DAP of less than or equal to about 50 ng/mL and greater than or equal to about 10 ng/mL. In some or any embodiments, the dose is selected to achieve $C_{max}$ of 3,4-DAP of less than or equal to about 50 ng/mL and greater than or equal to about 15 ng/mL. In some or any embodiments, the dose is selected to achieve $C_{max}$ of 3,4-DAP of less than or equal to about 50 ng/mL and greater than or equal to about 20 ng/mL. In some or any embodiments, the dose is selected to achieve $C_{max}$ of 3,4-DAP of less than or equal to about 40 ng/mL and greater than or equal to about 10 ng/mL. In some or any embodiments, the dose is selected to achieve $C_{max}$ of 3,4-DAP of less than or equal to about 40 ng/mL and greater than or equal to about 15 ng/mL. In some or any embodiments, the dose is selected to achieve $C_{max}$ of 3,4-DAP of less than or equal to about 40 ng/mL and greater than or equal to about 20 ng/mL. In some or any embodiments, the dose is selected to achieve $C_{max}$ of 3,4-DAP of less than or equal to about 35 ng/mL and greater than or equal to about 25 ng/mL. In some or any embodiments, the dose is selected to achieve $C_{max}$ of 3,4-DAP of about 30 ng/mL. In some or any embodiments, the method further comprises administering the dose of 3,4-DAP or a pharmaceutically acceptable salt thereof. In some or any embodiments, the dose is administered to a slow acetylator with food and to a fast acetylator without food. In some or any embodiments, the food is a high-fat, high-calorie meal. In some or any embodiments, the subject is female.

Embodiment J

Provided herein is a method of administering a dose of 3,4-DAP or a pharmaceutically acceptable salt thereof in an amount that is adjusted to the subject's acetylator status. In some or any embodiments, the dose is selected to achieve $C_{max}$ of 3,4-DAP of about 15 ng/mL or less about 20 ng/mL or less, about 25 ng/mL or less, about 30 ng/mL or less, about 35 ng/mL or less, about 40 ng/mL or less, about 45 ng/mL or less, about 50 ng/mL or less, about 55 ng/mL or less, about 60 ng/mL or less, about 65 ng/mL or less, about 70 ng/mL or less, about 75 ng/mL or less, about 80 ng/mL or less, about 85 ng/mL or less, or about 90 ng/mL or less. In some or any embodiments, the dose is selected to achieve $C_{max}$ of 3,4-DAP of about 25 ng/mL or less, about 30 ng/mL or less, about 35 ng/mL or less, about 40 ng/mL or less, about 45 ng/mL or less, about 50 ng/mL or less, about 55 ng/mL or less, or about 60 ng/mL or less. In some or any embodiments, the dose is selected to achieve $C_{max}$ of 3,4-DAP of about 40 ng/mL or less, about 45 ng/mL or less, about 50 ng/mL or less, or about 55 ng/mL or less. In some or any embodiments, the dose is selected to achieve $C_{max}$ of 3,4-DAP of less than or equal to about 50 ng/mL and greater than or equal to about 10 ng/mL. In some or any embodiments, the dose is selected to achieve $C_{max}$ of 3,4-DAP of less than or equal to about 50 ng/mL and greater than or equal to about 15 ng/mL. In some or any embodiments, the dose is selected to achieve $C_{max}$ of 3,4-DAP of less than or equal to about 50 ng/mL and greater than or equal to about 20 ng/mL. In some or any embodiments, the dose is selected to achieve $C_{max}$ of 3,4-DAP of less than or equal to about 40 ng/mL and greater than or equal to about 10 ng/mL. In some or any embodiments, the dose is selected to achieve $C_{max}$ of 3,4-DAP of less than or equal to about 40 ng/mL and greater than or equal to about 15 ng/mL. In some or any embodiments, the dose is selected to achieve $C_{max}$ of 3,4-DAP of less than or equal to about 40 ng/mL and greater than or equal to about 20 ng/mL. In some or any embodiments, the dose is selected to achieve $C_{max}$ of 3,4-DAP of less than or equal to about 35 ng/mL and greater than or equal to about 25 ng/mL. In some or any embodiments, the dose is selected to achieve $C_{max}$ of 3,4-DAP of about 30 ng/mL. In some or any embodiments, the dose is administered to a slow acetylator with food. In some or any embodiments, the food is a high-fat, high-calorie meal. In some or any embodiments, the dose is administered to a fast acetylator without food. In some or any embodiments, the subject is female.

Embodiment K

Provided herein is a method of selecting a dose of 3,4-DAP or a pharmaceutically acceptable salt thereof for a subject who is a fast acetylator and informing the fast acetylator to take said 3,4-DAP without food. In another embodiment, the dose is selected according to any of the embodiments and examples disclosed herein.

Embodiment L

Provided herein is a method of treating a 3,4-DAP-sensitive disease comprising determining whether a subject is a slow acetylator or fast acetylator; selecting a dose of 3,4-DAP or a pharmaceutically acceptable salt thereof based on the subject's acetylator status; and administering the dose of 3,4-DAP to the subject in need thereof. In another embodiment, the acetylation status, the selected dose, and the administration, for example with or without food, is according to any of the embodiments and examples disclosed herein.

Embodiment M

Provided herein is a method of treating a 3,4-DAP-sensitive disease comprising selecting a dose of 3,4-DAP or a pharmaceutically acceptable salt thereof in an amount adjusted to the subject's acetylator status; and administering the dose of 3,4-DAP to the subject in need thereof. In another embodiment, the selected dose and the administration, for example with or without food, is according to any of the embodiments and examples disclosed herein.

Embodiment N

Provided herein is a method of treating a 3,4-DAP-sensitive disease comprising administering a dose of 3,4-DAP to the subject in need thereof in an amount adjusted to the subject's acetylator status. In another embodiment, the administration, for example with or without food, is according to any of the embodiments and examples disclosed herein.

Embodiment P

Provided herein is a method of treating a 3,4-DAP-responsive disorder with 3,4-DAP or a pharmaceutically acceptable salt thereof in a subject who is a fast acetylator in a dose of about 80 mg or more of free base (regardless of whether the dose is administered as the free base or as a pharmaceutically acceptable salt) per day. In some or any embodiments, the dose is about 100 mg or more of free base (regardless of whether the dose is administered as the free base or as a pharmaceutically acceptable salt) per day. In another embodiment, the dose is administered with food. In another embodiment, the dose is administered without food.

Embodiment Q

Provided herein is a method of treating a 3,4-DAP-responsive disorder with 3,4-DAP or a pharmaceutically acceptable salt thereof in combination with an inhibitor of an NAT enzyme. In some or any embodiments, the NAT inhibitor is acetaminophen, curcumin, or caffeic acid. In some or any embodiments, the NAT inhibitor is a NAT1 inhibitor and the NAT1 inhibitor is caffeic acid. In some or any embodiments, the NAT inhibitor is a NAT2 inhibitor and the NAT2 inhibitor is acetaminophen or curcumin.

Embodiments for a Slow Acetylator

In some or any of embodiments, for example 2-4, 6, 7, 9-11, C-J, L-N, and Q, the human is a slow acetylator and the 3,4-DAP is administered with food and the food is a high-fat, high-calorie meal.

In some or any of embodiments, for example 2-4, 6, 7, 9-11, C-J, L-N, and Q, the human is a slow acetylator and the 3,4-DAP is administered shortly following food.

In some or any of embodiments, for example 2-4, 6, 7, 9-11, C-J, L-N, and Q, the human is a slow acetylator and the 3,4-DAP is administered when the stomach is full, for example, concurrently with ingestion of food, 5 min or less after ingestion of food, 10 min or less after ingestion of food, 30 min or less after ingestion of food, 35 min or less after ingestion of food, 40 min or less after ingestion of food, 45 min or less after ingestion of food, 60 min or less after ingestion of food, 75 min or less after ingestion of food, 90 min or less after ingestion of food, 105 min or less after ingestion of food, or 120 min or less after ingestion of food. In some or any of embodiments 2-4, 6, 7, and 9-11, C-J, L-N, and Q, the composition is administered to the patient when the stomach is full, for example, concurrently with ingestion of food, 5 min or less after ingestion of food, 10 min or less after ingestion of food, 30 min or less after ingestion of food, 35 min or less after ingestion of food, 40 min or less after ingestion of food, 45 min or less after ingestion of food, or 60 min or less after ingestion of food. In some or any of embodiments, for example 2-4, 6, 7, and 9-11, C-J, L-N, and Q, the composition is administered to the patient when the stomach is full, for example, concurrently with ingestion of food, 5 min or less after ingestion of food, 10 min or less after ingestion of food, 30 min or less after ingestion of food, or 35 min or less after ingestion of food.

In some or any of embodiments, for example 2-4, 6, 7, 9-11, C-J, L-N, and Q, the human is a slow acetylator and the 3,4-DAP is administered with food and the food may be ingested at approximately the same time, or the 3,4-DAP may be ingested before or after the food. The period of time between consuming the food and taking 3,4-DAP, either swallowed or dissolved, may be about 5 min or less. For example, 3,4-DAP may be administered 30 min, 25 min, 20 min, 15 min, 10 min, or 5 min before or after a meal.

In some or any of embodiments, for example 2-4, 6, 7, 9-11, C-J, L-N, and Q, the human is a slow acetylator and the frequency of side effect(s) was reduced by about 30-35%. In some or any of embodiments, for example 2-4, 6, 7, 9-11, C-J, L-N, and Q, the human is a slow acetylator and the frequency of side effect(s) was reduced by about at least a third. In some or any of embodiments, for example 2-4, 6, 7, 9-11, C-J, L-N, and Q, the human is a slow acetylator and the frequency of side effect(s) was reduced by about 25-30%. In some or any of embodiments, for example 2-4, 6, 7, 9-11, C-J, L-N, and Q, the human is a slow acetylator and the frequency of side effect(s) was reduced by about 20-25%. In some or any of embodiments, for example 2-4, 6, 7, 9-11, C-J, L-N, and Q, the human is a slow acetylator and the frequency of side effect(s) was reduced by about 15-20%. In some or any of embodiments, for example 2-4, 6, 7, 9-11, C-J, L-N, and Q, the human is a slow acetylator and the frequency of side effect(s) was reduced by about 10-15%. In some or any of embodiments, for example 2-4, 6, 7, 9-11, C-J, L-N, and Q, the human is a slow acetylator and the frequency of side effect(s) was reduced by about 5-10%.

In some or any of embodiments, for example 2-4, 6, 7, 9-11, C-J, L-N, and Q, the human is a slow acetylator and the side effect is a nervous system disorders and is decreased by about at least 30%. In some or any of embodiments, for example 2-4, 6, 7, 9-11, C-J, L-N, and Q, the human is a slow acetylator and the frequency of side effects was reduced by about 25-30%. In some or any of embodiments, for example 2-4, 6, 7, 9-11, C-J, L-N, and Q, the human is a slow acetylator and the frequency of side effects was reduced by about 20-25%. In some or any of embodiments, for example 2-4, 6, 7, 9-11, C-J, L-N, and Q, the human is a slow acetylator and the frequency of side effects was reduced by about 15-20%. In some or any of embodiments, for example 2-4, 6, 7, 9-11, C-J, L-N, and Q, the human is a slow acetylator and the frequency of side effects was reduced by about 10-15%. In some or any of embodiments, for example 2-4, 6, 7, 9-11, C-J, L-N, and Q, the human is a slow acetylator and the frequency of side effects was reduced by about 5-10%. In some or any of embodiments, for example 2-4, 6, 7, 9-11, C-J, L-N, and Q, the human is a slow acetylator and the nervous system disorder that is decreased is paraesthesia, e.g. oral or skin.

In some or any of embodiments, for example 2-4, 6, 7, 9-11, C-J, L-N, and Q, the human is a slow acetylator and the side effect is paraesthesia and the frequency is decreased by at least about 35%, in another example by about 30-35%, in another example by about 25-30%, in another example by about 20-25%, in another example by about 15-20%, in another example by about 15-20%, in another example by 10-15%.

In some or any of embodiments, for example 2-4, 6, 7, 9-11, C-J, L-N, and Q, the human is a slow acetylator and the side effect is dizziness and the frequency is decreased by at least about 60%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is oral headache and the frequency is decreased by at least about 75%, in another example by about 70-75%, in another example by about 65-70%, in another example by about 60-65%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is hypoaesthesia and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is facial hypoaesthesia and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is a gastrointestinal disorder and is decreased by at least about 80% amount, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is a nausea and is decreased by at least about 65% amount, in another example by about two thirds, in another example by about 60-65%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is abdominal pain and/or tenderness and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In some or any of embodiments, for example 2-4, 6, 7, 9-11, C-J, L-N, and Q, the human is a slow acetylator and the side effect is diarrhea and the frequency is decreased by about 100%, in another example by about 90-100%, in another example by about 80-90%, in another example by about 70-80%, in another example by about 60-70%, in another example by about 55-60%, in another example by about 50-55%, in another example by about 45-50%, in another example by about 40-45%, in another example by about 35-40%, in another example by 30-35%, in another example by about 25-30%, in another example by about 20-25%, in another example by about 15-20%, in another example by about 10-15%, in another example by about 5-10%.

In the following embodiments, the dose amount listed is the amount of free base in a dose whether the dose is administered as a free base or as a pharmaceutically acceptable salt thereof. In some or any of embodiments, for example 2-4, 6, 7, 9-11, B-J, L-N, and Q, the human is a slow acetylator and the optional pharmaceutically acceptable salt is phosphate. In some or any of embodiments, for example 2-4, 6, 7, 9-11, B-J, L-N, and Q, the human is a slow acetylator and the amount of 3,4-DAP selected and/or administered is less than 40 mg total per day. In some or any of embodiments, for example 2-4, 6, 7, 9-11, B-J, L-N, and Q, the human is a slow acetylator and the amount of 3,4-DAP selected and/or administered is less than 35 mg (base equivalent) total per day. In some or any of embodiments, for example 2-4, 6, 7, 9-11, B-J, L-N, and Q, the human is a slow acetylator and the amount of 3,4-DAP selected and/or administered is less than 30 mg total per day. In some or any of embodiments, for example 2-4, 6, 7, 9-11, B-J, L-N, and Q, the human is a slow acetylator and the amount of 3,4-DAP selected and/or administered is less than 25 mg total per day. In some or any of embodiments, for example 2-4, 6, 7, 9-11, B-J, L-N, and Q, the human is a slow acetylator and the amount of 3,4-DAP selected and/or administered is less than 20 mg total per day. In some or any of embodiments, for example 2-4, 6, 7, 9-11, B-J, L-N, and Q, the human is a slow acetylator and the amount of 3,4-DAP selected and/or administered is less than 15 mg total per day. In some or any of embodiments, for example 2-4, 6, 7, 9-11, B-J, L-N, and Q, the human is a slow acetylator and the amount of 3,4-DAP selected and/or administered is less than or equal to 12 mg total per day. In some or any of embodiments, for example 2-4, 6, 7, 9-11, B-J, L-N, and Q, the human is a slow acetylator and the amount of 3,4-DAP selected and/or administered is less than or equal to 10 mg total per day. In some or any of embodiments, for example 2-4, 6, 7, 9-11, B-J, L-N, and Q, the human is a slow acetylator and the amount of 3,4-DAP selected and/or administered is less than or equal to 9 mg total per day. In some or any of embodiments, for example 2-4, 6, 7, 9-11, B-J, L-N, and Q, the human is a slow acetylator and the amount of 3,4-DAP selected and/or administered is less than or equal to 6 mg total per day. In some or any of embodiments, for example 2-4, 6, 7, 9-11, B-J, L-N, and Q, the human is a slow acetylator and the amount of 3,4-DAP selected and/or administered is less than or equal to 5 mg total per day. In some or any of embodiments, for example 2-4, 6, 7, 9-11, B-J, L-N, and Q, the human is a slow acetylator and the amount of 3,4-DAP selected and/or administered is less than or equal to 3 mg total per day. In some or any of embodiments, for example 2-4, 6, 7, 9-11, B-J, L-N, and Q, the human is a slow acetylator and the amount of 3,4-DAP selected and/or administered is less than or equal to 2.5 mg total per day. In some or any of embodiments, for example 2-4, 6, 7, 9-11, B-J, L-N, and Q, the human is a slow acetylator and the 3,4-DAP is selected and/or administered one time a day. In some or any of embodiments, for example 2-4, 6, 7, 9-11, B-J, L-N, and Q, the human is a slow acetylator and the 3,4-DAP is selected and/or administered two times a day. In some or any of embodiments, for example 2-4, 6, 7, 9-11, B-J, L-N, and Q, the human is a slow acetylator and the 3,4-DAP is selected and/or administered three times a day. In some or any of embodiments, for example 2-4, 6, 7, 9-11, B-J, L-N, and Q, the human is a slow acetylator and the 3,4-DAP is selected and/or administered four times a day.

In the following embodiments, the dose amount listed is the amount of free base in a dose whether the dose is administered as a free base or as a pharmaceutically acceptable salt thereof. In some or any of embodiments 2-4, 6, 7, 9-11, B-J, L-N, and Q, the optional pharmaceutically acceptable salt is phosphate. In some or any of embodiments 2-4, 6, 7, 9-11, B-J, L-N, and Q, the amount of 3,4-DAP selected and/or administered is less than about 40 mg total per day. In some or any of embodiments 2-4, 6, 7, 9-11, B-J, L-N, and Q, the amount of 3,4-DAP selected and/or administered is less than about 35 mg total per day. In some or any of embodiments 2-4, 6, 7, 9-11, B-J, L-N, and Q, the amount of 3,4-DAP selected and/or administered is less than about 30 mg total per day. In some or any of embodiments 2-4, 6, 7, 9-11, B-J, L-N, and Q, the amount of 3,4-DAP selected and/or administered is less than about 25 mg total per day. In some or any of embodiments 2-4, 6, 7, 9-11, B-J, L-N, and Q, the amount of 3,4-DAP selected and/or administered is less than about 20 mg total per day. In some or any of embodiments 2-4, 6, 7, 9-11, B-J, L-N, and Q, the amount of 3,4-DAP selected and/or administered is less than about 15 mg total per day. In some or any of embodiments 2-4, 6, 7, 9-11, B-J, L-N, and Q, the amount of 3,4-DAP selected and/or administered is less than or equal to about 12 mg total per day. In some or any of embodiments 2-4, 6, 7, 9-11, B-J, L-N, and Q, the amount of 3,4-DAP selected and/or administered is less than or equal to about 10 mg total per day. In some or any of embodiments 2-4, 6, 7, 9-11, B-J, L-N, and Q, the amount of 3,4-DAP selected and/or administered is less than or equal to about 9 mg total per day. In some or any of embodiments 2-4, 6, 7, 9-11, B-J, L-N, and Q, the amount of 3,4-DAP selected and/or administered is less than or equal to about 6 mg total per day. In some or any of embodiments 2-4, 6, 7, 9-11, B-J, L-N, and Q, the amount of 3,4-DAP selected and/or administered is less than or equal to about 5 mg total per day. In some or any of embodiments 2-4, 6, 7, 9-11, B-J, L-N, and Q, the amount of 3,4-DAP selected and/or administered is less than or equal to about 3 mg total per day. In some or any of embodiments 2-4, 6, 7, 9-11, B-J, L-N, and Q, the amount of 3,4-DAP selected and/or administered is less than or equal to about 2.5 mg total per day. In some or any of embodiments 2-4, 6, 7, 9-11, B-J, L-N, and Q, the 3,4-DAP is selected and/or administered one time a day. In some or any of embodiments 2-4, 6, 7, 9-11, B-J, L-N, and Q, the 3,4-DAP is selected and/or administered two times a day. In some or any of embodiments 2-4, 6, 7, 9-11, B-J, L-N, and Q, the 3,4-DAP is selected and/or administered three times a day. In some or any of embodiments 2-4, 6, 7, 9-11, B-J, L-N, and Q, the 3,4-DAP is selected and/or administered four times a day.

In the following embodiments, the dose amount listed is the amount of free base in a dose whether the dose is administered as a free base or as a pharmaceutically acceptable salt thereof. In some or any of embodiments, for example 2-4, 6, 7, 9-11, B-J, L-N, and Q, the optional pharmaceutically acceptable salt is phosphate. In some or any of embodiments, for example 2-4, 6, 7, 9-11, B-J, L-N, and Q, the amount of 3,4-DAP selected and/or administered is about 40 mg total per day, about 35 mg total per day, about 30 mg total per day, about 25 mg total per day, about 20 mg total per day, about 15 mg total per day, about 12 mg total per day, about 10 mg total per day, about 9 mg total per day, about 6 mg total per day, about 5 mg total per day, about 3 mg total per day, or about 2.5 mg total per day. In some or any of embodiments, for example 2-4, 6, 7, 9-11, B-J, L-N, and Q, the 3,4-DAP is selected and/or administered one time a day. In some or any of embodiments, for example 2-4, 6, 7, 9-11, B-J, L-N, and Q, the 3,4-DAP is selected and/or administered two times a day. In some or any of embodiments, for example 2-4, 6, 7, 9-11, B-J, L-N, and Q, the 3,4-DAP is selected and/or administered three times a day. In some or any of embodiments, for example 2-4, 6, 7, 9-11, B-J, L-N, and Q, the 3,4-DAP is selected and/or administered four times a day.

Embodiments for a Fast Acetylator

In some or any of embodiments, for example 2-5, 7-11, C, D, and H-Q, the human is a fast acetylator and the 3,4-DAP is administered when the stomach is empty, for example, 60 min or more before or 120 min or more after ingestion of food.

In some or any of embodiments, for example 2-5, 7-11, C, D, and H-Q, the human is a fast acetylator and the 3,4-DAP is administered without food, for example, 60 min or more before or 120 min or more after ingestion of food.

In some or any of embodiments, for example 2-5, 7-11, C, D, and H-Q, the human is a fast acetylator and the 3,4-DAP is administered under fasting conditions, for example, 60 min or more before or 120 min or more after ingestion of food.

In some or any of embodiments, for example 2-5, 7-11, B, C, D, and H-Q, the human is a fast acetylator and the efficacy of 3,4-DAP is increased when taken without food. In some or any of embodiments, for example 2-5, 7-11, C, D, and H-Q, the human is a fast acetylator and the efficacy of 3,4-DAP is increased by about 5% or more when taken without food. In another example the efficacy is increased by about 10% or more. In another example the efficacy is increased by about 15% or more. In another example the efficacy is increased by about 20% or more. In another example the efficacy is increased by about 25% or more. In another example the efficacy is increased by about 30% or more. In another example the efficacy is increased by about 35% or more. In another example the efficacy is increased by about 40% or more.

In the following embodiments, the dose amount listed is the amount of free base in a dose whether the dose is administered as a free base or as a pharmaceutically acceptable salt thereof. In some or any of embodiments, for example 2-5, 7-11, B, C, D, and H-Q, the human is a fast acetylator and the optional pharmaceutically acceptable salt is phosphate. In some embodiments, the human is a fast acetylator and the amount of 3,4-DAP selected and/or administered is greater than or equal to about 30 mg total per day. In some embodiments, the human is a fast acetylator and the amount of 3,4-DAP selected and/or administered is greater than or equal to about 40 mg total per day. In some embodiments, the human is a fast acetylator and the amount of 3,4-DAP selected and/or administered is greater than or equal to about 50 mg total per day. In some embodiments, the human is a fast acetylator and the amount of 3,4-DAP selected and/or administered is greater than or equal to about 60 mg total per day. In some embodiments, the human is a fast acetylator and the amount of 3,4-DAP selected and/or administered is greater than or equal to about 80 mg total per day. In some embodiments, the human is a fast acetylator and the amount of 3,4-DAP selected and/or administered is greater than or equal to about 100 mg total per day. In some embodiments, the human is a fast acetylator and the amount of 3,4-DAP selected and/or administered is greater than or equal to about 120 mg total per day. In some embodiments, the human is a fast acetylator and the amount of 3,4-DAP selected and/or administered is greater than or equal to about 140 mg total per day. In some embodiments, the human is a fast acetylator and the amount of 3,4-DAP selected and/or administered is greater than or equal to about 160 mg total per day. In some embodiments, the human is a fast acetylator and the amount of 3,4-DAP selected and/or administered is greater than or equal to about 180 mg total per day. In some embodiments, the human is a fast acetylator and the amount of 3,4-DAP selected and/or administered is greater than or equal to about 200 mg total per day. In some embodiments, the human is a fast acetylator and the amount of 3,4-DAP selected and/or administered is greater than or equal to about 220 mg total per day. In some embodiments, the human is a fast acetylator and the amount of 3,4-DAP selected and/or administered is greater than or equal to about 240 mg total per day. In some embodiments, the human is a fast acetylator and the 3,4-DAP is administered one time a day. In some embodiments, the human is a fast acetylator and the 3,4-DAP is administered two times a day. In some embodiments, the human is a fast acetylator and the 3,4-DAP is administered three times a day. In some embodiments, the human is a fast acetylator and the 3,4-DAP is administered four times a day. In some embodiments, the human is a fast acetylator and the 3,4-DAP is administered five times a day.

In the following embodiments, the dose amount listed is the amount of free base in a dose whether the dose is administered as a free base or as a pharmaceutically acceptable salt thereof. In some or any embodiments 2-5, 7-11, B, C, D, and H-Q, the optional pharmaceutically acceptable salt is phosphate. In some or any embodiments 2-5, 7-11, B, C, D, and H-Q, the amount of 3,4-DAP selected and/or administered is greater than or equal to about 30 mg total per day. In some embodiments, the amount of 3,4-DAP selected and/or administered is greater than or equal to about 40 mg total per day. In some embodiments, the amount of 3,4-DAP selected and/or administered is greater than or equal to about 50 mg total per day. In some embodiments, the amount of 3,4-DAP selected and/or administered is greater than or equal to about 60 mg total per day. In some embodiments, the amount of 3,4-DAP selected and/or administered is greater than or equal to about 80 mg total per day. In some embodiments, the amount of 3,4-DAP selected and/or administered is greater than or equal to about 100 mg total per day. In some embodiments, the amount of 3,4-DAP selected and/or administered is greater than or equal to about 120 mg total per day. In some embodiments, the amount of 3,4-DAP selected and/or administered is greater than or equal to about 140 mg total per day. In some embodiments, the amount of 3,4-DAP selected and/or administered is greater than or equal to about 160 mg total per day. In some embodiments, the amount of 3,4-DAP selected and/or administered is greater than or equal to about 180 mg total per day. In some embodiments, the amount of 3,4-DAP selected and/or administered is greater than or equal to about 200 mg total per day. In some embodiments, the amount of 3,4-DAP selected and/or administered is greater than or equal to about 220 mg total per day. In some embodiments, the amount of 3,4-DAP selected and/or administered is greater than or equal to about 240 mg total per day. In some embodiments, the 3,4-DAP is selected and/or administered one time a day. In some embodiments, the 3,4-DAP is selected and/or administered two times a day. In some embodiments, the 3,4-DAP is selected and/or administered three times a day. In some embodiments, the 3,4-DAP is selected and/or administered four times a day. In some embodiments, the 3,4-DAP is administered five times a day.

In the following embodiments, the dose amount listed is the amount of free base in a dose whether the dose is administered as a free base or as a pharmaceutically acceptable salt thereof. In some or any embodiments, for example 2-5, 7-11, B, C, D, and H-Q, the optional pharmaceutically acceptable salt is phosphate. In some or any of embodiments, for example 2-5, 7-11, B, C, D, and H-Q, the amount of 3,4-DAP selected and/or administered is greater than or equal to about 30 mg total per day, greater than or equal to about 40 mg total per day, greater than or equal to about 50 mg total per day, greater than or equal to about 60 mg total per day, greater than or equal to about 80 mg total per day, greater than or equal to about 100 mg total per day, greater than or equal to about 120 mg total per day, greater than or equal to about 140 mg total per day, greater than or equal to about 160 mg total per day, greater than or equal to about 180 mg total per day, greater than or equal to about 200 mg per day, greater than or equal to about 220 mg per day, or greater than or equal to about 240 mg per day. In some embodiments, the 3,4-DAP is selected and/or administered one time a day. In some embodiments, the 3,4-DAP is selected and/or administered two times a day. In some embodiments, the 3,4-DAP is selected and/or administered three times a day. In some embodiments, the 3,4-DAP is selected and/or administered four times a day. In some embodiments, the 3,4-DAP is administered five times a day.

In the following embodiments, the dose amount listed is the amount of free base in a dose whether the dose is administered as a free base or as a pharmaceutically acceptable salt thereof. In some or any embodiments, for example 2-5, 7-11, B, C, D, and H-Q, the optional pharmaceutically acceptable salt is phosphate. In some or any of embodiments, for example 2-5, 7-11, B, C, D, and H-Q, the amount of 3,4-DAP selected and/or administered is about 30 mg total per day, about 40 mg total per day, about 50 mg total per day, 60 mg total per day, about 80 mg total per day, about 100 mg total per day, about 120 mg total per day, about 140 mg total per day, about 160 mg total per day, about 180 mg total per day, about 200 mg per day, about 220 mg per day, or about 240 mg per day. In some embodiments, the 3,4-DAP is selected and/or administered one time a day. In some embodiments, the 3,4-DAP is selected and/or administered two times a day. In some embodiments, the 3,4-DAP is selected and/or administered three times a day. In some embodiments, the 3,4-DAP is selected and/or administered four times a day. In some embodiments, the 3,4-DAP is administered five times a day.

Embodiment 12

Disclosed herein is a method of treating a 3,4-DAP-sensitive disease in a subject, comprising administering 3,4-DAP or a pharmaceutically acceptable salt thereof; and determining the ratio of acetylated 3,4-DAP to 3,4-DAP in said subject using any method as described in any of the embodiments and examples herein, for example the 3,4-DAP test. In some or any embodiments, the method further comprises informing the subject that the amount of 3,4-DAP should be increased or decreased in order to optimize efficacy or reduce the frequency and/or severity of side effects. In some or any embodiments, the subject has a ratio of about 15 or less and is informed that 3,4-DAP should be taken with food. In some or any embodiments, the subject has a ratio of about 15 or less and is informed that side effects will be reduced when 3,4-DAP is taken with food. In some or any embodiments, the subject has a ratio of about 30 or more and is informed that 3,4-DAP should be taken without food. In some or any embodiments, the subject has a ratio of about 30 or more and is informed that efficacy will be increased when 3,4-DAP is taken without food. In some or any embodiments, the method further comprises increasing or reducing the amount of 3,4-DAP, or pharmaceutically acceptable salt thereof, administered to the subject in order to optimize efficacy or reduce the frequency and/or severity of side effects. In some or any embodiments, the acetylated 3,4-DAP is N-(4-aminopyridin-3-yl)acetamide. In some or any embodiments, for the subject whose ratio is about 15 or less, 3,4-DAP is taken with food. In some or any embodiments, for the subject whose ratio is about 30 or more, 3,4-DAP is taken without food.

Embodiment 13

In some or any embodiments, the subject is a fast acetylator and is informed that 3,4-diaminopyridine or a pharmaceutically acceptable salt thereof should be taken with food. In some or any embodiments, the subject is a fast acetylator and 3,4-diaminopyridine or a pharmaceutically acceptable salt thereof is administered with food.

Embodiment 14

Disclosed is a method comprising administering 3,4-diaminopyridine or a pharmaceutically acceptable salt thereof, to a human in need thereof, and informing said human that the frequency and/or severity of side effect(s) of said 3,4-DAP or pharmaceutically acceptable salt thereof are decreased when it is ingested with food compared to when ingested without food.

Embodiment 15

Disclosed is a method of dosing a subject with renal impairment. In some or any embodiments, the subject is started at a dose of about 10 mg free base equivalent per day (regardless of whether free base or a pharmaceutically acceptable salt is administered). In some or any embodiments, 3,4-DAP, or a pharmaceutically acceptable salt thereof is administered with food. In some or any embodiments, a subject with renal impairment is treated as a slow metabolizer regardless of their NAT1 and/or NAT2 phenotype and/or genotype.

In one example at least 99.5% pure 3,4-DAP is used. Any salt, including the phosphate and tartrate salts, and any crystalline form of 3,4-DAP may be utilized according to the methods and compositions provided herein. A variety of salts are described in U.S. Patent Publication No. US20040106651, incorporated herein by reference in its entirety.

Disclosed is a method of determining whether a subject is a slow or fast acetylator of 3,4-DAP comprising determining the subject's NAT polymorphism phenotype or genotype. In another embodiment, the phenotype and genotype can be determined using any of the embodiments and examples as described herein.

Kits/Articles of Manufacture

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example in some embodiments the container is an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In certain embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In certain embodiments, a label indicates that the contents are to be used for a specific therapeutic application. In some embodiments, the label indicates directions for use of the contents, such as in the methods described herein.

In certain embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In certain embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

Terms

"About," as used herein, unless otherwise indicated, refers to a value that is no more than 10% above or below the value being modified by the term. For example, the term "about 1 hour" means a range of from 48 min to 72 min. Further, when the term "about" is used in relation to a specified dosage amount or range, the term "about" indicates that the dosage amount or range specified is an approximate dosage amount or range and that it includes not only the amount or range actually specified, but those amounts or ranges that may also be safe and effective amounts that are somewhat, e.g., 10%, outside the cited amount or range.

"Administration with food," "administered under fed conditions," "administered on a full stomach," and like phrases, unless otherwise indicated, means the drug is administered less than about one hour before food is ingested or less than about two hours after food is ingested. In another example, these phrases mean that the drug is administered less than about 30 min before food is ingested or less than about 45 min after food is ingested. In another example, these phrases mean that the drug is administered less than about 15 min before food is ingested or less than about 30 min after food is ingested. In another example, the phrases have meanings as described in the embodiments and/or examples herein.

"Administration without food," "administered under fasting conditions," "administered on an empty stomach," and like phrases, unless otherwise indicated, means the drug is administered more than one hour before food is ingested or more than two hours after food is ingested. In another example, these phrases mean that the drug is administered more than two hours before food is ingested or more than three hours after food is ingested. In another example, the phrases have meanings as described in the embodiments and/or examples herein.

As used herein, the term "bioavailability" refers to the fraction of an administered dose of a drug entering systemic circulation. If the drug were administered intravenously, then its bioavailability theoretically would be 100%. However, if the drug were administered via other routes (such as orally), then its bioavailability would be less than 100% as a result of, for example, incomplete absorption in the GI tract, degradation or metabolism prior to absorption, and/or hepatic first pass effect.

"Fast alleles," as used herein, for NAT2 mean alleles *4 (wildtype) and potentially *13.

"Fast acetylator" or "fast metabolizer" is a person who has a plasma concentration of 0-5 ng/mL 3,4-DAP at 4 hours post dose. Alternatively, a fast acetylator is a person who has a ratio of greater than about 0.2, for example between about 0.2 and about 0.3, as calculated using the following formula (AFMU+AAMU)/(AFMU+AAMU+1×+1U) after administration of 150 mg caffeine. Alternatively, a fast acetylator is a person who has at least one fast allele, in another embodiment, two fast NAT2 alleles. Alternatively, a fast metabolizer is as described in Table 4 or any of the embodiments or examples herein.

The term "high fat meal" refers generally to a meal of at least about 700 kcal and at least about 45% fat (relative percentage of kcal which are fat), or alternatively at least about 900 kcal and at least about 50% fat. The term "high fat food" refers generally to a food comprising at least 20 g of fat, or at least 25, 30, 35, 40, 45, or 50 g of fat, and/or at least about 45% or 50% fat. One FDA Guidance defines a "high-fat meal" as approximately 50% of total caloric content of the meal, whereas a "high-calorie meal" is approximately 800 to 1000 calories. The FDA recommends a high-fat and high-calorie meal as a test meal for food-effect bioavailability and fed bioequivalence studies. This test meal should derive approximately 150, 250, and 500-600 calories from protein, carbohydrate and fat, respectively. An example test meal consists of two eggs fried in butter, two strips of bacon, four ounces of hash brown potatoes and eight ounces of whole milk. Substitution is possible if a similar amount of calories from protein, carbohydrate, and fat has comparable meal volume and viscosity (Guidance for Industry, Food-Effect Bioavailability and Fed Bioequivalence Studies, U.S. Department of Health and Human Services, Food and Drug Administration, Center for Drug Evaluation and Research (CDER), December 2002).

The phrase "human whose phenotype is slow acetylation" and the phrase "a subject is a slow acetylator" are essentially equivalent in meaning.

The phrase "human whose phenotype is fast acetylation" and the phrase "a subject is a fast acetylator" are essentially equivalent in meaning.

"Intermediate acetylator" and "intermediate metabolizer" is a person who has a plasma concentration of possibly 5-10 ng/mL at 4 hours post dose. Alternatively, an intermediate acetylator is a person who has one fast NAT2 allele and one slow allele. An intermediate acetylator is a subcategory of fast acetylator.

"Mean plasma concentration" means the average of readings of concentration in a series of plasma samples.

"NAT polymorphism phenotype" as used herein include slow, intermediate, and fast acetylation status.

"NAT polymorphism genotype" as used herein refers to the number of fast or slow alleles a person has. Two fast alleles mean the person is a fast acetylator. One fast and one slow mean the person is an intermediate acetylator which is a subcategory of fast acetylator. No fast alleles mean the person is a slow acetylator.

"Slow alleles," as used herein, for NAT2 mean alleles *5, *6, and *7.

"Slow acetylator" or "slow metabolizer" is a person who has a plasma concentration of 10-26 ng/mL 3,4-DAP at 4 hours post dose. Alternatively, a slow acetylator is a person who has a ratio of about 0.2 or less, for example between about 0.1 and about 0.2 (inclusive) as calculated using the following formula (AFMU+AAMU)/(AFMU+AAMU+1x+1U) after administration of 150 mg caffeine. Alternatively, a slow acetylator is a person who has no fast NAT2 alleles. Alternatively, a slow metabolizer is as described in Table 4 or any of the embodiments or examples herein.

For the purpose of defining the potential side effects of taking 3,4-DAP, "nervous system disorders" include, but are not limited to, paraesthesia, paraesthesia oral, dizziness, hypoaesthesia oral, headache, dysgeusia, hypoaesthesia, and hypoaesthesia facial.

For the purpose of defining the potential side effects of taking 3,4-DAP, "gastrointestinal disorders" include, but are not limited to, nausea, abdominal pain, upper abdominal pain, abdominal tenderness, constipation, diarrhea, and oropharyngeal pain.

For the purpose of defining the potential side effects of taking 3,4-DAP, "general disorders and administration site conditions" include, but are not limited to, fatigue, catheter sire pain, and feeling hot.

For the purpose of defining the potential side effects of taking 3,4-DAP, "infections and infestations" include, but are not limited to, gastroenteritis and nasopharyngitis.

For the purpose of defining the potential side effects of taking 3,4-DAP, "skin and subcutaneous tissue disorders" include, but are not limited to, acne and blister.

For the purpose of defining the potential side effects of taking 3,4-DAP, "vascular disorders" include, but are not limited to, flushing and phlebitis.

For the purpose of defining the potential side effects of taking 3,4-DAP, "cardiac disorders" include, but are not limited to, presyncope.

For the purpose of defining the potential side effects of taking 3,4-DAP, "musculoskeletal and connective tissue disorders" include, but are not limited to, musculoskeletal stiffness.

Any of the preceding methods may be carried out by providing or administering 3,4-diaminopyridine in a container containing printed labeling informing the patient of the change in absorption parameters described above.

Optionally, the methods provided herein also comprise the step of providing to the patient in need thereof a therapeutically effective amount of 3,4-diaminopyridine. The therapeutically effective amount will vary depending on the condition to be treated, and can be readily determined by the treating physician based on improvement in desired clinical symptoms.

Abbreviations

The abbreviations have the following meanings.

| | |
|---|---|
| 1U | 1-methylurate |
| 1X | 1-methylxanthine |
| $\lambda_z$ | Apparent terminal elimination rate constant |
| 3,4-DAP | 3,4-diaminopyridine; amifampridine |
| AAMU | 5-acetylamino-6-amino-3-methyluracil |
| AE | adverse event |
| Ae | Amount of drug excreted in urine |
| AFMU | 5-acetylamino-6-formylamino-3-methyluracil |
| ALT | alanine aminotransferase |
| API | active pharmaceutical ingredient |
| AST | aspartate aminotransferase |
| ATP | adenosine triphosphate |
| AUC | area under the plasma concentration-time curve |
| $AUC_{0-t}$ | Area under the plasma concentration-time curve from time zero up to the last measurable concentration |
| $AUC_{0-inf}$ | Area under the plasma concentration-time curve from time zero to infinity |
| % $AUC_{extrap}$ | Percentage of AUC that is due to extrapolation from Tlast to infinity |
| BMI | body mass index |
| BMN125 | 3,4-diaminopyridine phosphate |
| BUN | blood urea nitrogen |
| $CO_2$ | carbon dioxide |
| CHO | Chinese hamster ovary |
| CI | confidence interval |
| CL/F | Apparent total plasma clearance |
| $CL_R$ | Renal clearance |
| $C_{max}$ | Maximum observed plasma concentration |
| CRF | Case Report Form |
| CRU | Clinical Research Unit |
| CV | coefficient of variation |
| DMSO | dimethylsulfoxide |
| ECG | electrocardiogram |
| EGTA | ethylene glycol tetraacetic acid |
| Equiv | equivalents |
| FAM ™ | 6-carboxy-fluorescine |
| FBS | fetal bovine sera |
| fe | Fraction of dose excreted in urine |
| FSH | follicle stimulating hormone |
| GCP | Good Clinical Practice |
| GGT | gamma-glutamyltransferase |
| GI | gastrointestinal or gastrointestine |
| GLP | Good Laboratory Practice |
| HBsAg | hepatitis B surface antigen |
| hCG | human chorionic gonadotrophin |
| HEPES | 4-(2-hydroxyethyl)-1-piperazineethanesulfonic acid |
| HIV | human immunodeficiency virus |
| hKv | human potassium channel |
| ICH | International Conference on Harmonization |
| IP | investigational product |
| ITT | intent to treat |

| | |
|---|---|
| LC/MS/MS | liquid chromatography with tandem mass spectrometric detection |
| LDH | lactate dehydrogenase |
| LEMS | Lambert-Eaton myasthenic syndrome |
| LS | least squares |
| MedDRA | Medical Dictionary for Regulatory Activities |
| min | minutes |
| mV | milivolt |
| NAT | N-acetyl transferase |
| PK | pharmacokinetic |
| QMG | quantitative myasthenia gravis score |
| QTc | QT interval corrected |
| QTcB | QT interval with Bazett's correction |
| RBC | red blood cell |
| SAE | serious adverse event |
| SD | standard deviation |
| SGOT | serum glutamic-oxaloacetic transaminase |
| SGPT | serum glutamic-pyruvic transaminase |
| $t_{1/2}$ | Apparent plasma terminal elimination half-life |
| T3 | triiodothyronine |
| T4 | thyroxine |
| TID | three times a day |
| $T_{last}$ | Time of last quantifiable plasma concentration |
| $T_{max}$ | Time of the maximum observed plasma concentration |
| TSH | thyroid-stimulating hormone |
| VID | volunteer information document |
| $V_z/F$ | Apparent volume of distribution at the terminal phase |
| WBC | white blood cell |

Pharmaceutical Formulations

The formulations described herein are in one example administered as oral formulations. Oral formulations are in one example solid formulations such as capsules, tablets, pills and troches, or liquid formulations such as aqueous suspensions, elixirs and syrups. The various form of 3,4-DAP described herein can be directly used as powder (micronized particles), granules, suspensions or solutions, or it may be combined together with other pharmaceutically acceptable ingredients in admixing the components and optionally finely divide them, and then filling capsules, composed for example from hard or soft gelatin, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be, for example, binders such as natural or synthetic polymers, excipients, lubricants, surfactants, sweetening and flavoring agents, coating materials, preservatives, dyes, thickeners, adjuvants, antimicrobial agents, antioxidants and carriers for the various formulation types. The phrase "pharmaceutically or pharmacologically acceptable" refers to molecular entities and compositions that are approved by the U.S. Food and Drug Administration or a corresponding foreign regulatory agency for administration to humans. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions.

The initial amount of 3,4-diaminopyridine used to prepare the formulation may be, for example, in the range of about 5 wt % to about 15 wt % of the formulation, or in the range of about 7 wt % to about 13 wt %, or in the ranges of about 7 wt % to about 9 wt %. Specific amounts of 3,4-DAP in a tablet formulation contemplated herein include 5 mg, 10 mg, 15 mg, 20 mg, 25 mg, and 30 mg.

Binders assist in maintaining a solid formulation. In some cases, anhydrous binders are used to preserve the anhydrous state of polymorph forms. In some cases, the binder may act as a drying agent. Exemplary binders include anhydrous dibasic calcium phosphate and its monohydrate. Other non-limiting examples of binders useful in a composition described herein include gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or cross-linked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan.

Disintegration agents assist in rapid disintegration of solid formulations by absorbing water and expanding. Exemplary disintegration agents include polyvinylpyrrolidone (PVP, e.g., sold under the name POVIDONE), a cross-linked form of povidone (CPVP, e.g., sold under the name CROSPOVIDONE), a cross-linked form of sodium carboxymethylcellulose (NaCMC, e.g., sold under the name AC-DI-SOL), other modified celluloses, and modified starch. Tablets formulated with CPVP exhibited much more rapid disintegration than tablets formulated with PVP.

Lubricants improve stability, hardness and uniformity of solid formulations. Exemplary lubricants include stearyl fumarate and magnesium stearate. Other non-limiting examples of lubricants include natural or synthetic oils, fats, waxes, or fatty acid salts such as magnesium stearate.

Optionally the stable formulations provided herein can also comprise other excipients such as mannitol, hydroxyl propyl cellulose, microcrystalline cellulose, or other non-reducing sugars such as sucrose, trehalose, melezitose, planteose, and raffinose. Reducing sugars may react with 3,4-DAP. Other non-limiting examples of excipients useful in a composition described herein include phosphates such as dicalcium phosphate.

Surfactants for use in a composition described herein can be anionic, anionic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, sodium oleate or sodium caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or distearate, glycerol mono- or dioleate and glycerol mono- or dipalmitate, and polyoxyethylene stearate.

Non-limiting examples of sweetening agents useful in a composition described herein include sucrose, fructose, lactose or aspartame. Non-limiting examples of flavoring agents for use in a composition described herein include peppermint, oil of wintergreen or fruit flavors such as cherry or orange flavor. Non-limiting examples of coating materials for use in a composition described herein include gelatin, wax, shellac, sugar or other biological degradable polymers. Non-limiting examples of preservatives for use in a composition described herein include methyl or propylparabens, sorbic acid, chlorobutanol, phenol and thimerosal.

The 3,4-DAP used in a composition described herein can be formulated as the free base or as a phosphate salt or alternatively as a tartrate salt; however, it is contemplated that other salt forms of 3,4-DAP possess the desired biological activity, and consequently, other salt forms of 3,4-DAP can be used. Specifically, for example, 3,4-DAP salts can be formed with inorganic or organic acids. Nonlimiting examples of alternative 3,4-DAP salts forms includes 3,4-DAP salts of acetic acid, citric acid, oxalic acid, tartaric acid, fumaric acid, and mandelic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5 disulfonic acid, 2- or 3-phosphoglycerate, glucose 6 phosphate, N-cyclohexylsulfamic acid (with the formation of cyclamates), or with other acid organic compounds, such as ascorbic acid.

Exemplary stable oral formulations contain one or more of the following additional ingredients that improve the stability or other characteristics of the formulation: binder, disintegration agent, acidic antioxidant, or lubricant or combinations thereof. Exemplary stable tablet formulations include a binder and disintegration agent, optionally with an acidic antioxidant, and optionally further including a lubricant. Exemplary concentrations of binder are between about 1 wt % to about 5 wt %, or between about 1.5 and 3 wt %; an exemplary weight ratio of binder to 3,4-DAP is in the range of about 1:10 to about 1:20. Exemplary concentrations of disintegration agent are between about 1 wt % to about 20 wt %; an exemplary weight ratio of disintegration agent to 3,4-DAP is in the range of about 1:5 to about 1:10. Exemplary concentrations of antioxidant are between about 1 wt % and about 3 wt %; an exemplary weight ratio of antioxidant to 3,4-DAP is in the range of about 1:5 to 1:30. In one example, ascorbic acid is the antioxidant and is used at a ratio to 3,4-DAP of less than 1:1, e.g. 1:2 or less, or 1:10 or less. Exemplary concentrations of lubricant in a stable tablet formulation are between about 0.1 wt % and about 5 wt %; an exemplary weight ratio of lubricant to 3,4-DAP is in the range of about 1:25 to 1:65.

The stable formulations may be provided, e.g. as tablets or pills or capsules in HDPE bottles provided with a desiccant capsule or pouch; or in foil-on-foil blister packaging, or in blister packaging comprising see-through polymer film, if commercially desirable.

Treatment of 3,4-DAP-Responsive Diseases

Hyperphenylalaninemia, Neuropsychological or Neuropsychiatric Disorders

The methods provided herein can be used for treatment of 3,4-DAP responsive conditions, including myasthenia gravis and myasthenic syndromes (including Lambert-Eaton myasthenic syndrome, congenital myasthenia, and myasthenic syndromes of medicinal or toxic origin), improving the cognitive functions during aging, treatment of fatigue related to a neurological pathology, diseases affecting motor neuron cells, such as acute infectious poliomyelitis and its effects, Creutzfeldt-Jakob syndrome, some toxic and nutritional disorders, such as those related to vitamin B deficiency, degeneration of motor neurons as a result of exposure to certain compounds, such as aluminum, or degenerative diseases, such as amyotrophic lateral sclerosis, primary lateral sclerosis, pre-senile dementia with attack on motor neurons, spinal muscular atrophies, olivoponto-cerebellar atrophy, Joseph's disease, Parkinson's disease, Huntington's chorea or Pick's disease.

The amount of 3,4-DAP needed varies considerably between individuals. Dosages of about 15 mg per day to about 60 mg per day have been described.

In exemplary embodiments, it is contemplated that the methods provided herein will provide to a patient in need thereof, a daily dose of between about 2.5 mg per day and 180 mg per day of 3,4-DAP. This dose is adjusted up or down depending on the efficacy being achieved by or the side effect(s) observed with the administration. The daily dose may be administered in a single dose or alternatively may be administered in multiple doses at conveniently spaced intervals. In exemplary embodiments, the daily dose may be 2.5 mg per day, 3 mg per day, 5 mg per day, 7.5 mg per day, 9 mg per day, 10 mg per day, 12 mg per day, 12.5 mg per day, 15 mg per day, 20 mg per day, 25 mg per day, 30 mg per day, 35 mg per day, 40 mg per day, 45 mg per day, 50 mg per day, 55 mg per day, 60 mg per day, 65 mg per day, 70 mg per day, 75 mg per day, 80 mg per day, 85 mg per day, 90 mg per day, 95 mg per day, 100 mg per day, 105 mg per day, 110 mg per day, 115 mg per day, 120 mg per day, 125 mg per day, 130 mg per day, 135 mg per day, 140 mg per day, 145 mg per day, 150 mg per day, 155 mg per day, 160 mg per day, 165 mg per day, 170 mg per day, 175 mg per day, or 180 mg per day.

It is understood that the suitable dose of a 3,4-DAP will depend upon the age, health and weight of the recipient, kind of concurrent treatment, if any, frequency of treatment, and the nature of the effect desired (i.e., the amount of decrease in side effects desired or the increase in efficacy desired) in addition to a subject's fast or slow metabolizer status. The frequency of dosing also is dependent on pharmacodynamic effects.

The frequency of 3,4-DAP dosing will depend on its pharmacokinetic parameters and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435 1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors, including the individual's status as a fast or slow acetylator. As studies are conducted, further information will emerge regarding appropriate dosage levels and duration of treatment for specific diseases and conditions.

EXAMPLES

It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example A

Bioavailability/Bioequivalence Study

Objectives

The primary objectives of the study were to evaluate the clinical tolerance of a single 10 mg dose (equivalent base) oral intake of 3,4-DAP salt in five healthy subjects and to determine the relative bioequivalence of a single 20 mg oral dose of 3,4-DAP administered as a salt or as a free base to 26 healthy subjects. The secondary objectives were to study pharmacokinetic parameters (elimination half and elimination constant), to compare the biological tolerance of both a 20 mg oral intake of 3,4-DAP as a free base and as a salt, and to measure QTcf intervals at expected $C_{max}$.

Overall Study Plan

Tolerance Evaluation:

This was an open and uncontrolled study of the clinical tolerance to a low dose of the phosphate salt. Subjects were hospitalized from 8 am to 4 pm after fasting since midnight the previous night. At 8:30 am, one 10 mg 3,4-DAP phosphate tablet was administered with a glass of water in the presence of a supervising nurse. During their 8-hour stay, heart rate was continuously monitored, blood pressure was measured on eight occasions (including baseline) and three urine samples were taken.

Bioequivalence Study:

This was a double-blind, randomized 2-way cross-over trial. The two administration periods were separated by a wash-out of at least 3 days and not more than 10 days. At the beginning of each period, subjects were hospitalized at 8 am (while fasting since midnight) for at least 12 hours. At their arrival a urinary sample was taken and avenous catheter was inserted into an antecubital vein. A first blood sample was drawn 15 min before drug intake. At around 8:30 am drug was administered (as the phosphate salt or free base according to randomization) with a glass of water under the supervision of a nurse and subjects remained seated for 15 min. Group A received two 10 mg tablets of 3,4-DAP phosphate. Group B received two 10 mg capsules of 3,4-DAP as a free base.

Two 5 mL blood samples were drawn at the following times after drug administration: 5 min, 10 min, 15 min, 20 min, 30 min, 45 min, 60 min, 75 min, 90 min, 120 min, 240 min, 360 min, 480 min, and 660 min. At each sampling time two 5 mL samples were drawn on $Li^{2+}$ heparinized tubes. They were immediately centrifuged at room temperature. Serum was then separated and dispatched into three clearly identified aliquots which were frozen at −20° C. Two aliquots were used for drug assay and one was kept in the hospital ward.

Urine was collected at dosing and between 0-4 hours after dosing, between 4-8 hours after dosing, and between 8-11 hours after dosing. Subjects were then discharged from the hospital and instructed to collect their urine at home from between 11-24 hours after dosing. Urine was sampled in tubes without conservative. Total volume was noted and two 10 mL samples were frozen at −20 C (one used for dosages and one kept in the hospital).

12-lead ECGs (50 mm/s, 2 cm/mV) were recorded over 1 minute three times prior to drug intake (HR-RR, QT and QTcf were averaged to determine baseline values) and then at 15, 20, 30, 45, 60, 75, 90, 120, and 240 min post dose. ECG parameters were recorded by using Cardionics™ ECG/VCG software (version 3.3.0). Blood pressure was measured at 120 min post dosing.

Subjects remained fasting up to 4 hours post dosing when a standard lunch was provided. Adverse events were spontaneously notified and subjects were discharged at around 8 pm with an appropriate device for urine sampling for between 11-24 hours post dosing. The following day, subjects were required to return to the hospital at 8 am for clinical examination, recording of any adverse event and final blood sampling at 24 hours post dose.

An HPLC-electrochemical detection system was used to assay 3,4-DAP in serum samples. The serum samples were prepared by solid phase extraction (SPE). The eluate from SPE was evaporated under nitrogen and the sample was reconstituted with water acetonitrile (50/50 v/v). The extracted sample was analyzed by HPLC coupled with coulometric detection. Two Zorbax SB-CN Interchim columns (250 mm×4.6 mm, 5 μm), mounted in series, were used to chromatograph the sample. Results were specific and accurate for 3,4-DAP with the linearity documented within 5.0-150 ng/mL concentration range. The quantitation limit is 5.0 ng/mL.

Results

The following pharmacokinetic parameters were calculated from the individual plasma concentration versus time profiles: $AUC_{0-t}$, $AUC_{0-inf}$, % AUC, $C_{max}$, $T_{max}$, $t_{1/2}$, and $\lambda_z$.

3,4-DAP either administered as a phosphate salt or as a free base is a highly variable drug with coefficient of variations largely exceeding 30% for AUCs and $C_{max}$. Half life was always less than 2.6 hours. $C_{max}$ for 3,4-DAP as the phosphate salt ranged from 13 ng/mL to 167 ng/mL demonstrating the variability of maximum plasma concentrations between patients. See FIGS. 16-19b for additional details of the results.

Examples 1-3

Drug and Metabolite Concentrations in Rat, Dog, and Human Hepatocytes Preparation of Cryopreserved and Fresh Hepatocytes The objective of this hepatocyte study was to determine the extent of metabolism, complete metabolic profile and metabolite characterization of amifampridine phosphate in several species with $^{14}$C-amifampridine phosphate for a cross species comparison. The following procedures were used to study the metabolism in rat (Example 1), dog (Example 2), and human hepatocytes (Example 3).

The cryopreserved hepatocytes were removed from storage, quickly thawed in a 37° C. water bath for 1 to 2 min, and transferred to a 50 mL tube containing pre-warmed InVitroGRO HT medium (Celsis Inc., Baltimore). The cell suspension was mixed by gentle inversion and the cells were pelleted by centrifugation at 50 to 75×g for 5 min. The supernatant medium was removed and the cells were resuspended in Williams' Medium E. Hepatocyte viability was assessed by using trypan blue exclusion. Hepatocyte density was determined by counting cells with a hemocytometer and the density was adjusted with Williams' Medium E to achieve a final density of 1,000,000 cells/mL. The fresh hepatocyte suspensions were mixed by gently inverting the container and centrifuged for 4 min to pellet the cells (70 to 75×g for rat and dog hepatocytes; 85 to 90×g for human hepatocytes). The supernatant medium was removed and the cells were resuspended in cold Williams' Medium E. The cell density was then determined using a hemocytometer and the density was adjusted with Williams' Medium E to achieve a final density of 1,000,000 cells/mL. Several incubations with hepatocytes from dogs were also conducted at a cell density of 2,000,000 cells/mL.

Fortification Solution Preparation

Fortification solutions for hepatocyte incubations were prepared by weighing and dissolving $^{14}$C-amifampridine and amifampridine in water to generate 0.1, 1, and 5 mM stock solutions (100,000 dpm/mL). A 10 μL addition of the appropriate fortification solution was used to generate final concentrations of 1, 10, and 50 μM in a 1 mL incubation volume. The radiolabel concentration was 100,000 dpm/mL in the initial incubations with hepatocytes from all species evaluated. In order to evaluate the possibility of low level metabolites, additional incubations with higher concentrations of radioactivity were conducted with rat, dog, and human hepatocytes prepared using 1 mM stock solutions in water to achieve 10 μM and 1,000,000 dpm/mL in the incubation mixtures. Additional experimentation also included dog hepatocytes, incubated with 5 mM stock solutions in water to achieve 50 μM and 1,000,000 dpm/mL in the final incubation mixtures.

Determination of the In Vitro Metabolism of $^{14}$C-Amifampridine from Primary Hepatocyte Suspensions Primary hepatocytes (1×10$^6$ hepatocytes/mL in Williams' Medium E) were incubated with $^{14}$C-amifampridine (1, 10, or 50 μM and 100,000 dpm/mL) at 37° C. in an atmosphere of 5% $CO_2$. Control incubations to monitor for non-enzymatic degradation were conducted at all time points by incubating 10 μM $^{14}$C-amifampridine (100,000 dpm/mL) in the absence of hepatocytes. To ascertain endogenous components present during LC-MS analysis, control incubations were also conducted containing hepatocytes in Williams' Medium E without $^{14}$C-amifampridine present.

The hepatocyte suspension was gently swirled by hand and 1 mL was dispensed into the appropriate well plates. An equal volume of Williams' Medium E was added to the wells for control incubations. The cells were pre-incubated for 15 min on a platform shaker in an incubator set to maintain 37° C. in an atmosphere of 5% $CO_2$. Reactions were initiated by adding 10 μL of concentrated test article solution. Incubations were terminated at 0, 30, 60, 120, and 240 min by adding 2 mL of acetonitrile containing 1% formic acid to the test article incubations (2:1 dilution). For the time-0 incubations, the hepatocyte suspension samples were stopped by adding 2 mL of acetonitrile containing 1% formic acid prior to adding the test article. Samples were vortex mixed, and the protein was removed by centrifugation at 1400×g for 10 min at 4° C. The supernatants (66% acetonitrile/33% media) were transferred to separate tubes and stored at approximately −20° C. until analysis.

In order to evaluate the possibility of low level metabolites, additional incubations were conducted with higher concentrations of radioactivity. $^{14}$C-amifampridine (10 μM and 1,000,000 dpm/mL) was incubated with rat, dog, and human hepatocytes (1×10$^6$ hepatocytes/mL) for 240 min following the procedures above. Dog hepatocytes were also incubated with 50 μM $^{14}$C-amifampridine (1,000,000 dpm/mL) and 2×10$^6$ hepatocytes/mL for 240 min.

Preparation of Samples for Radio-HPLC Analysis

The supernatant samples initially were directly analyzed by the radio-HPLC method presented below:

| HPLC System: Shimadzu System | |
| --- | --- |
| UV wavelength: | 254 nm |
| Radioactivity detector: | Packard 500 Series |
| Cell type: | Time resolved-liquid scintillation counting (TR-LSC ™) |
| Cell volume: | 0.5 mL |
| Scintillation fluid: | Ultima Flo M |
| Scintillation fluid flow rate: | 3 mL/minute |
| Columns: | Waters Atlantis HILIC Silica, 4.6 × 150 mm, 5 μm |
| Guard column: | Waters Atlantis HILIC Silica, 4.6 × 20 mm, 5 μm |
| Column temperature: | 30° C. |
| Injection volume: | 3, 4, or 15 μL |

-continued

| HPLC System: Shimadzu System | |
|---|---|
| Mobile Phase A: | 10 mM ammonium formate, pH 3 |
| Mobile Phase B: | acetonitrile |
| Flow rate: | 1 mL/minute |
| | Time (mins)   Mobile Phase (% A:% B) |
| Gradient: | 0    5:95 |
| | 2    5:95 |
| | 20   50:50 |
| | 25   50:50 |
| | 26   5:95 |
| | 34   5:95 |

Quantitation of Test Article and its Metabolites by Radio-HPLC Analysis

Samples from hepatocyte incubations were analyzed for metabolites of $^{14}$C-amifampridine by radio-HPLC. In the incubations containing 100,000 dpm/mL, due to low analyte peak area to background ratios, all the peaks with an area>5% of total radioactivity in the chromatogram were integrated and were considered to constitute a region of interest (ROI). In the incubations containing 1,000,000 dpm/mL, all the peaks with an area>1% of total radioactivity in the chromatogram were integrated and were considered to constitute the ROI.

Example 1

Drug and Metabolite Concentration in Rat Hepatocytes: Results are described in FIG. 1. M1 is N-(4-aminopyridin-3-yl)acetamide.

Example 2

Drug Concentration in Dog Hepatocytes: Results are described in FIG. 2.

Example 3

Drug and Metabolite Concentration in Human Hepatocytes: Results are described in FIG. 3. M1 is N-(4-aminopyridin-3-yl)acetamide.

Example 4

N-(4-Aminopyridin-3-yl)acetamide Metabolite Production in-vivo: Rat PK Study

The objective of this study was to determine the absolute bioavailability of amifampridine phosphate and the pharmacokinetics of amifampridine and its 3-N-acetyl metabolite upon single-dose IV and single-day oral dose (TID) administration.

Amifampridine phosphate was administered by IV bolus at 0.8 mg/kg (in saline) to 6 rats/sex and by oral gavage (in water) TID (approximately 6 hours apart) at dose levels of 2, 8, and 25 mg/kg/dose (equivalent to 6, 24, and 75 mg/kg/day) to 12 rats/sex/group, with oral Dose 1 given to fasted rats and Dose 2 and 3 with food ad libitum. For IV bolus dose and oral Dose 1 (dose administration No. 1), blood samples were collected from three animals/sex/timepoint at predose and 0.083 (IV only), 0.17, 0.25, 0.33, 0.5, 0.75, 1, 1.25 (IV only), 1.5, 2, 2.5, 3, and 6 hours post-dose; 0.17, 0.5, and 6 hours following the second oral dose (dose administration No. 2); and 0.17, 0.25, 0.33, 0.5, 0.75, 1, 1.5, 2, 3, 4, 6, 8, and 10 hours following the third oral dose (dose administration No. 3). The second and third oral doses were given at 6 and 12 hours, respectively, after the first dose. LC-MS/MS was used to quantify amifampridine, 3-N-acetyl and 4-N-acetyl amifampridine metabolites in rat plasma samples. Due to low concentrations of the 4-N-acetyl metabolite (Cmax<25 ng/mL) detected in plasma, PK analysis was not performed for this metabolite. Noncompartmental analysis was applied to the mean plasma amifampridine and 3-N-acetyl metabolite concentration data for male and female rats.

Figure 4:
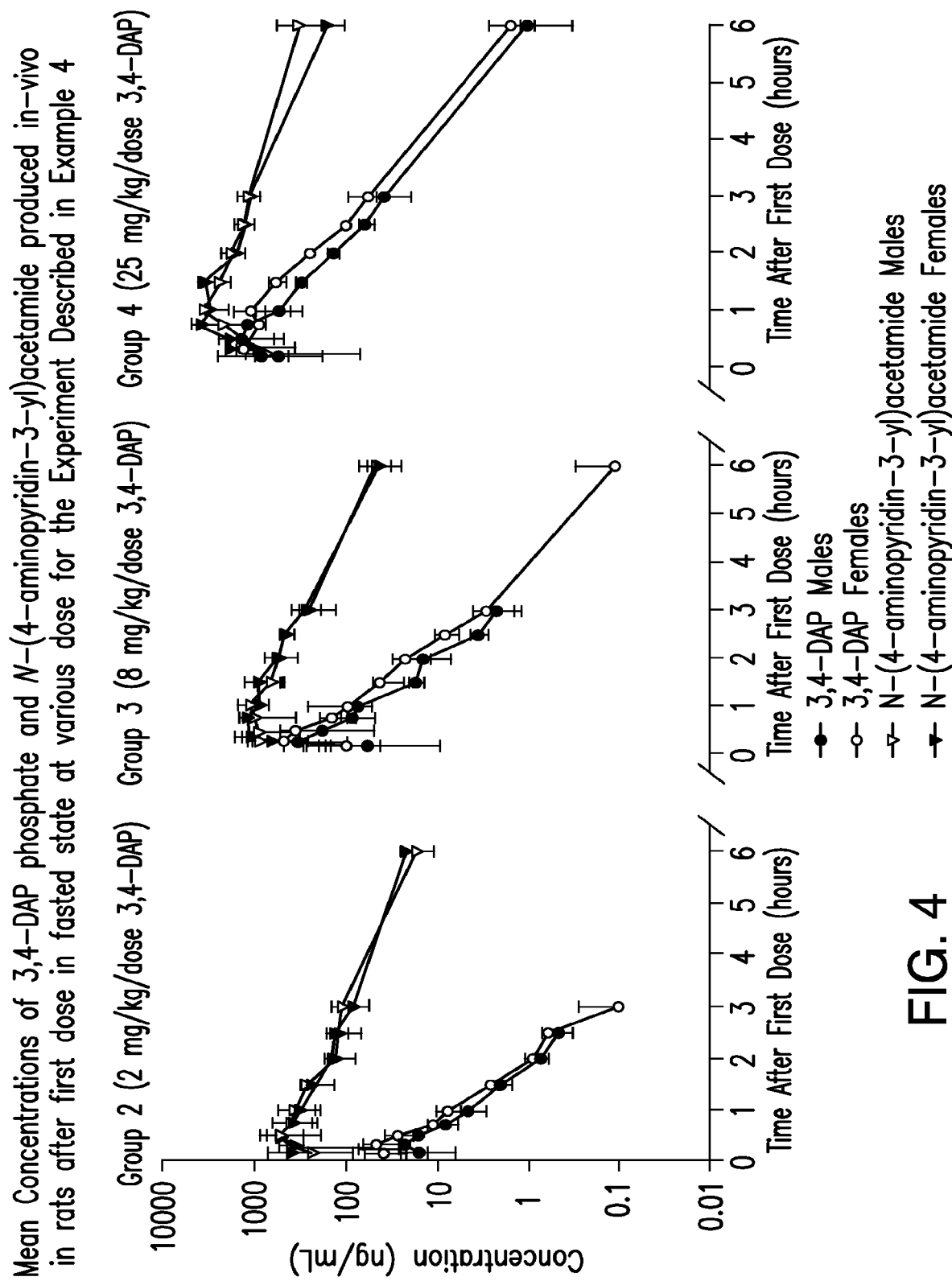
FIG. 4 shows the concentrations of 3,4-diaminopyridine and its metabolite N-(4-aminopyridin-3-yl)acetamide produced in vivo in rats after the first dose in a fasted state at various doses (2, 8, or 25 mg/kg/dose) for the experiment described in Example 4.

Results are described in FIGS. 4 and 5. FIG. 4 depicts the concentration time curve of 3,4-DAP and its metabolite at various doses. FIG. 5 shows the $C_{max}$ and AUC ratios of metabolite to 3,4-DAP phosphate after first dose in a fasted state.

Example 5

In Vitro Inhibitory Activity of 3,4-DAP Phosphate and N-(4-Aminopyridin-3-Yl) Acetamide HCl in CHO Cells Transiently Transfected with hKv1.7

Chemicals used in solution preparation were purchased from Sigma-Aldrich (St. Louis, Mo.), unless otherwise noted, and were of ACS reagent grade purity or higher. Stock solutions of each test article (100.104 mM and 1.00 mM 3,4-DAP phosphate and 100.023 mM and 336.335 mM N-(4-aminopyridin-3-yl)acetamide HCl) were prepared in sterile water, stored refrigerated and used within one day. Test article concentrations were prepared fresh daily by diluting stock solutions into HEPES-buffered physiological saline (HB-PS): 137 mM NaCl; 4.0 mM KCl; 1.8 mM $CaCl_2$; 1 mM $MgCl_2$; 10 mM HEPES; 10 mM Glucose; and adjusted to pH 7.4 with NaOH (prepared weekly and refrigerated). All test article solutions contained 3% sterile water. The test articles were prepared in sufficient volume to run the assay (typically 50 mL).

CHO cells, transiently transfected with hKv1.7, were cryopreserved in 90% FBS and 10% DMSO. Frozen vials of cells were thawed rapidly in a 37° C. water bath. Cells were transferred to a 15 mL conical tube, 10 mL of growth media (Ham's/F12-PS/10% FBS) was added, the suspension was gently mixed and the tube was centrifuged at approximately 250×g for 5 min. The medium was removed, the cell pellet was resuspended in 20 mL of medium, and cells were triturated to disperse cell clumps. For electrophysiology use, 2 mL of the cell suspension was plated in each 35 mm cell culture dish. Recording began 2-3 hours after plating once the cells settled out of the media and adhered to the bottom of the culture dish. For electrophysiological recording, the cell culture media was removed and replaced with continuously flowing vehicle solution.

Cells were transferred to the recording chamber and superfused with vehicle control solution. Pipette solution for whole cell recordings, designed to mimic the intracellular conditions of the CHO cells, was 130 mM potassium aspartate, 5 mM $MgCl_2$, 5 mM EGTA, 4 mM ATP and 10 mM HEPES and adjusted to pH 7.2 with KOH. Pipette solution was prepared in batches, aliquoted, and stored frozen; a fresh aliquot was thawed each day. The recording chamber and vehicle solution were maintained at room temperature. Patch pipettes were made from glass capillary tubing using a P-97 micropipette puller (Sutter Instruments, CA) and were filled with pipette solution. A commercial patch clamp amplifier was used for whole cell recordings. Before digitization, current records were low-pass filtered at one-fifth of the sampling frequency. One or two test article concentrations were applied sequentially (without washout between test substance concentrations) in ascending order, to each cell (n≥2 where n=number of observations). Onset and steady state inhibition of hKv1.7 current due to the test article was measured using a pulse pattern with fixed amplitudes (depolarization: +10 mV amplitude, 300 ms duration) repeated at 10-second intervals from a holding potential of −80 mV. Current amplitude was measured at the end of the step to +10 mV. Current was monitored until a new steady state was achieved. A steady state was maintained for at least 30 seconds before applying the test article. For 3,4-DAP phosphate, concentration-response data were fit to an equation of the form: % Inhibition=$\{1-1/[1+([\text{Test}]/IC_{50})^N]\}*100$ where [Test] is the test article concentration, $IC_{50}$ is the test article concentration at half-maximal inhibition, N is the Hill coefficient, and % Inhibition is the percentage of current inhibited at each test article concentration. Nonlinear least squares fits were solved with the Solver add-in for Excel 2000, or later (Microsoft, WA). The $IC_{50}$ for sustained current was calculated for 3,4-DAP phosphate salt.

For 3,4-DAP phosphate salt, the concentration-response relationship was evaluated at seven concentrations (1, 10, 30, 100, 300, 1000 and 3000 µM) and for N-(4-aminopyridin-3-yl) acetamide HCl salt, the concentration-response relationship was evaluated at three concentrations (100, 1000 and 3000 µM). For N-(4-aminopyridin-3-yl)acetamide HCl salt, testing was also conducted at 10,000 µM (n=2); however, visible precipitate was observed in this formulation and therefore the data was not useable. The concentration-response data are presented in FIG. 20.

Example 6

In Vitro Inhibitory Activity of 3,4-DAP Phosphate and N-(4-aminopyridin-3-yl)acetamide HCl in CHO or HEK293 Cells Transiently Transfected with hKv1.1, hKv1.2, hKv1.3, hKv1.4, hKv1.1, or hKv1.5

The objective of this study was to examine the in vitro effects and determine the $IC_{50}$ of 3,4-DAP phosphate and the metabolite N-(4-aminopyridin-3-yl)acetamide HCl on the following ion channels: cloned human Kv1.1 potassium channel (encoded by the human KCNA1 gene, expressed in HEK293 cells), cloned human Kv1.2 potassium channel (encoded by the human KCNA2 gene, expressed in HEK293 cells), cloned human Kv1.3 potassium channel (encoded by the human KCNA3 gene, expressed in CHO cells), cloned human Kv1.4 potassium channel (encoded by the human KCNA4 gene, expressed in HEK293 cells), cloned human Kv1.5 potassium channel (encoded by the human KCNA5 gene and expressed in CHO cells), responsible for $I_{Kur}$, ultra-rapid delayed rectifier potassium current.

Chemicals used in solution preparation were purchased from Sigma-Aldrich (St. Louis, Mo.), unless otherwise noted, and were of ACS reagent grade purity or higher. Stock solutions of each test article (100 mM, 30 mM and 1.00 mM 3,4-DAP phosphate and 100 mM N-(4-aminopyridin-3-yl) acetamide) were prepared in sterile water and stored refrigerated. Test article concentrations were prepared fresh daily by diluting stock solutions into HEPES-buffered physiological saline (HB-PS): 137 mM NaCl; 4.0 mM KCl; 1.8 mM $CaCl_2$; 1 mM $MgCl_2$; 10 mM HEPES; 10 mM Glucose; and adjusted to pH 7.4 with NaOH (prepared weekly and refrigerated). All test article solutions contained 3% sterile water. The test articles were prepared in sufficient volume to run the assay (typically 10 mL)

HEK293 cells were stably transfected with the appropriate ion channel cDNA encoding the pore-forming channel subunit. Stable transfectants were selected using the G418-resistance gene incorporated into the expression plasmid. Selection pressure was maintained with G418 in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 µg/mL streptomycin sulfate and 500 µg/mL G418. CHO cells were stably transfected with the appropriate ion channel cDNA(s). Cells were cultured in Ham's F-12 supplemented with 10% fetal bovine serum, 100 U/mL penicillin G sodium, 100 µg/mL streptomycin sulfate, and the appropriate selection antibiotics.

Before testing, cells in culture dishes were treated with trypsin. Cells were transferred to a 15-mL conical tube and the tube was centrifuged at approximately 1,300 rpm for 1.5 min. The medium was removed, the cell pellet was resuspended in 10 mL DMEM/F12, and cells were triturated to disperse cell clumps. Cells in suspension were allowed to recover for 10 min in a tissue culture incubator set at 37° C. in a humidified 95% air, 5% $CO_2$ atmosphere. The cells were then centrifuged for 1.5 min at 1,300 rpm. The supernatant was removed, replaced with 10 mL HB-PS, and the cells were gently resuspended. The tube of cells was inverted once or twice before once again being centrifuged for 1.5 min at 1,300 rpm. The supernatant was removed and the pellet was resuspended in ~120 µL HB-PS and transferred to a 1.5 mL Eppendorf tube, which was then loaded onto the PatchXpress machine. The target cell concentration was approximately 8.3 million cells/mL.

Cells were transferred to the recording well and superfused with vehicle control solution. Pipette solution for whole cell recordings, designed to mimic the intracellular conditions of the cells, was 130 mM potassium aspartate, 5 mM $MgCl_2$, 5 mM EGTA, 4 mM ATP and 10 mM HEPES and adjusted to pH 7.2 with KOH. Pipette solution was prepared in batches, aliquoted, and stored frozen; a fresh aliquot was thawed each day. The recording chamber and vehicle solution were maintained at room temperature.

In preparation for a recording session, intracellular solution was loaded into the intracellular compartments of the Sealchip$_{16}$. Cell suspension was pipetted into the extracellular compartments of the Sealchip$_{16}$. After establishment of a whole-cell configuration, membrane currents were recorded using dual-channel patch clamp amplifiers in the PatchXpress®. Before digitization, the current records were low-pass filtered at one-fifth of the sampling frequency.

One or two test article concentrations were applied sequentially (without washout between test substance concentrations) in ascending order, to each cell (n≥2 where n=number of observations). Onset and steady state inhibition of current due to the test article was measured using a pulse pattern with fixed amplitudes (indicated below) repeated at 10-second intervals from a holding potential of −80 mV. A steady state was maintained for at least 30 seconds before applying the test article. Current was monitored throughout the experiment.

| Channel | Voltage Step | Duration | Location of current amplitude measurement |
|---|---|---|---|
| Kv1.1 | +40 mV | 300 ms | Peak current |
| Kv1.2 | +40 mV | 300 ms | Peak current |
| Kv1.3 | +20 mV | 300 ms | End of voltage step |

| Channel | Voltage Step | Duration | Location of current amplitude measurement |
|---|---|---|---|
| Kv1.4 | +20 mV | 200 ms | Peak current |
| Kv1.5 | +20 mV | 300 ms | End of voltage step |

For 3,4-DAP phosphate, concentration-response data were fit to an equation of the form: % Inhibition=$\{1-1/[1+([Test]/IC_{50})^N]\}*100$ where [Test] is the test article concentration, $IC_{50}$ is the test article concentration at half-maximal inhibition, N is the Hill coefficient, and % Inhibition is the percentage of current inhibited at each test article concentration. Nonlinear least squares fits were solved with the Solver add-in for Excel 2000, or later (Microsoft, WA). The $IC_{50}$ for sustained current was calculated for 3,4-DAP phosphate salt.

For 3,4-DAP phosphate, the concentration-response relationship was evaluated at seven concentrations (1, 10, 30, 100, 300, 1000 and 3000 µM) and for N-(4-aminopyridin-3-yl)acetamide HCl, the concentration-response relationship was evaluated at three concentrations (100, 1000 and 3000 µM). The concentration-response data are presented in FIGS. 21a and b.

Example 7

Inhibition of NAT Enzymes with Acetaminophen

Fast acetylators of 3,4-diaminopyridine are expected to have reduced efficacy when compared to slow acetylators of 3,4-diaminopyridine since 3,4-diaminopyridine is metabolized more quickly in fast acetylators. It is therefore useful to inhibit NAT2 in order to increase drug levels in fast acetylators. (See *Pharmacogenetics* 1998, 8(6), 553-9.)

Example 10

Randomized, Open-Label, Two-Treatment, Two-Period Crossover Study to Evaluate the Effect of Food on Relative Bioavailability of Amifampridine Phosphate (3,4-Diaminopyridine Phosphate) in Healthy Subjects Objectives The primary objectives of the study were to compare the effect of food on the relative bioavailability of a single dose of amifampridine phosphate, 2 tablets administered orally, during fasting and fed conditions in healthy subjects. The secondary objective of the study was to assess the safety and tolerability of a single dose of amifampridine phosphate, 2 tablets administered orally, during fasting and fed conditions in healthy subjects.

Overall Study Plan

This was a randomized, open-label, 2-treatment, 2-period crossover study with 44 completed subjects to assess the safety, tolerability, and the effect of food on the relative bioavailability of a single dose of amifampridine phosphate. Each subject received a total of 2 single doses of amifampridine phosphate as follows:

Treatment A: a single dose of amifampridine phosphate consisting of 2 tablets (20 mg active pharmaceutical ingredient; API) administered orally in a fasting state (overnight fast of at least 10 hours)

Treatment B: a single dose of amifampridine phosphate consisting of 2 tablets (20 mg API) administered orally in a fed state (overnight fast of at least 10 hours, followed by a high fat breakfast) 30 min after start of the meal Subjects were randomized 1:1 to receive the 2 doses as follows:

Treatment Group 1: Treatment A then B
Treatment Group 2: Treatment B then A

The study design is presented in the figure below. Potential subjects were screened up to 27 days prior to Check-in for the first study dose. For the Treatment Period 1, subjects resided in the CRU from the afternoon of Day −1 through the morning of Day 2 (approximately 24 hours post dose). Subjects were treated on Day 1. For the Treatment Period 2, subjects were asked to return on the afternoon of Day 7 for Check-in and remain at the CRU through the morning of Day 9 (approximately 24 hours post dose). Subjects were treated on Day 8. A Washout Period of 6 (up to 10) days separated each dose administration, beginning on Day 2. A post study assessment was performed 5 to 7 days after the last dose.

Study Design

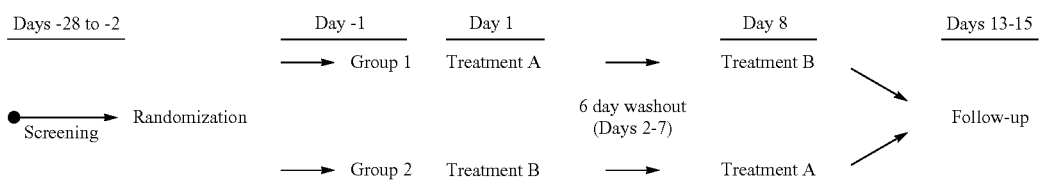

Discussion of Study Design

The randomized, 2-period, 2-sequence crossover design used for the study allowed the dietary status effect to be distinguished from other effects. The study design is well accepted in the assessment of food effects on drug bioavailability and safety. This study design allowed for healthy subjects to cross-over to alternate fed/fasted states allowing for a direct comparison of outcomes.

Selection of Subject Population

Healthy adult volunteers were selected for participation in this study including male or female subjects between the ages of 18 and 65 inclusive, with a body mass index (BMI) between 18.5 and 30 kg/m² inclusive. Good health was evidenced by physical examination, clinical laboratory evaluations (hematology, chemistry, and urinalysis), and electrocardiogram (ECG). Individuals who met the following exclusion criteria were not eligible to participate in this study: subjects using medication that prolongs the QT/QTc interval; subjects who had prior exposure to amifampridine (base or phosphate); subjects with a history palpitations, epilepsy, seizures, unexplained syncopal episodes, arrhythmias, or risk factors for torsade de pointes; subjects who had, or had a history of, any clinically significant neurological, gastrointestinal, renal, hepatic, cardiovascular, psychiatric, respiratory, metabolic, endocrine, hematological, or other major disorders as determined by the investigator; an ECG at Screening that showed any of the following: sinus arrhythmia with unacceptable rate variation (e.g., >20% RR variability), excessive heart rate variation at rest, QTcB interval>450 ms confirmed by a repeat ECG, PR interval>210 ms, QRS interval>120 ms at or under age 35 years or >110 ms over age 35 years, early repolarization pattern that increased the risk of participating in the study, or an abnormality in the 12-lead ECG at Screening that increased the risk of participating in the study.

Treatments and Administration

Treatments Administered

Amifampridine phosphate was provided in tablets containing the equivalent of 10 mg of amifampridine free base. In each treatment period, subjects received a single dose consisting of 2 intact tablets of amifampridine phosphate (equivalent of 10 mg of amifampridine each) administered orally with 240 mL of water. Each tablet contained amifampridine phosphate, microcrystalline cellulose, colloidal anhydrous silica, and calcium stearate. There was no comparator product for this study.

For Treatment A, subjects were administered the dose with 240 mL of water, following an overnight fast of at least 10 hours. No food was allowed for at least 4 hours post dose and no water was allowed for at least 1 hour pre or post dose.

For Treatment B, following an overnight fast of at least 10 hours, subjects consumed a high-fat (approximately 60% of total caloric content of the meal) and high-calorie (800 to 1,000 calories) meal. The meal derived 150 calories from protein, 250 calories from carbohydrate, and 500 to 600 calories from fat. The meal was provided 30 min before dosing, eaten at a steady rate, and was completed approximately 10 min prior to dosing. The IP was administered 30 min after start of the meal and was administered with 240 mL of water. No food was allowed for at least 4 hours post dose.

Subjects received standardized meals scheduled at approximately the same time in each treatment period and water was allowed as desired except for one hour before and after drug administration. Subjects received treatments while in a standing position and were not allowed to lie supine for 2 hours post dose, except for study assessments or if clinically indicated.

Method of Assigning Subjects to Treatment Groups

On Day −1, subjects were randomized to receive 2 single doses of amifampridine phosphate in Treatment Group 1 or Treatment Group 2. Treatment Group 1 received Treatment A then B, while Treatment Group 2 received Treatment B then A.

Treatment A: 2 intact tablets administered orally to subjects in a fasting state.

Treatment B: 2 intact tablets administered orally to subjects in a fed state.

Selection of Doses in the Study

Standard guidelines for food effect bioavailability studies recommended utilizing the highest strength of a drug product intended to be marketed, unless safety concerns warranted use of a lower strength dosage form. Amifampridine phosphate received marketing approval by the European Commission for the symptomatic treatment of patients with LEMS at a maximum single dose of up to 20 mg amifampridine. Safety of a 20 mg dose of amifampridine phosphate is based on nonclinical data and previous human experience in healthy subjects and patients with neurological disorders.

Fasting Conditions

For treatment A, subjects receiving treatments administered under fasting conditions were dosed after they completed a minimum 10-hour overnight fast. The subjects continued to fast for 4 hours post dose. Water was allowed ad lib during the study except for 1 hour prior through 1 hour post-dose.

Subjects received standardized meals scheduled at approximately the same time in each treatment period and water was allowed as desired except for one hour before and after drug administration. Subjects received treatments while in a standing position and were not allowed to lie supine for 2 hours post dose, except for study assessments or if clinically indicated.

Non-Fasting Conditions

For Treatment B, following an overnight fast of at least 10 hours, subjects consumed a high-fat (approximately 60% of total caloric content of the meal) and high-calorie (800 to 1,000 calories) meal. The meal derived 150 calories from protein, 250 calories from carbohydrate, and 500 to 600 calories from fat. The meal was provided 30 min before dosing, eaten at a steady rate, and was completed approximately 10 min prior to dosing. The IP was administered 30 min after start of the meal and was administered with 240 mL of water. No food was allowed for at least 4 hours post dose.

Subjects received standardized meals scheduled at approximately the same time in each treatment period and water was allowed as desired except for one hour before and after drug administration. Subjects received treatments while in a standing position and were not allowed to lie supine for 2 hours post dose, except for study assessments or if clinically indicated.

Duration of Treatment

For the Treatment Period 1, all subjects received a single dose of amifampridine phosphate on Day 1. A Washout Period of 6 days separated each dose administration, beginning on Day 2. For Treatment Period 2, all subjects received a single dose of amifampridine phosphate on Day 8.

Efficacy and Safety Variables

Safety Measurements Assessed

Safety was evaluated for all subjects who take at least one dose of 3,4-DAP. The schedule for these assessments is shown in FIG. 15. Safety was evaluated by recording the incidence of ad dverse events (AEs), physical examination, vital signs, concomitant medications, clinical laboratory assessments, and 12-lead electrocardiogram (ECG).

Pharmacokinetic Measures

Blood samples (approximately 1×6 mL) were taken by venipuncture or cannulation of a forearm vein(s). The samples were collected into lithium heparin Vacutainer™ tubes and, after mixing, were placed in a cool box containing crushed ice/water. Blood samples were centrifuged, within 1 hour of collection, at 1500 g for 10 min at approximately 4° C. For each sample, 1 mL of the separated plasma was transferred into each of two, 5 mL polypropylene tubes, maintained at 0 to 4° C. prior to being stored (within 2 hours of collection) and subsequently stored at approximately −70° C. until quantification by liquid chromatography tandem mass spectrometric (LC-MS/MS) analysis. Collection times and windows for each sample collection time are listed in the following table. Each draw was to be completed, even if collected outside of a given window.

| Plasma Pharmacokinetic Assessment Times and Sampling Windows | |
|---|---|
| Collection Time | Window |
| 90 min prior to dose | ±5 Min |
| 10, 15, 30, 45, 60, 75 min, 1.5, 2, 4, and 6 hours post dose | ±5 Min |
| 8, 10, and 12 hours post dose | ±10 Min |
| 18 and 24 hours post dose | ±15 Min |

Urine samples (≥approximately 40 mL) were collected at the following times and intervals: ≤90 min prior to dose (single sample), 0 to 4 hours, 4 to 8 hours, and 8 to 24 hours post dose to quantify total dose excreted of un-metabolized amifampridine and the major metabolite 3-N-acetyl amifampridine. During each collection period, the containers were stored in a refrigerator at 2 to 8° C. The weight (g) of each urine collection was recorded prior to removal of 2 sub-samples (20 to 25 mL) into suitably labelled polypropylene containers, which were stored within 4 hours of the end of the collection, at approximately −70° C. until quantification by LC-MS/MS. The remaining urine was discarded.

The PK parameters determined for Amifampridine and 3-N-Acetyl Amifampridine were: $AUC_{0-t}$, $AUC_{0-inf}$, % $AUC_{extrap}$, $C_{max}$, $T_{max}$, $t_{1/2}$, $T_{last}$, $\lambda_z$, CL/F, $V_z$/F, Ae, fe, and $CL_R$.

Analytical Methods

Validated LC-MS/MS detection methods for quantifying plasma and urine concentrations of 3,4-DAP and its N-acetyl metabolite are described in Example 17a.

Analysis Populations

The following populations were analyzed in the study. The safety population consisted of all subjects who received at least 1 dose of study drug and had at least 1 post dose safety assessment. The pharmacokinetic population consisted of all subjects who received at least 1 dose of study drug and had evaluable PK data.

Statistical Methodology

Summary statistics and statistical analysis of the PK data were performed for all subjects who received at least one dose of study drug and had evaluable PK data. For continuous data, summary statistics included the arithmetic mean, arithmetic standard deviation (SD), median, minimum, maximum, and N; for log-normal data (e.g. all PK parameters, excluding $T_{max}$, $T_{last}$, and % $AUC_{extrap}$), the geometric mean and geometric percent coefficient of variation (CV %) are also presented. For categorical data, frequency count and percentages are presented. For the calculation of summary statistics and statistical analysis, unrounded data are used.

Baseline measurement was defined as the last non-missing measurement prior to Period 1 study drug administration. Mean change from baseline was the mean of all individual subjects' change from baseline values. Each individual change from baseline was calculated by subtracting the individual subject's baseline value from the value at the time point. The individual subject's change from baseline value was used to calculate the mean change from baseline using a SAS procedure such as Proc Univariate. Data analysis was performed using SAS® Version 9.2.

Pharmacokinetic Analysis $AUC_{0-inf}$, $AUC_{0-t}$, and $C_{max}$ were subject to statistical analysis by fed/fasted status. These PK parameters were log-transformed (base e) prior to analysis and were analyzed using a mixed model. The model included sequence, period, and treatment as fixed effects and subject as a random effect. For these parameters, least squares (LS) means were calculated for the fed and fasted treatments. Mean differences between the fed and fasted treatments were calculated. The residual variance from the mixed model was used to calculate the 90% confidence interval (CI) for the difference between the fed and fasted treatments. These values were back-transformed to give geometric LS means, a point estimate, and 90% CI for the ratio of the fed relative to the fasted treatment.

A food effect on bioavailability was established if the 90% CI for the ratio of population geometric means between fed and fasted treatments was not contained in the equivalence limits of 80 to 125% for $AUC_{0-inf}$, $AUC_{0-t}$, or $C_{max}$.

Safety Measures

Analysis for the following safety parameters was carried out on the Safety Population: AEs which included all AEs, AEs by severity, drug-related AEs, deaths, SAEs, AEs leading to study discontinuation, and most frequent AEs, standard clinical laboratory tests, vital signs, ECG measurements, routine physical examinations, and prior and concomitant medications. The cut-off for frequency of AEs reported was determined based on the data. No formal statistical testing was performed for the safety analyses; only descriptive statistics were provided. Appropriate descriptive statistics for the safety data were determined using SAS Version 9.2.

Adverse Events

AEs were coded according to the Medical Dictionary for Regulatory Activities (MedDRA; Version 13.0). Concomitant medications were coded using the World Health Organization (WHO; Version March 2009) drug dictionary. The occurrence of AEs was assessed continuously from the time the subject signed the VID and consent. The reporting period for non-serious AEs was from the first dose to the final study visit. The investigator determined the severity of each event and the relationship of an AE to the IP and recorded it on the source documents and AE CRF. The nature, time of onset, duration, severity, and relationship to study drug was documented, including documentation of investigator assessment and review. All events were assessed to determine if the AE was serious.

The Investigator determined the severity of each event and the event was recorded on the source documents and AE CRF. A coding of "mild" meant there was no limitation of usual activities, "moderate" meant there was some limitation of usual activities, "severe" meant there was an inability to carry out usual activities.

Any clinically significant abnormalities found during the course of the study were followed up until they returned to normal or could be clinically explained. If a non-serious AE remained unresolved at the conclusion of the study, the investigator, and medical monitor made a joint clinical assessment as to whether continued follow-up of the AE was warranted, and the results of this assessment were documented. Resolution was defined as the return to baseline status or stabilization of the condition with the expectation that it would remain chronic.

The reporting period for AEs that met the criteria of an SAE began from the time of signing the VID and consent form through follow-up or early termination. An SAE is defined as any AE that meets at least one of the following:

Results in death.

Is life threatening, that is, places the subject at immediate risk of death from the event as it occurred.

Requires in-patient hospitalization or prolongation of an existing in-patient hospitalization.

Results in persistent or significant disability or incapacity.

Is a congenital anomaly or birth defect.

Is an important medical event that does not meet any of the above criteria, but may jeopardize the subject or require medical or surgical intervention to prevent one of the outcomes listed above.

Clinical Laboratory Assessments

Blood and urine samples were collected for clinical laboratory evaluations at Screening, prior to dose administration on dosing days and at the follow-up visit or early termination visit. Additional clinical laboratory evaluations were performed at other times when clinically appropriate or if the ongoing review of the data suggested a more detailed assessment of clinical laboratory safety evaluations were required. The investigator performed a clinical assessment of all clinical laboratory data and each clinically significant laboratory result was recorded as an AE.

The clinical laboratory evaluations performed are listed in the following table.

| Clinical Laboratory Evaluations | | | |
|---|---|---|---|
| Blood Chemistry | Hematology | Urine Tests | Other |
| Albumin | Hemoglobin | Appearance | Thyroid panel: |
| Alkaline phosphatase | Hematocrit | Color | TSH |
| ALT (SGPT) | WBC count | pH | Free T3 |
| AST (SGOT) | RBC count | Specific gravity | Free T4 |
| Direct bilirubin | Platelet count | Ketones | Serology: |
| Total bilirubin[a] | Differential cell count | Protein | HIV antibodies |
| BUN | | Glucose | Hepatitis C antibody |
| Calcium | | Bilirubin | HBsAg |
| Chloride | | Nitrite | Hormonal panel:[b,d] |
| Total cholesterol | | Urobilinogen | Estradiol |
| $CO_2$ | | Hemoglobin | FSH |
| Creatinine | | Pregnancy test[c,d] | hCG |
| Glucose | | | |
| GGT | | | |
| LDH | | | |
| Phosphorus | | | |
| Potassium | | | |
| Total protein | | | |
| Sodium | | | |
| Uric acid | | | |

[a]Direct bilirubin was analyzed only if total bilirubin was elevated.
[b]Analyzed at Screening only and was analyzed at other time points if considered necessary.
[c]Suspected false positive result resulted in serum hormone panel.
[d]Females only.

Vital Signs

Supine systolic and diastolic blood pressure, supine heart rate, respiration, and oral body temperature were measured at Screening, ≤90 min prior to dose, post dose at 0.5, 1, 2, 4, 8, and 24 hours, and at the Follow-up Visit or Early Termination Visit. Clinically significant changes from baseline vital signs were reported as AEs.

Electrocardiography

Single, resting 12-lead ECGs with a 10-second rhythm strip were conducted at Screening, Days 1 and 8 at ≤90 min pre dose and approximately 30 (±5) min post dose (estimated $T_{max}$), and when judged to be clinically appropriate. ECGs were conducted after subjects had been supine for ≥5 min. The ECG machine computed the PR and QT intervals, QRS duration, and heart rate. The QT interval was corrected for heart rate (QTc) using Bazett's formula (QTcB). A physician performed a clinical assessment of each 12-lead ECG. Clinically significant changes from baseline (Day 1 pre dose) were recorded as AEs.

Appropriateness of Measurements

All measurements performed relating to bioavailability of the IP relative to fed and fasting states were standard measurements. Standard PK and safety assessments were performed.

Example 11

Safety Results from Example 10

Single oral doses of 20 mg amifampridine phosphate were considered to be safe and well tolerated when administered to healthy male and female subjects in the fed and fasted state in this study with no SAEs or discontinuations related to amifampridine phosphate. The majority of AEs reported were mild in severity and resolved without treatment. In total, 50 of the 93 (54%) AEs reported were paraesthesias and these are well known side-effects of amifampridine treatment. The incidence of AEs was similar between the fed (24 subjects) and fasted (23 subjects) groups, although there was a higher frequency of AEs in the fasted group (61 fasted AEs vs. 40 fed AEs). There were no clinically significant findings in any clinical laboratory evaluations, vital signs, 12-lead ECG, or physical examination.

The overall incidence of treatment emergent AEs are summarized by fed/fasted status in the following table.

| Summary of Treatment-Emergent Adverse Events by Fed/Fasted Status | | | |
|---|---|---|---|
| | Number of Subjects (%) with Adverse Events [Number of Adverse Events] | | |
| | Fasted (N = 45) | Fed (N = 46) | Overall (N = 47) |
| Subjects with Adverse Events | 24 (53%) | 23 (50%) | 31 (66%) |
| Number of Adverse Events | 61 | 40 | 101 |
| Subjects with serious adverse events | | | |
| Total Subjects discontinued due to adverse events | 0 (0%) [0] | 0 (0%) [0] | 0 (0%) [0] |
| Total All treatment emergent adverse events | 0 (0%) [0] | 1 (2%) [1] | 1 (2%) [1] |
| Total | 24 (53%) [61] | 23 (50%) [40] | 31 (66%) [101] |
| Mild | 24 (53%) [60] | 22 (48%) [38] | 30 (64%) [98] |

Summary of Treatment-Emergent Adverse Events by Fed/Fasted Status

| | Number of Subjects (%) with Adverse Events [Number of Adverse Events] | | |
|---|---|---|---|
| | Fasted (N = 45) | Fed (N = 46) | Overall (N = 47) |
| Moderate | 1 (2%) [1] | 1 (2%) [1] | 2 (4%) [2] |
| Severe | 0 (0%) [0] | 1 (2%) [1] | 1 (2%) [1] |
| Possibly or probably related adverse events | | | |
| Total | 21 (47%) [56] | 21 (46%) [37] | 30 (64%) [93] |
| Mild | 21 (47%) [55] | 21 (46%) [37] | 30 (64%) [92] |
| Moderate | 1 (2%) [1] | 0 (0%) [0] | 1 (2%) [1] |
| Severe | 0 (0%) [0] | 0 (0%) [0] | 0 (0%) [0] |

N, number of subjects studied.

The incidence and frequency of treatment emergent AEs are listed by fed/fasted status in the following table.

Incidence of Treatment Emergent Adverse Events by Fed/Fasted Status (Drug-Related)

| System Organ Class MedDRA Preferred Term | Number of Subjects with Adverse Events [Number of Adverse Events] | | |
|---|---|---|---|
| | Fasted (N = 45) | Fed (N = 46) | Overall (N = 47) |
| Nervous System Disorders | | | |
| Total | 21 (47%) [43] | 17 (37%) [31] | 27 (57%) [74] |
| Paraesthesia Oral | 13 (29%) [15] | 13 (28%) [15] | 20 (43%) [30] |
| Paraesthesia | 10 (22%) [12] | 7 (15%) [8] | 12 (26%) [20] |
| Dizziness | 5 (11%) [5] | 2 (4%) [2] | 5 (11%) [7] |
| Hypoaesthesia Oral | 3 (7%) [3] | 3 (7%) [3] | 5 (11%) [6] |
| Headache | 4 (9%) [4] | 1 (2%) [1] | 5 (11%) [5] |
| Dysgeusia | 1 (2%) [1] | 2 (4%) [2] | 2 (4%) [3] |
| Hypoaesthesia | 2 (4%) [2] | 0 (0%) [0] | 2 (4%) [2] |
| Hypoaesthesia Facial | 1 (2%) [1] | 0 (0%) [0] | 1 (2%) [1] |
| Gastrointestinal Disorders | | | |
| Total | 7 (16%) [10] | 2 (4%) [2] | 9 (19%) [12] |
| Nausea | 3 (7%) [3] | 1 (2%) [1] | 4 (9%) [4] |
| Abdominal Pain | 3 (7%) [3] | 0 (0%) [0] | 3 (6%) [3] |
| Abdominal Pain Upper | 2 (4%) [2] | 0 (0%) [0] | 2 (4%) [2] |
| Abdominal Tenderness | 1 (2%) [1] | 0 (0%) [0] | 1 (2%) [1] |
| Constipation | 0 (0%) [0] | 1 (2%) [1] | 1 (2%) [1] |
| Diarrhoea | 1 (2%) [1] | 0 (0%) [0] | 1 (2%) [1] |
| General Disorders and Administration Site Conditions | | | |
| Total | 2 (4%) [2] | 3 (7%) [3] | 5 (11%) [5] |
| Fatigue | 1 (2%) [1] | 3 (7%) [3] | 4 (9%) [4] |
| Feeling Hot | 1 (2%) [1] | 0 (0%) [0] | 1 (2%) [1] |
| Skin and Subcutaneous Tissue Disorders | | | |
| Total | 1 (2%) [1] | 0 (0%) [0] | 1 (2%) [1] |
| Acne | 1 (2%) [1] | 0 (0%) [0] | 1 (2%) [1] |
| Vascular Disorders | | | |
| Flushing | 0 (0%) [0] | 1 (2%) [1] | 1 (2%) [1] |
| Total | 0 (0%) [0] | 1 (2%) [1] | 1 (2%) [1] |
| Overall Total | 21 (47%) [56] | 21 (46%) [37] | 30 (64%) [93] |

MedDRA, Medical Dictionary for Regulatory Activities;
N, number of subjects studied.

The overall incidence of treatment emergent AEs are summarized by gender in the following table. The incidence of AEs was higher in female subjects with 12 of 16 subjects (75%) reporting an AE compared to 19 of 31 (61%) male subjects.

Summary of Treatment-Emergent Adverse Events by Gender

| | Number of Subjects (%) with Adverse Events [Number of Adverse Events] | | |
|---|---|---|---|
| | Male (N = 31) | Female (N = 16) | Overall (N = 47) |
| Subjects with Adverse Events | 19 (61%) | 12 (75%) | 31 (66%) |
| Number of Adverse Events | 58 | 43 | 101 |
| Subjects with serious adverse events | | | |
| Total | 0 (0%) [0] | 0 (0%) [0] | 0 (0%) [0] |
| Subjects discontinued due to adverse events | | | |
| Total | 1 (3%) [1] | 0 (0%) [0] | 1 (2%) [1] |
| All treatment emergent adverse events | | | |
| Total | 19 (61%) [58] | 12 (75%) [43] | 31 (66%) [101] |
| Mild | 18 (58%) [57] | 12 (75%) [41] | 30 (64%) [98] |
| Moderate | 0 (0%) [0] | 2 (13%) [2] | 2 (4%) [2] |
| Severe | 1 (3%) [1] | 0 (0%) [0] | 1 (2%) [1] |
| Possibly or probably related adverse events | | | |
| Total | 18 (58%) [51] | 12 (75%) [42] | 30 (64%) [93] |
| Mild | 18 (58%) [51] | 12 (75%) [41] | 30 (64%) [92] |
| Moderate | 0 (0%) [0] | 1 (6%) [1] | 1 (2%) [1] |
| Severe | 0 (0%) [0] | 0 (0%) [0] | 0 (0%) [0] |

N, number of subjects studied.

Incidence of Treatment Emergent Adverse Events by Gender (Drug-Related)

| System Organ Class MedDRA Preferred Term | Number of Subjects with Adverse Events [Number of Adverse Events] | | |
|---|---|---|---|
| | Male (N = 31) | Female (N = 16) | Overall (N = 47) |
| Nervous System Disorders | | | |
| Total | 17 (55%) [43] | 10 (63%) [31] | 27 (57%) [74] |
| Paraesthesia Oral | 13 (42%) [18] | 7 (44%) [12] | 20 (43%) [30] |
| Paraesthesia | 6 (19%) [11] | 6 (38%) [9] | 12 (26%) [20] |
| Dizziness | 1 (3%) [2] | 4 (25%) [5] | 5 (11%) [7] |
| Hypoaesthesia Oral | 4 (13%) [5] | 1 (6%) [1] | 5 (11%) [6] |
| Headache | 2 (6%) [2] | 3 (19%) [3] | 5 (11%) [5] |
| Dysgeusia | 2 (6%) [3] | 0 (0%) [0] | 2 (4%) [3] |
| Hypoaesthesia | 1 (3%) [1] | 1 (6%) [1] | 2 (4%) [2] |
| Hypoaesthesia Facial | 1 (3%) [1] | 0 (0%) [0] | 1 (2%) [1] |
| Gastrointestinal Disorders | | | |
| Total | 4 (13%) [4] | 5 (31%) [8] | 9 (19%) [12] |
| Nausea | 2 (6%) [2] | 2 (13%) [2] | 4 (9%) [4] |
| Abdominal Pain | 1 (3%) [1] | 2 (13%) [2] | 3 (6%) [3] |
| Abdominal Pain Upper | 1 (3%) [1] | 1 (6%) [1] | 2 (4%) [2] |
| Abdominal Tenderness | 0 (0%) [0] | 1 (6%) [1] | 1 (2%) [1] |
| Constipation | 0 (0%) [0] | 1 (6%) [1] | 1 (2%) [1] |
| Diarrhoea | 0 (0%) [0] | 1 (6%) [1] | 1 (2%) [1] |

-continued

Incidence of Treatment Emergent Adverse Events by Gender (Drug-Related)

| System Organ Class | Number of Subjects with Adverse Events [Number of Adverse Events] | | |
|---|---|---|---|
| MedDRA Preferred Term | Male (N = 31) | Female (N = 16) | Overall (N = 47) |
| General Disorders and Administration Site Conditions | | | |
| Total | 3 (10%) [3] | 2 (13%) [2] | 5 (11%) [5] |
| Fatigue | 2 (6%) [2] | 2 (13%) [2] | 4 (9%) [4] |
| Feeling Hot | 1 (3%) [1] | 0 (0%) [0] | 1 (2%) [1] |
| Skin and Subcutaneous Tissue Disorders | | | |
| Total | 1 (3%) [1] | 0 (0%) [0] | 1 (2%) [1] |
| Acne | 1 (3%) [1] | 0 (0%) [0] | 1 (2%) [1] |
| Vascular Disorders | | | |
| Flushing | 0 (0%) [0] | 1 (6%) [1] | 1 (2%) [1] |
| Total | 0 (0%) [0] | 1 (6%) [1] | 1 (2%) [1] |
| Overall Total | 18 (58%) [51] | 12 (75%) [42] | 30 (64%) [93] |

MedDRA, Medical Dictionary for Regulatory Activities;
N, number of subjects studied.

Study drug-related AEs in the nervous system disorders system organ class had the highest incidence (27 subjects; 57%) and frequency (74 events). The second highest incidence (9 subjects; 19%) and frequency (12 events) of AEs was in the gastrointestinal disorder system organ class. The most frequently reported AEs considered as being drug-related were paraesthesias; oral paraesthesia (30 events) and paraesthesia (20 events); dizziness (7 events); oral hypoaesthesias (6 events); headache (5 events); fatigue (4 events); nausea (4 events); dysgeusia (3 events) and abdominal pain (3 events). Hypoaesthesia and upper abdominal pain were the only other AEs possibly related to amifampridine treatment that was reported by more than 1 subject in the study.

In total, 50 (54%) of the 93 AEs were paraesthesias and these are well known side effects of amifampridine treatment. All reported incidences of paraesthesia and hypoaesthesia were mild and were considered as possibly related to the administered treatment by the investigator. Overall, most drug-related AEs were transitory and mild, and all subjects recovered from the AE.

The incidence of drug-related AEs was identical in the fed and fasted groups (21 subjects). However, the frequency of AEs was higher in the fasted group (56 events) than the fed (37 events). Oral paraesthesia was similarly prevalent in the fed and fasted groups; paraesthesia was more frequently reported in the fasted group (12 events) than the fed (8 events). Incidence and frequency of oral hypoaesthsia was identical in the fed and fasted groups (3 events). Hypoaesthesia (2 events) and facial hypoaesthesia (1 event) were only reported by subjects in the fasted group.

Nervous system disorders had a higher incidence and frequency in the fasted state (21 subjects; 43 events) than in the fed (17 subjects, 31 events) state. In addition to paresthesias, headache and dizziness were more common in the fasted state. Dysguesia was the only adverse event more frequent in the fed state. Gastrointestinal disorders had a higher incidence and frequency in the fasted state (7 subjects; 10 events) than the fed (2 subjects; 2 events). Abdominal pain, nausea, upper abdominal pain, abdominal tenderness and diarrhea were all more commonly reported by subjects following administration of the study drug in the fasted state.

In general, there was a higher incidence of drug-related AEs in females (75%) than males (58%). Incidences of peripheral paraesthesia were higher in female subjects (38%) than males (19%), and gastrointestinal disorders were also more common in females (31%) than males (13%).

Only 1 AE of moderate severity was reported during the study as being possibly related to the study drug. One subject experienced an AE of headache in Period 2 (fasted treatment) 4 and a half hours after study drug administration. The AE lasted for approximately 8 hours and required treatment with one oral dose of paracetamol (1 g).

There were no deaths or SAEs during this study.

Example 12

Pharmacokinetics Results from Example 10

Pharmacokinetics of Amifampridine Following Administration in the Fasted and Fed State Mean plasma concentrations (+SD) of Amifampridine and 3-N-Acetyl Amifampridine of patients in fed state following oral administration of Amifampridine Phosphate are given in FIG. 6. Mean plasma concentrations (+SD) of Amifampridine and 3-N-Acetyl Amifampridine of patients in fasted state following oral administration of Amifampridine Phosphate are given in FIG. 7. 3,4-DAP Plasma Levels at 4 Hours Post Dose for Subjects in Fasted State are given in FIG. 8. FIG. 8 depicts 3,4-DAP plasma levels at 4 hours post dose suggesting an emerging bimodal distribution by plasma concentration in fasted subjects. Subjects with a plasma concentration of 3,4-DAP phosphate between 0 and 5 ng/mL are likely to be fast acetylators. Subjects with a plasma concentration of 3,4-DAP phosphate between 10 and 26 ng/mL are likely to be slow acetylators. PK for two patients after a single oral dose of 3,4-DAP in a fasted state is given in FIG. 9.

The mean plasma amifampridine concentration-time profiles for fed and fasted administrations are shown in FIG. 10, indicating that $C_{max}$ is dampened when amifampridine is administered with food. The overall mean PK parameter values for amifampridine exposure ($C_{max}$, $AUC_{0-t}$, $AUC_{0-inf}$, $T_{max}$, $t_{1/2}$, and $\lambda_z$) in fed and fasted states are given in FIG. 11. The mean $C_{max}$ was higher in the fasted state, as were the mean values for $AUC_{0-t}$ and $AUC_{0-inf}$. Mean $t_{1/2}$ was somewhat longer, and inversely, the terminal elimination rate constant $\lambda_z$ was somewhat shorter in the fasted state. Mean $T_{max}$ was shorter in the fasted state compared with the fed state.

Variability in amifampridine mean PK parameters for $C_{max}$ (CVs ranging from 58.2% to 77.1%) and AUC was high (FIG. 11). The high variability was also apparent in the wide individual ranges which tended to span more than 10-fold for $AUC_{0-t}$, $AUC_{0-inf}$ and $C_{max}$ in either the fasted or fed state. Specifically, the individual subject data for $AUC_{0-t}$ ranged from 20.6 to 267 ng·h/mL in the fasted state, and from 8.3 to 282 ng·h/mL for the fed state; and $C_{max}$ ranged from 16.0 to 137 ng/mL in the fasted state and from 2.81 to 132 ng/mL in the fed state. There was less variability in $t_{1/2}$ and $\lambda_z$, which had CVs between 29.2% and 39.0%. Specifically, the individual subject data for $t_{1/2}$ ranged from 1.23 to 4.31 hours in the fasted state and from 0.822 to 3.78 hours in the fed state.

The statistical comparison of pharmacokinetic parameters for amifampridine phosphate is summarized in the following table.

Statistical Comparison of Pharmacokinetic Parameters for Amifampridine Phosphate After Oral Administration of 20 mg of Amifampridine to Healthy Subjects in Fed/Fasted State

| Fed vs. Fasted parameter | Geometric Mean Ratio (%)[a] Fed/Fasted | | |
|---|---|---|---|
| | | 90% Confidence Interval | |
| | Point Estimate | Lower limit | Upper Limit |
| $C_{max}$ | 56.3 | 47.0 | 67.5 |
| $AUC_{0-t}$ | 80.0 | 73.1 | 87.6 |
| $AUC_{0-inf}$ | 82.3 | 76.0 | 89.2 |

[a]Based on analysis of natural-log transformed data.
$AUC_{0-t}$, area under the plasma concentration-time curve from time zero up to the last measurable concentration;
$AUC_{0-inf}$, area under the plasma concentration-time curve from time zero to infinity;
$C_{max}$, maximum observed plasma concentration The extent of exposure based on AUC with geometric mean ratios (fed/fasted) of 80.0% ($AUC_{0-t}$) and 82.3% ($AUC_{0-inf}$) indicates that exposure to amifampridine is decreased approximately 18 to 20% following administration in fed vs. fasted state. The $C_{max}$ geometric mean ratio (fed/fasted) of 56.3% indicates that the maximum plasma concentration was decreased 44% in the presence of food. The associated 90% confidence intervals are 47.0 to 67.5% for $C_{max}$, 73.1 to 87.6% for $AUC_{0-t}$, and 76.0 to 89.2% for $AUC_{0-inf}$ which are all outside of the allowable 80 to 125% equivalence range, indicating an effect of food on amifampridine exposure.

Figure 12:
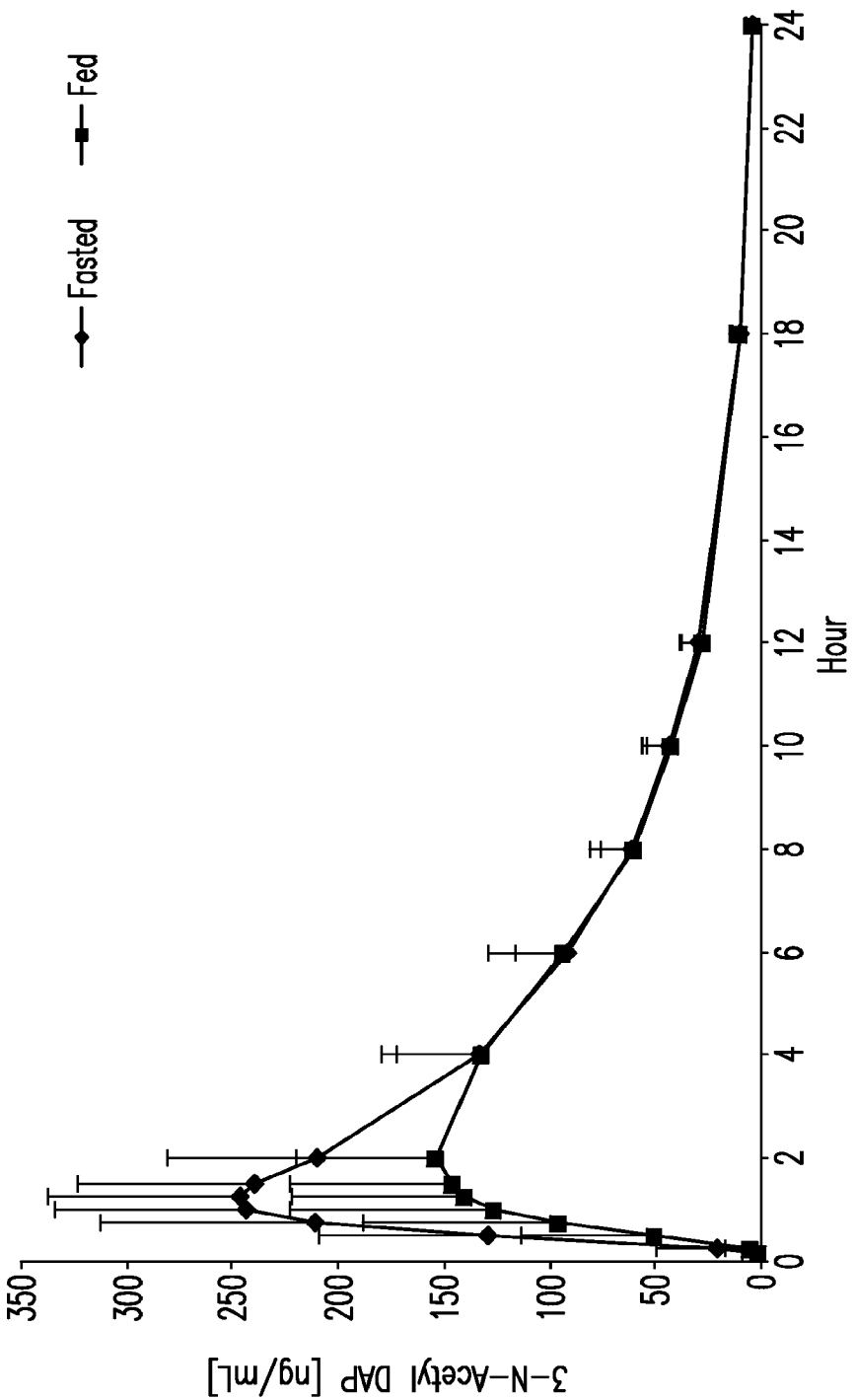
FIG. 12 depicts mean plasma concentrations (+SD) of N-(4-aminopyridin-3-yl)acetamide following oral administration of 3,4-DAP phosphate to all subjects in a fed or fasted state for the clinical trial described in Example 10.
Figure 18A:
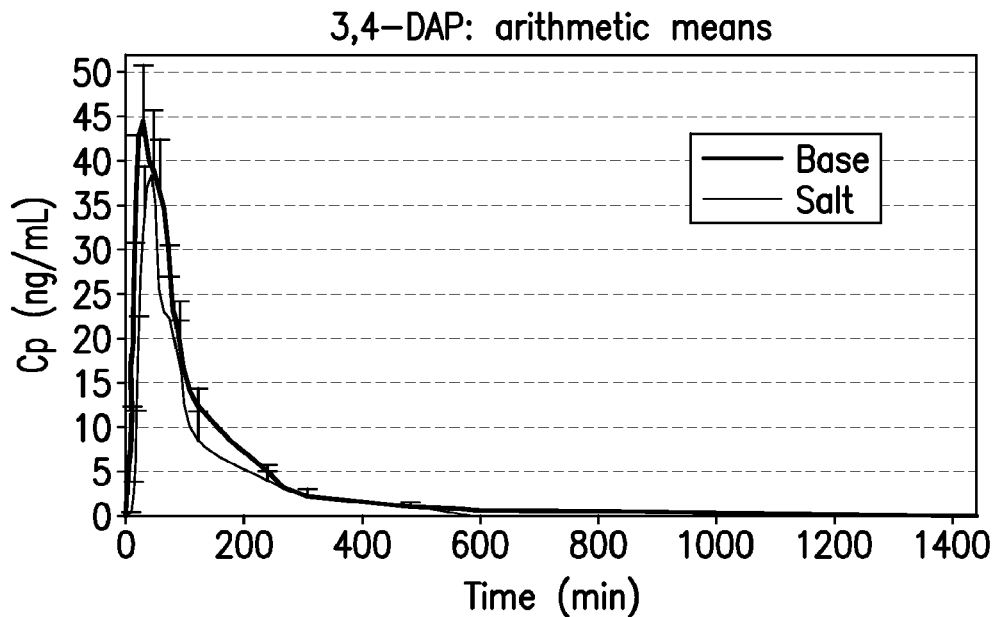
FIGS. 18a and 18b depict 3,4-DAP as phosphate salt or free base: arithmetic means for the clinical trial described in Example A.
Figure 18B:
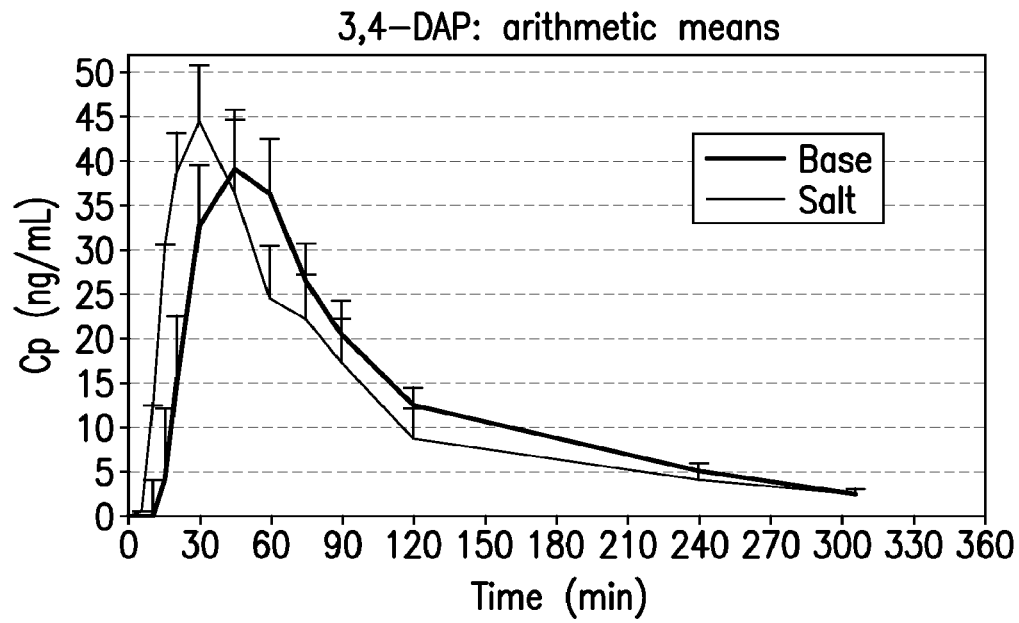

Pharmacokinetics of 3-N-Acetyl Amifampridine Following Administration in the Fasted and Fed States The main plasma metabolite of amifampridine is 3-N-acetyl amifampridine. The concentration-time profiles for appearance of the metabolite in the fed and fasted states are shown in FIG. 12. As observed with amifampridine, the metabolite reached higher $C_{max}$ levels with shorter $T_{max}$ in the fasted state compared to the fed state. The mean PK parameter values for 3-N-acetyl amifampridine exposure ($C_{max}$, $AUC_{0-t}$, $AUC_{0-inf}$, $T_{max}$, $t_{1/2}$ and $\lambda_z$) in fed and fasted states are given in FIG. 13.

The maximal mean plasma concentration ($C_{max}$) of 3-N-acetyl amifampridine was almost 1.5-fold higher in the fasted state compared to the fed state, though there was considerable overlap in the range of data observed in individual subjects. Mean plasma $T_{max}$ was almost 1.7-fold longer in the fed state, but individual data values ranged from 0.75 to 4.0 hours in the fed state and 0.75 to 2.0 hours in the fasted state. Both mean $AUC_{0-t}$ and $AUC_{0-inf}$ for 3-N-acetyl amifampridine were fairly comparable in the fed and fasted states. Overall CVs for PK parameters for the metabolite were smaller than those for the parent compound. Comparison of the mean plasma concentrations of amifampridine and 3-N-acetyl amifampridine in fed and fasted states are shown in FIGS. 6 and 7.

The mean concentration of the major metabolite, 3-N-acetyl amifampridine, was greater than that of amifampridine in plasma in all subjects. Mean metabolite exposure indices were calculated based on ratios of PK parameters for metabolite:parent drug (i.e., 3-N-acetyl amifampridine:amifampridine). For $C_{max}$, the ratio was 4.53 in the fasted state and 4.65 in the fed state, indicating that the maximal concentration of metabolite is approximately 4.5-fold higher than that of parent compound despite influence of food on $C_{max}$. For mean $AUC_{0-t}$, the ratio was 11.6 in the fed state and 12.5 in the fasted state; for mean $AUC_{0-inf}$, 11.2 in the fed state and 12.3 in the fasted state. Thus regardless of effects of food, exposure to metabolite is about 12-fold greater than that to parent compound. The mean plasma elimination t ½ for the 3-N-acetyl metabolite (4.03 hours fed; 4.10 hours fasted) was longer than that for amifampridine (2.28 hours fed; 2.50 hours fasted).

Urinary Excretion

Urinary excretion of amifampridine and 3-N-acetyl amifampridine in fed and fasted subjects is shown in FIG. 14. Urinary excretion data indicated that the fraction of unchanged amifampridine eliminated in the 0 to 24 h urine collection averaged 18.8% (fasted) to 19.2% (fed) of the administered dose. The 3-N-acetyl metabolite was also extensively eliminated in the 0 to 24 h urine and represented 74.0% (fed) to 81.7% (fasted) of the administered dose. The total of parent drug and metabolite eliminated in the 0 to 24 h urine represented 93.2% (fed) to 100% (fasted) of the administered dose. Together these results indicate that a single oral dose of amifampridine is essentially completely excreted in the urine over a 24-hour period as unchanged drug (~19%) and a single major metabolite (~75-80%).

Pharmacokinetic Conclusions

The plasma concentrations of amifampridine and its major metabolite (3-N-acetyl amifampridine) were quantified out to 24 hours in both plasma and urine after single oral doses of 20 mg amifampridine phosphate. Statistically, comparison of key PK parameters ($C_{max}$ and AUC) between the fed and fasted states did not establish comparability. Specifically, the 90% CI of the geometric mean ratios of fed:fasted were 47.0 to 67.5% for $C_{max}$, 73.1 to 87.6% for $AUC_{0-t}$, and 76.0 to 89.2% for $AUC_{0-inf}$. These values fall outside of the standard equivalence limits of 80 to 125%, indicating that there is a significant effect of food on amifampridine exposure.

Overall there is a decrease in exposure of ~40% in $C_{max}$ and ~20% in AUC due to oral administration of amifampridine phosphate in the presence of food. Mean $T_{max}$ is shorter in the fasted state (0.637 hours) than in the fed state (1.31 hours). Together these findings suggest that food slows and decreases absorption of amifampridine phosphate. The delay in $T_{max}$ may be attributed to differences in gastric emptying times in the presence of food delaying the introduction of drug to the duodenum where absorption occurs.

This is the first human study measuring the major metabolite, 3-N-acetyl amifampridine, in addition to the parent compound. 3-N-acetyl amifampridine levels were higher than amifampridine in all subjects, whether fed or fasted. In both the fed and fasted states, $C_{max}$ for 3-N-acetyl amifampridine was approximately 4.5-fold higher and AUC values were approximately 12-fold higher than those for amifampridine. The mean plasma $t_{1/2}$ for the 3-N-acetyl amifampridine was longer than that for amifampridine in both the fed state (4.03 hours for 3-N-acetyl amifampridine vs. 2.28 hours for amifampridine), and fasted state (4.10 hours for 3-N-acetyl amifampridine vs. 2.50 hours for amifampridine). Thus duration and extent of exposure to the metabolite is greater than that of the parent compound. At present, preliminary in-vitro results in cloned K+ channel test systems indicate that the 3-N-acetyl amifampridine metabolite most likely does not inhibit K+ channels up to its solubility limit in the test system.

Urinary excretion data indicate that the fraction of unchanged amifampridine eliminated in the 0 to 24 hour urine collection averaged 19% of the administered dose. The 3-N-acetyl metabolite was extensively eliminated in the 0-24 h urine and represented 74.0% to 81.7% of the administered dose. The mean total of parent drug and metabolite eliminated in the 0-24 h urine represented 93.2% to 100% of the administered dose. Orally administered amifampridine appears to be essentially completely eliminated from the body within 24 hours as the parent compound and a single metabolite.

High inter-individual variability was observed in this food-effect study. The inter-individual CVs for $C_{max}$ and AUC are ~60-70%, with parameters for individual subjects varying over more than a 10-fold range. While acetylator status was not determined in this study, Applicants hypothesized and later demonstrated that the most probable explanation for this variability is the metabolic disposition of amifampridine through a single polymorphic metabolic pathway via N-acetyltransferase enzymes (NAT1 and NAT2). NAT enzymes are recognized to be highly polymorphic in the human population, with recognized slow and fast acetylator phenotypes. It is likely that acetylator status affects the overall PK and disposition of amifampridine.

Discussion and Overall Conclusions

This study investigated the relative bioavailability of a single oral dose of 20 mg amifampridine phosphate when administered to humans in the fed compared to the fasted state. Statistical comparison of key parameters (i.e., $C_{max}$ and AUC) between the fed and fasted states did not establish PK equivalence. Overall there was a decrease in exposure of ~40% in $C_{max}$ and ~20% in AUC when amifampridine phosphate was administered in the presence of food. Observed differences could be due to decreased or delayed absorption at the level of the duodenum from changes in gastric motility (Rowland and Tozer, Clinical Pharmacokinetics, Concepts and Applications, $3^{rd}$ Edition, 1995, Ch 9, Lippincott Williams and Wilkins Publishers). Although the mean $C_{max}$ and AUC PK parameter differences between fed and fasted states are statistically significant, they are less than the variability in these parameters observed between individual subjects within either administration state. While acetylator status was not determined in this study, Applicants show in later studies that this variability is due to the metabolic disposition of amifampridine through a single pathway via NAT enzymes. NAT is recognized to be highly polymorphic in the human population (Hiratsuka M, Kishikawa Y, Tukemura Y, et al. Genotyping of the N-acetyl transferase 2 polymorphism in the prediction of adverse drug reactions to Isoniazid in Japanese patients. Drug Metab Pharmacokin 2002; 17; 357-362), with recognized slow and fast acetylator phenotypes. For instance, 50-59% of the Caucasian population are slow acetylators, while 41-50% are rapid acetylators (Casarett & Doull's Toxicology, The Basic Science of Poisons 7th Ed. (2008) Chapter 6: Biotransformation of Xenobiotics. pp. 278-282). It is possible that acetylator status affects the overall PK and disposition of amifampridine.

Renal excretion accounted for greater than 94% of the orally administered dose eliminated within 24 hours and was represented by unchanged parent drug (~19%) and the 3-N-acetyl metabolite (75-89%). This indicates that there are unlikely to be any other quantitatively significant metabolites and that an oral dose of amifampridine is rapidly excreted. In addition, it suggests that dosage adjustments may be required in patients with renal impairment.

The 3-N-acetyl amifampridine metabolite plasma concentration levels were higher than amifampridine in all subjects in either the fasted or fed states. Overall, AUC exposure to the metabolite was approximately 12-fold higher compared to that of the parent drug.

The metabolite is not predicted to bind or fit into the K+ ion channel. In-vitro studies to evaluate interaction with several K+ ion channels are described in Examples 5 and 6. In fact, the N-acetyl metabolite is not active in several potassium ion channels. (See FIGS. 20, 21a, and 21b.)

Single oral doses of 20 mg amifampridine phosphate were considered to be safe and well tolerated when administered to healthy subjects in the fed and fasted conditions of this study. The majority of AEs reported were mild in severity and resolved without treatment. Only one severe AE resulting in subject withdrawal was reported during the study: an episode of gastroenteritis which was not considered to be related to the study drug by the investigator. There were no SAEs reported during the study. The most frequent AEs were paresthesias, which are well known side effects of amifampridine treatment. The incidence of AEs, in terms of the number of subjects reporting AEs, was similar between the fed and fasted groups, although in terms of number of AEs, there was a higher frequency of AEs in the fasted group (61 fasted, 40 fed).

The variability of amifampridine PK is expected to translate into variations in clinical safety or efficacy and indeed Applicants demonstrated in later examples that frequency of adverse events is correlated to a patient's acetylator status. Efficacy was not evaluated in this study. Despite the range of observed amifampridine and 3-N-acetyl metabolite levels, no related severe or serious AEs were observed in this study. However, more moderate adverse events may be reduced in severity or frequency by determining a patient's acetylation status and dosing amifampridine with or without food as appropriate.

In summary, oral administration of amifampridine phosphate with food has a statistically significant lowering effect on maximal concentration and overall exposure. Amifampridine phosphate was demonstrated to be rapidly absorbed, extensively metabolized, and essentially completely eliminated within 24 hours by the renal route. Overall, these data provide additional information on the bioavailability, PK, and safety of amifampridine phosphate that potentially inform the safe and effective use of amifampridine phosphate in patients.

Example 13

Preparation of 3,4-Diaminopyridine Phosphate

A variety of methods are known in the art for synthesis of 3,4-diaminopyridine, precursors, derivatives and analogs. In addition, it is commercially available from sources such as VWR, ASINEX, and Maybridge. 3,4-DAP phosphate used in the experiments in this application were prepared using procedures similar to or the same as those described in US20040106651 which is included below.

Stage 1) Synthesis of 3,4-DAP Phosphate 90 parts of 3,4-DAP (Aldrich), purified beforehand, and 1800 parts of distilled water are introduced into a reactor. The mixture is brought to a temperature of 75° C. with stirring. Dissolution is observed to be complete. Subsequently, 191 parts of 85% phosphoric acid are slowly introduced into the 3,4-DAP solution. After the addition of the phosphoric acid, the reaction mixture is kept at a temperature of 80° C. for a further 15 min and is then cooled to 35° C. The reaction mixture is then kept at a temperature of between 30 and 35° C. for 4 hours with stirring. The precipitate formed is drained and washed with 100 parts of distilled water and then with 100 parts of absolute ethanol. After drying under vacuum at 60° C. to constant weight, 160 parts of crude 3,4-DAP phosphate are obtained in the form of a white powder, the melting point of which is between 225 and 227° C.

Stage 2) Purification of the Crude 3,4-DAP Phosphate 160 parts of crude 3,4-DAP phosphate obtained above in stage (1), 640 parts of absolute ethanol and 715 parts of distilled water are introduced into a reactor. The mixture is heated, with stirring, to a temperature of 80° C. At this temperature, dissolution is complete. The reaction mixture is subsequently cooled gradually to a temperature of 4° C. and is held at this temperature for 12 hours with stirring. After draining and washing with 100 parts of absolute ethanol, 180 parts of wet product are obtained. The product is subsequently dried at 60° C. under vacuum to constant weight. 133 parts of 3,4-DAP phosphate are then obtained, the melting point of which is 229° C. The elemental analysis of the product thus obtained was carried out on a Perkin-Elmer CHN 4000 device. The product sample was weighed on a balance with an accuracy of 10.sup.−4 mg; the percentage of oxygen was calculated by difference. The elemental analysis of the product obtained, in accordance with that of the expected product, was as follows

| %          | C     | H    | N     | P              | O              |
|------------|-------|------|-------|----------------|----------------|
| Calculated | 28.99 | 4.83 | 20.29 | 14.97          | 30.92          |
| Found      | 29.05 | 4.93 | 20.23 | not determined | not determined |

Example 14

3,4-Diaminopyridine Phosphate Tablet Formulation

Each tablet contained 3,4-diaminopyridine phosphate (equivalent to 10 mg of 3,4-diaminopyridine free base). Each tablet contained about 7.6% (w/w) amifampridine phosphate, about 89.9% (w/w) microcrystalline cellulose, about 0.5% (w/w) colloidal silicon dioxide, and about 2% (w/w) calcium stearate. Acceptable ranges (% weight/weight) are as follows: 3,4-diaminopyridine, 7.00-13.00; microcrystalline cellulose, 89.00-91.00; colloidal silicon dioxide, 0.01-1.00; and calcium stearate, 1.00-3.00.

Example 15

NAT2 Phenotypic Assays

A subject's N-acetyltransferase 2 (NAT2) phenotype can be determined in a number of ways to determine whether the subject is a fast or slow acetylator. The examples given in Examples 15 and 15a, and throughout the specification are exemplary and are not meant to be limiting.

Whether a person has a slow or fast metabolic phenotype can be assessed using ratios of urinary caffeine metabolites. Methods are described in Cascorbi et al, *Am. J. Hum. Genet.*, 57:581-592, 1995 ("Cascorbi") and Jetter et al, *Eur J Pharmacol* (2009) 65:411-417 both of which are incorporated herein by reference in their entireties.

Cascorbi discloses the following method. A patient is given one cup of coffee or half a tablet of caffeine (Coffeinum 0.2 g compretten N). Urine is collected for 5 hours and the pH is adjusted to 3.5 with 80 mmol/L citric acid/phosphate buffer. The prepared urine can be stored at −20° C. until analysis is done. To 0.2 mL of urine saturated with 120 mg ammonium sulfate is added 6 mL chloroform/2-propanol (95:5 v/v) and 0.2 mL chloroform containing 24 μg N-acetyl-4-aminophenol, for example, as an internal standard. The sample is then shaken and centrifuged and the organic phase is lyophilized and resuspended in 1 mL 0.05% acetic acid. The sample is then analyzed by HPLC for the presence of 5-acetylamino-6-formylamino-3-methyluracil (AFMU) and 1-methylxanthine (1×). This can be done on a Beckman ultrasphere octadecylsilane HPLC column with 4 mm internal diameter and 25 cm length and 5 μm particle size (or an analogous column). The detector wavelength is set at 280 nm, the eluent is 0.05% acetic acid/methanol (92:8 v/v), and the flow rate is 1.2 mL/minute (or can be done using analogous conditions). For calibration 1× and AFMU can be added to blank urine samples. Acetylation phenotype is then evaluated by the molar ratio of log(AFMU/1×) where a result of at or below about −0.30 means the person is a slow metabolizer and a result above about −0.30 means the person is a fast metabolizer.

Alternatively, the analytical method described in Jetter et al. *Eur J Clin Pharmacol* 2004, 60:17-21 can be used.

Alternatively, acetylation phenotype can be determined according to the Eidus method using isoniazid as a model drug (Eidus et. al. *Bull World Health Organ* 1973, 49, 507-516; Rychlik-Sych et. al. *Pharmacological Reports* 2006, 58, 2-29). Isoniazid is administered orally at a single dose of 10 mg/kg of body weight. Urine samples are collected 6-8 hours after drug administration. Isoniazid and acetylated isoniazid concentrations are determined spectrophotometrically at 550 nm wavelength. The ratio of extracted acetylisoniazid to a total amount of the extracted isoniazid in urine is calculated as follows: A/(B−A)×0.761 where A is the optical density of an aliquot containing only acetylisoniazid; B is the optical density of an aliquot containing acetylisoniazid and isoniazid artificially converted to acetylisoniazid; and multiplication by 0.761 compensates for the molecular weight of acetylisoniazid and free isoniazid. A value below 3 characterizes a slow acetylator, above 5 as a fast acetylator, and between 3 and 5 as an intermediate acetylator (but is generally categorized as a fast metabolizer).

Alternatively, administration of sulfamethazine, hydralazine, phenyloin, sulfadiazine, and procainamide can be used to determine a person's acetylation status.

Alternatively, a subject's phenotype can be determined using methods described in *Br J Clin Pharmacol.* 2000, 49(3), 240-243 or *Archives of Toxicology* 2005, 79(4), 196-200. A person of ordinary skill in the art would know other methods that could be used to determine a person's NAT1 and NAT2 phenotype.

Example 15a

NAT2 Phenotypic Assay: Caffeine Test used in Example 18

Phenotyping can be accomplished using the following method (Schneider, et. al. *J. Chromatog. B* 2003, 789, 227-237). For the trial in Example 18, subjects emptied their bladders immediately before the administration of a single oral dose of 150 mg caffeine in 240 mL tap water. Subjects had fasted for at least four hours before dosing and fasted for at least one hour after dosing. All urine was collected for a 6 hour period after dosing. Samples were frozen and stored at −20° C. until analysis. The urinary concentration of 1×, AAMU, and 1U were quantified by LC-MS/MS on an Acquity HSS T3 column (100×2.1 mm, 1.8 μm, at 40±1° C., Waters). A mixture of 98% mobile phase A (0.1% formic acid in water) and 2% mobile phase B (methanol) was used to elute the metabolites. A subject's acetylator phenotype was determined according to the following equation ("ratio 1"): (AFMU+AAMU)/(AFMU+AAMU+1×+1U). AFMU was not quantified. Instead it was converted before sample processing to AAMU. In general fast acetylators have a ratio of greater than about 0.2, in another example between about 0.2 to about 0.3, in another example greater than 0.3, in another example between about 0.3 and about 0.6; and slow acetylators have a ratio of about 0.2 or less, for example between about 0.1 and about 0.2 (inclusive). The subjects in the trial described in Example 18 were phenotyped using this method. Results are given in Table 5 below in Example 16.

Example 16

NAT2 Genotypic Determination

N-acetyltransferase 2 (NAT2) genotype for a subject can be identified in a number of ways to determine whether a subject is a fast or slow acetylator. The examples given herein and throughout the specification are exemplary and are not meant to be limiting. In particular, different populations of people may have different mutations which were not disclosed here, but are known to one of ordinary skill in the art. For example, a person's genotypic status can be determined using methods known in the art, for example Cascorbi et al, *Am. J. Hum. Genet.*, 57:581-592, 1995 which is incorporated herein by reference in its entirety.

Additionally, genotyping can be accomplished using the following method. For the trial in Example 18, a 10 mL sample of blood was collected from each subject in an K₂EDTA tube. Samples were stored at 4° C. for a maximum of five days. If stored for longer, they were stored at −20° C. Genomic DNA was isolated from EDTA-anticoagulated peripheral blood using standard methods. Genomic DNA was placed in a 96-well plate and transferred to a StepOne-Plus Real Time PCR system from Applied Biosystems (TaqMan SNP genotyping with allelic discrimination). The background fluorescence signal was determined before amplification. Using PCR, the DNA sequence concerned was labeled with the molecular probes C282T and T341C and was surrounded by primers. The NAT 2 genes were exponentially amplified and the fluorescent markers incorporated. The molecular probes C282T and T341C detect about 95% of all NAT2 mutations. For NAT2 T341C, the Wild Type allele is identified with the FAM™-labeled probe and the mutant with the VIC®-labeled probe. For NAT2 C282T, the Wild Type allele was identified with the VIC®-labeled probe and the mutant with the FAM™-labeled probe. A person with at least one fast alleles was categorized as a fast acetylator. A person with no fast alleles was categorized as a slow acetylator. A summary of possible NAT2 gene polymorphisms is outlined in the Table 4 below using two molecular probes: C282T and T341C. Genotyping and phenotyping results for each subject in Example 18 are given in Table 5.

TABLE 4

Possible NAT2 gene polymorphisms

| T341C | C282T | Assigned Phenotype Status |
|---|---|---|
| Wildtype | Wildtype | Rapid |
| Wildtype | Heterozygote | Intermediate |
| Wildtype | Mutant | Slow |
| Heterozygote | Wildtype | Intermediate |
| Heterozygote | Heterozygote | Slow or Intermediate depending on location (caffeine) |
| Heterozygote | Mutant | Slow |
| Mutant | Wildtype | Slow |
| Mutant | Heterozygote | Slow |
| Mutant | Mutant | Slow |

TABLE 5

Genotyping and phenotyping results per patient

| Subject | Gender | Ratio 1, Ex. 15a | Phenotype | T341C | C282T | Genotype |
|---|---|---|---|---|---|---|
| Part 1, Group 1 | | | | | | |
| 1 | M | 0.457 | fast | Wildtype | Heterozygote | fast |
| 2 | F | 0.428 | fast | Heterozygote | Wildtype | fast |
| 3 | M | 0.154 | slow | Heterozygote | Heterozygote | slow |
| 4 | M | 0.135 | slow | Wildtype | Homozygote mutant | slow |
| 5 | F | 0.409 | fast | Heterozygote | Wildtype | fast |
| 6 | M | 0.380 | fast | Wildtype | Heterozygote | fast |
| 7 | M | 0.182 | slow | Wildtype | Homozygote mutant | slow |
| 8 | M | 0.189 | slow | Homozygote mutant | Wildtype | slow |
| 9 | F | 0.378 | fast | Heterozygote | Wildtype | fast |
| 10 | M | 0.394 | fast | Wildtype | Heterozygote | fast |
| 11 | F | 0.194 | slow | Wildtype | Homozygote mutant | slow |
| 12 | F | 0.176 | slow | Homozygote mutant | Wildtype | slow |
| Part 2, Group 1 | | | | | | |
| 1 | M | 0.465 | fast | Wildtype | Heterozygote | fast |
| 2 | F | 0.433 | fast | Wildtype | Heterozygote | fast |
| 3 | M | 0.154 | slow | Heterozygote | Heterozygote | slow |
| 4 | M | 0.195 | slow | Heterozygote | Heterozygote | slow |
| Part 2, Group 2 | | | | | | |
| 1 | M | 0.150 | slow | Heterozygote | Heterozygote | slow |
| 2 | M | 0.146 | slow | Heterozygote | Heterozygote | slow |
| 3 | M | 0.152 | slow | Heterozygote | Heterozygote | slow |
| 4 | M | 0.195 | slow | Wildtype | Homozygote mutant | slow |
| 5 | M | 0.154 | slow | Wildtype | Homozygote mutant | slow |
| 6 | F | 0.456 | fast | Heterozygote | Wildtype | fast |
| 7 | F | 0.407 | fast | Wildtype | Wildtype | fast |
| 8 | M | 0.515 | fast | Wildtype | Wildtype | fast |
| 9 | M | 0.415 | fast | Wildtype | Heterozygote | fast |
| 10 | M | 0.393 | fast | Heterozygote | Wildtype | fast |

Other NAT2 gene mutations are induced by replacement of a wild type allele nucleotide sequence at positions 192, 282, 341, 434, 481, 590, 813, 845, and 857. These mutations cause impaired acetylation. In particular, 4 mutations— 191A, 481T, 590A, and 857A—account for nearly all slow acetylator alleles among blacks, whites, Asian Indians, Koreans, Japanese, Hong Kong Chinese, Taiwanese, Filipinos, and Samoans (Lin et. al. *Pharmacogenetics* 1994, 4(3), 125-134). A subject can be tested for these mutations in order to determine whether they are slow acetylators.

The NAT 1 gene can be examined for 7 single nucleotide polymorphisms (SNPs) in alleles *3, *10, *11, *14, *15, and *17.

Alternatively, a subject's genotype can be determined using methods described in *Br J Clin Pharmacol.* 2000, 49(3), 240-243 or *Archives of Toxicology* 2005, 79(4), 196-200. A person of ordinary skill in the art would know other methods that could be used to determine a person's NAT1 and NAT2 genotype.

Example 17a

LC/MS/MS Determination of 3,4-Diaminopyridine (3,4-DAP) in Human Plasma and Urine The following method was used to analyze concentrations of 3,4-diaminopyridine and N-(4-aminopyridin-3-yl)acetamide in plasma and urine samples for the experiments in Example 10. In the LC/MS/MS method, the human plasma and urine samples were extracted using acetonitrile containing 0.1% formic acid. Samples were analyzed by using normal-phase HPLC with Turbo-Ion Spray® MS/MS detection. The column was an Atlantis HILIC Silica column (3 μm, 2.1×100 mm) at a temperature of 45° C. Mobile phase A was acetonitrile/isopropanol (90/10; v/v) containing 0.1% formic acid. Mobile phase B was water containing ammonium formate (20 mM) and 0.1% formic acid. The flow rate was 800 μL/minute. The gradient conditions for human plasma and urine samples were as follows:

| Time (min) | A (%) | B (%) |
|---|---|---|
| 0.0 | 95 | 5 |
| 0.5 | 95 | 5 |
| 4.0 | 90 | 10 |
| 4.5 | 20 | 80 |
| 5.5 | 20 | 80 |
| 5.6 | 95 | 5 |
| 7.0 | 95 | 5 |

The LC/MS/MS method was validated to quantify 3,4-DAP in human plasma in the linear calibration range of 0.5 to 500 ng/mL and from 2 to 2000 ng/mL for the 3-N-acetyl metabolite. The validated method used for urine quantification ranged from 150 to 15000 ng/mL for amifampridine and the 3-N-acetyl metabolite.

Example 17b

LC/MS/MS Determination of 3,4-Diaminopyridine (3,4-DAP) in Human Plasma and Urine The following method was used to analyze concentrations of 3,4-diaminopyridine and N-(4-aminopyridin-3-yl)acetamide in plasma and urine samples for the experiments in Example 18. In the LC/MS/MS method, the human plasma and urine samples were extracted using acetonitrile containing 0.1% formic acid. Samples were analyzed by using HPLC with positive ion electrospray MS/MS detection. The column was an Atlantis HILIC Silica column (3 μm, 3×50 mm) at a temperature of 40° C. Mobile phase A was water containing ammonium formate (20 mM) and 0.1% formic acid. Mobile phase B was acetonitrile/isopropanol (90/10; v/v) containing 0.1% formic acid. The flow rate was 0.90 mL/minute. The gradient conditions for human plasma and urine samples were as follows:

| Time (min) | A (%) | B (%) |
|---|---|---|
| 0.00 | 10 | 90 |
| 0.50 | 10 | 90 |
| 2.00 | 30 | 70 |
| 2.80 | 90 | 10 |
| 3.60 | 90 | 10 |
| 3.70 | 10 | 90 |

The LC/MS/MS method was validated to quantify 3,4-DAP in human plasma in the linear calibration range of 0.500 to 500 ng/mL and from 1.00 to 1000 ng/mL for the 3-N-acetyl metabolite.

Example 18

Clinical Trial to Study the Safety of Firdapse on Slow and Fast Acetylators

Objectives

The primary objective of the study was to assess the safety and tolerability of 3,4-DAP phosphate after single and multiple doses. The secondary objectives of the study were Part 1 only: To determine the dose-related PK profile of amifampridine and of 3-N-acetyl amifampridine after single, escalating doses of 3,4-DAP phosphate Part 2 only: To assess the steady-state plasma PK and accumulation of amifampridine and of 3-N-acetyl amifampridine over multiple days of dosing with 3,4-DAP phosphate An exploratory objective was to examine the overall activity of the N-acetyl transferase enzymes on the metabolism of amifampridine by assessing the PK of amifampridine and 3-N-acetyl amifampridine with phenotypic acetylation activity and genotyping determination of NAT2 gene polymorphisms.

Study Design and Plan

This open-label study in healthy subjects (male and female) was conducted in 2 parts. A total of 26 healthy male and female subjects, 12 in Part 1 (at least 5 of each sex), 4 in Part 2 Group 1, and 10 in Part 2 Group 2 (at least 4 of each sex) were enrolled into the study. The same subjects were not enrolled to participate in both parts. Subjects in Part 2 were dosed only after all subjects of Part 1 completed dosing and at least 24-hours of follow-up safety evaluation after the last dose were completed.

All subjects were characterized for their metabolic acetylation phenotype and NAT2 genotype in order to divide subjects into two groups of acetylators. Volunteers were genetically typed for highly variant alleles of the N-acetyl transferase 2 enzyme (NAT2) domain on chromosome 8 (according to Example 16) and were phenotyped for acetylation rates with a caffeine challenge test (according to Example 15a). Approximately equal numbers of slow and fast acetylators (as defined by a caffeine challenge test in Example 15a) were enrolled in each group. In Part 2, very slow acetylators with NAT2 activity (ratio 1, Example 15a) below 0.06 were excluded from participation in the study. In each part of the study, subjects were assessed for PK, safety, and tolerability and all doses were administered within 30 min of ingestion of a meal or a snack.

Part 1

Part 1 was a dose-proportionality study in 12 healthy subjects each receiving 4 ascending single oral doses of 3,4-DAP phosphate in a sequential manner (5 mg, 10 mg, 20 mg, and 30 mg). For all 12 subjects, the first 3 doses of oral 3,4-DAP phosphate (5-20 mg) were administered on 3 consecutive days (Days 1-3). Two fast and two slow acetylators (as defined by a caffeine challenge test in Example 15a) were selected as the first 4 enrolled subjects (sentinel subjects). For the 2 fast acetylators the 30 mg dose was administered on Day 4. No seizures were seen within 24 hours of dosing and thus the remaining 2 slow acetylators were dosed on Day 5. No seizures were seen in the two slow acetylators dosed on Day 5. Safety and tolerability data collected for all 4 subjects were reviewed and the safety and tolerability results of the 30 mg dose for these 4 sentinel subjects were acceptable. The 30 mg dose was given to the remaining 8 non-sentinel subjects on Day 7. Sentinel and non-sentinel subjects were released from the clinic on Day 5, Day 6, and Day 8 respectively, with all subjects returning for follow-up assessments 2-4 days following their last dose. See Table 1.

TABLE 1

Part 1 Cohort

| Cohort | Number of Subjects Slow | Number of Subjects Fast | 3,4-DAP phosphate Dose (mg base equiv) | Firdapse ® Tablets administered | Comment |
|---|---|---|---|---|---|
| Part 1 | 6 | 6 | 5 | ½ | Dosed on Day 1 |
| Part 1 | 6 | 6 | 10 | 1 | Dosed on Day 2 |
| Part 1 | 6 | 6 | 20 | 2 | Dosed on Day 3 |
| Part 1 | 2 | 2 | 30 | 2½ | Sentinel Subjects, dosed on Day 4 |
| Part 1 | 4 | 4 | 30 | 2½ | Dosed on Day 7 |

Part 2

Part 2 consisted of 14 subjects, who did not participate in Part 1, separated into 2 groups, as follows:

Part 2, Group 1:

Four sentinel subjects were selected after determining their acetylator status. Two were fast acetylators and two were slow acetylators. All four were dosed on Day 1 with 4 oral doses of 20 mg of 3,4-DAP phosphate (given at 4-hour dosing intervals). See Table 2. On Days 1 and 2, safety and tolerability data was collected. Subjects left the clinic on Day 2. The safety and tolerability data collected for these 4 sentinel subjects were reviewed. The safety and tolerability results of Days 1 and 2 for these subjects were acceptable and thus Part 2 Group 2 was commenced. Minimally acceptable safety was defined as the absence of clinical seizure activity. Subjects in Group 1 returned to the clinic for their follow-up assessments 2-4 days following their last dose. No seizures occurred in Part 2 Group 1.

TABLE 2

| Cohort | Number of Subjects Slow | Number of Subjects Fast | 3,4-DAP phosphate Dose (mg base equiv) | Firdapse ® Tablets administered | Comment |
|---|---|---|---|---|---|
| Part 2, Group 1 | 2 | 2 | 20 | 2 | Sentinel Subjects: Day 1 QID Dosing only |
| Part 2, Group 2 | 5 | 5 | 20 | 2 | 3 Days QID Dosing with 4th day AM single dose |

Part 2, Group 2:

No seizures occurred in Part 2 Group 1 and 10 subjects were dosed on Days 1-3 with 4 oral doses of 20 mg 3,4-DAP phosphate per day (given at 4-hour dosing intervals). Each subject was given a final morning dose of 20 mg 3,4-DAP phosphate on Day 4. See Table 2. Subjects in Group 2 returned to the clinic for their follow-up assessments 2-4 days following their last dose.

Screening

The following assessments, procedures, and evaluations were performed as part of the screening process: medical history, clinical laboratory tests, vital signs, physical examination, 12-lead electrocardiogram (ECG), electroencephalogram (EEG), acetylation phenotyping (1 sample from urine pooled over a 6-hour period), NAT2 genotyping, drug screening, hepatitis B surface antigen (HBsAg) status, HCV status, anti-HIV 1 and 2 status, urine cotinine, and pregnancy (females of childbearing potential only). Drug screening, urine cotinine, pregnancy testing (females only), and clinical laboratory testing were repeated upon admission to the clinic (Assessment Phase).

Assessments

Assessment Periods are defined as follows.

Part 1: Assessments took place in clinic from 18 hours before study drug administration on Day 1 and up to 24 hours after last drug administration on Day 4 for sentinel fast acetylator subjects, on Day 5 for sentinel slow acetylator subjects, and from 18 hours before study drug administration on Day 1 and up to 24 hours after last drug administration on Day 7 for non-sentinel subjects.

Part 2 Group 1: Assessments took place in clinic from 18 hours before first study drug administration on Day 1 and up to 24 hours after first drug administration on Day 1.

Part 2 Group 2: Assessments took place in clinic from 18 hours before first study drug administration on Day 1 and up to 24 hours after drug administration on Day 4.

Urine Collection for Phenotyping:

For acetylation phenotyping, urine samples were collected for 6 hours after a single oral dose of caffeine on Day −7. A single sample from the pooled volume was analyzed. See Example 15a.

Blood Sampling for NAT2 Genotyping and PK:

For all subjects, a blood sample for NAT2 genotyping was collected on Day −1. Additional blood sampling was conducted during the assessment period for Part 1 and Part 2 of the study, as follows:

Part 1 (single daily dosing): To determine the PK of amifampridine and 3-N-acetyl amifampridine in plasma following single daily doses of 5, 10, 20 and 30 mg, blood samples were taken pre-dose (between waking up and dosing) and at 10, 20, 30, 45, 60, 75 min, and 1.5, 2, 4, 6, 8, 10, 12, 16 and 24 hours post-dose after each single daily dose [pre-dose draws on Days 2-3 (all subjects) and Day 4 (sentinel fast acetylator subjects only) are the same draws as the 24-hour draw from the previous dose].

Part 2 Group 1 (all sentinel subjects): To determine the PK of amifampridine and 3-N-acetyl amifampridine at 20 mg QID (4 times a day) for one day, blood samples were taken on Day 1 as follows:

Doses 1 and 3: pre-dose and 10, 20, 30, 45, 60, 75 min, and 1.5, 2, 3, and 4 hours post-dose Doses 2 and 4: 0.5, 1, 1.5, 2, and 4 hours post-dose)

Dose 3 was administered following a snack and doses 1, 2, and 4 were administered following a meal.

Part 2 Group 2 (multiple daily dosing): For PK of amifampridine and 3-N-acetyl amifampridine in plasma following 20 mg QID (4 times a day) oral dosing, blood samples were taken, as follows:

Day 1 and Day 3, Doses 1 and 3 on each day: pre-dose and 10, 20, 30, 45, 60, 75 min, and 1.5, 2, 3, and 4 hours post-dose; Doses 2 and 4: 0.5, 1, 1.5, 2, and 4 hours post-dose. Dose 3 was administered following a snack; doses 1, 2, and 4 were administered following a meal.

Day 2: Trough sample collected in the morning (pre-Dose 1) and evening (pre-Dose 3)

Day 4: pre-dose and 10, 20, 30, 45, 60, 75 min, and 1.5, 2, 4, 6, 8, 10, 12, 16, and 24 hours post-dose.

For PK sampling 2 mL of blood was collected into the appropriate Lithium heparin polyethylene teraphthalate collection tubes. Tubes were gently inverted approximately 5 times to afford mixing before processing. After drawing and inverting, the blood sample was immediately transferred to an ice water bath. The samples were processed within 30 min by centrifugation for 10 min at 4° C. and 1500×g. The plasma was transferred into 3 separate 2 mL polypropylene tubes (2 primary samples and 1 back-up sample) which were immediately capped. The PK plasma samples were immediately frozen and stored at −20° C. until analysis.

Plasma concentrations of 3,4-DAP and 3-N-Acetyl 3,4-DAP metabolite were measured using a validated liquid chromatography and tandem mass spectrometric detection (LC-MS/MS) method (Example 17b) employing an individual stable isotope labeled internal standard for each analyte 3,4-DAP and 3-N-acetyl 3,4-DAP metabolite.

Safety Assessments:

During the assessment period, the following safety measures were evaluated: vital signs, adverse events (AEs), 12-lead ECG, EEG and clinical laboratory tests.

Follow-Up:

Upon completion of the assessment period, the following procedures and evaluations were performed: adverse events, previous concomitant medications, clinical laboratory tests, pregnancy status (females of childbearing potential only), vital signs, physical examination, and 12-lead ECG and EEG.

Diagnosis and all Criteria for Inclusion and Exclusion:

Individuals eligible to participate in this study had the ability and willingness to abstain from alcohol, methylxanthine-containing beverages or food (e.g., coffee, tea, cola, chocolate, "power drinks"), poppy seed and grapefruit (juice) 48 hours prior to admission and during clinic stays.

Individuals who met any of the following exclusion criteria were not eligible to participate in the study: subjects with, or with a recent history of, any clinically significant neurological, gastrointestinal, renal, hepatic, cardiovascular, psychiatric, respiratory, metabolic, endocrine, hematological or other major disorders; subjects with a prior history of seizures; and for Part 2 only: subjects with an NAT2 activity (ratio 1, Example 15a) below 0.06.

Investigational Product, Dose, Route and Regimen

IP was provided as scored tablets containing the equivalent of 10 mg amifampridine free base, which was administered orally. Doses per subject are as described below based on the content of active amifampridine ingredient. All doses were given within 30 min following ingestion of a standard meal or snack.

Part 1 Single-Dose Study (12 Subjects):

Each of 12 subjects received 4 ascending single doses of 3,4-DAP phosphate in a sequential manner (5 mg, 10 mg, 20 mg, and 30 mg). All 12 subjects were administered the first 3 doses (i.e., 5-20 mg) on 3 consecutive days (Days 1-3). Two fast and 2 slow acetylators were selected as the first 4 enrolled subjects. For the 2 fast acetylators, the 30 mg dose was administered on Day 4. No seizures were seen within 24 hours of dosing, and the remaining 2 slow acetylators were dosed on Day 5. No seizures were seen in the two acetylators dosed on Day 5. Safety and tolerability data collected for these 4 subjects were reviewed. The safety and tolerability results of the 30 mg dose for these 4 sentinel subjects were acceptable, and the 30 mg dose was given to the remaining 8 non-sentinel subjects on Day 7. Sentinel and non-sentinel subjects were released from the clinic on Day 5, Day 6, and Day 8 respectively, with all subjects returning for follow-up assessments 2-4 days following their last dose.

Part 2 Group 1 (4 Subjects):

Four subjects received 4 single doses of 20 mg 3,4-DAP phosphate given 4 hours apart on 1 day only.

Part 2 Group 2 (10 Subjects):

No seizures occurred in Part 2 Group 1, and 10 subjects received drug as follows: on days 1-3, 4 single doses per day of 20 mg 3,4-DAP phosphate given 4 hours apart and on day 4, 1 dose at 20 mg 3,4-DAP phosphate.

Duration of Treatment

Subjects in Part 1 were dosed for 4 days. Subjects in Part 1 were administered 4 single ascending doses of 3,4-DAP phosphate (5 mg, 10 mg, 20 mg, and 30 mg). For the 2 sentinel fast acetylator subjects, dosing was completed on Days 1-4; for the 2 sentinel slow acetylator subjects, dosing was completed on Days 1-3 and on Day 5; for 8 non-sentinel subjects, dosing was completed on Days 1-3 and on Day 7.

Part 2 subjects were dosed for 1 or 4 days. Part 2 Group 1 subjects were administered 4 doses of 20 mg 3,4-DAP phosphate on Day 1 only. Part 2 Group 2 subjects were administered 4 doses of 20 mg 3,4-DAP phosphate on each of Days 1-3 and a single terminal morning dose on Day 4.

Criteria for Evaluation

Pharmacokinetics:

Plasma concentrations of amifampridine and its 3-N-acetyl metabolite were evaluated. The PK parameters calculated were $C_{max}$, $t_{max}$, $k_{el}$, $t_{1/2}$, $AUC_{0-\tau}$, $AUC_{0-t}$, $AUC_{0-inf}$, % $AUC_{0-inf}$, CL/F, Vz/F, $R_{ac}$, where $C_{max}$, $t_{max}$, $t_{1/2}$, CL/F, and Vz/F are defined in the Abbreviations table and the others are defined as follows:

$k_{el}$=elimination rate constant $AUC_{0-last}$=area under the plasma concentration-time curve up to time t, where t is the last time point with concentrations above the lower limit of quantitation $AUC_{0-inf}$=total AUC after extrapolation from time t to time infinity, where t is the last time point with a concentration above the lower limit of quantitation $AUC_{0-inf}=AUC_{0-last}+Ct/k_{el}$, where Ct is the last measurable plasma concentration % AUC=percentage of estimated part for the calculation of $AUC_{0-inf}$: $((AUC_{0-inf}-AUC_{0-t})/AUC_{0-inf})*100\%$ $AUC_{0-\tau}$=area under the plasma concentration time curve over a dosing interval τ

$R_{ac}$=accumulation ratio, based on $AUC_{0-\tau}$ of Day 4 versus Day 1

For exploratory purposes, the PK of amifampridine and 3-N-acetyl amifampridine were assessed with urine caffeine acetylation activity and NAT2 enzyme allelic genotyping results.

Safety:

Safety was assessed by the incidence of AEs, as well as changes in vital signs, 12-lead ECG, EEG, and clinical laboratory evaluations.

Efficacy:

No efficacy analyses were performed for this study.

Statistical Methods

Pharmacokinetics:

All subjects who were administered at least 1 dose of study drug during each part of the study were included in the PK evaluation of that part. Dose proportionality analysis and descriptive statistics were performed using available PK data collected during Part 1; descriptive statistics were performed using available PK data collected during Part 2.

Safety:

All subjects who received any amount of study drug in either Part 1 or Part 2 of this study and had post-dose safety information were included in the safety analyses. Safety was evaluated separately for Part 1 and Part 2 and was summarized by dose levels where appropriate. All verbatim AE terms were coded using Medical Dictionary for Regulatory Activities (MedDRA) terminology. Only treatment-emergent AEs (i.e., AEs with a start date on or after the first dose of study drug) were summarized. The incidence of AEs and SAEs were summarized for each study part by dose level, system, organ, class, preferred term, relationship to study drug, and severity. No deaths during the study, no discontinuations of study drug, and no withdrawals from the study and study drug due to an AE were observed.

Pharmacokinetics Results

Part 1

Figure 22:
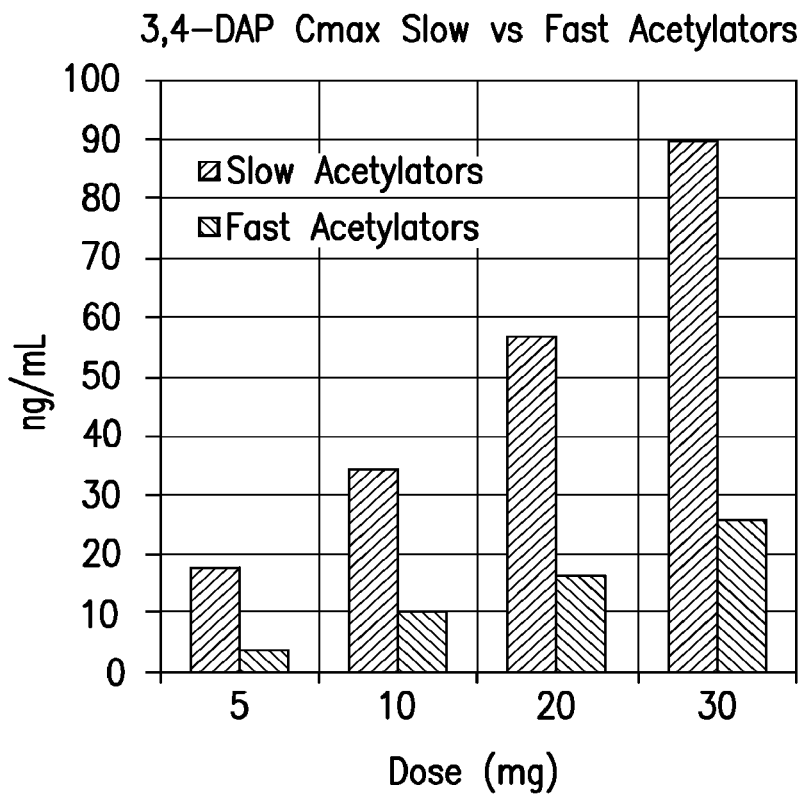
FIG. 22 depicts 3,4-DAP $C_{max}$ for slow and fast acetylators for the Trial Described in Example 18, Part 1.
Figure 23:
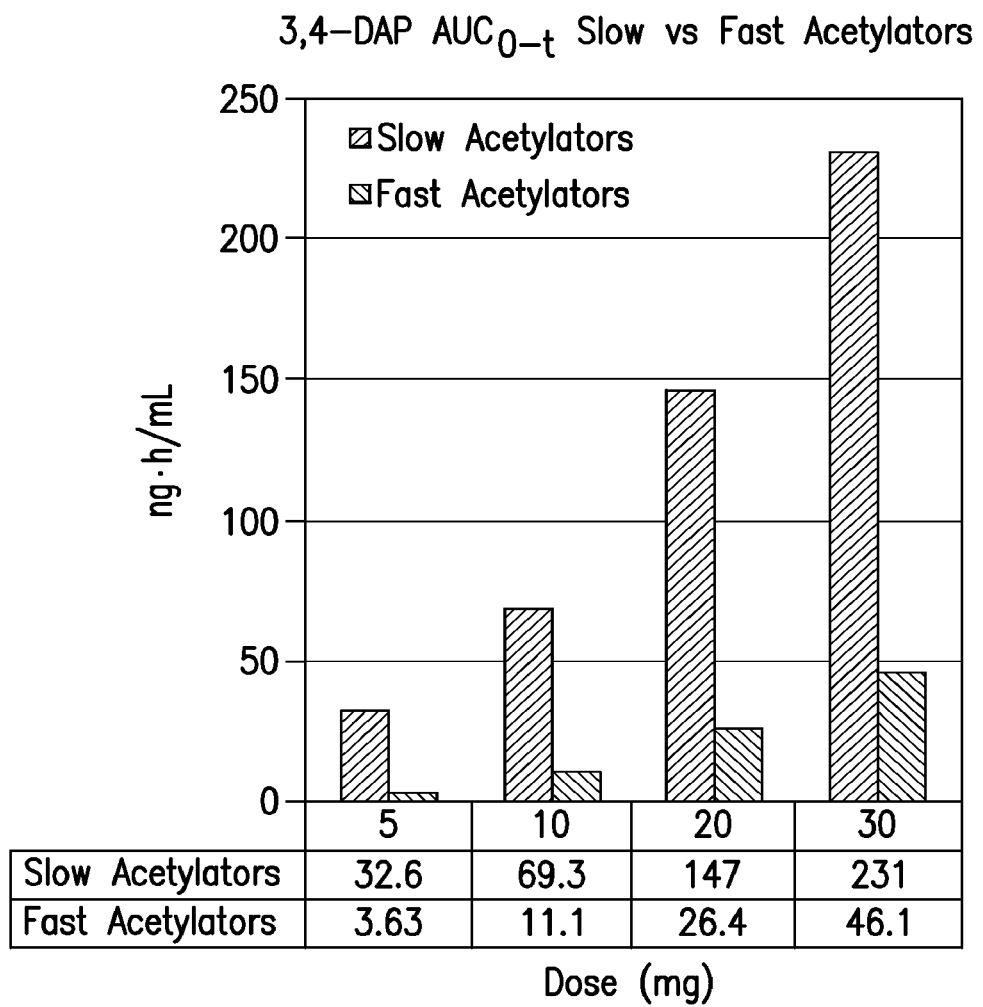
FIG. 23 depicts 3,4-DAP $AUC_{0-t}$ for slow and fast acetylators for the trial described in Example 18, Part 1.

FIG. 24a gives a summary of the mean pharmacokinetic parameters of 3,4-DAP in slow and fast acetylator phentoypes and FIG. 24b summarizes data for the metabolite. After single oral doses of Firdapse® ranging from 5 to 30 mg, a mean $C_{max}$ of 3.98-25.5 ng/mL was reached at 0.75-1.04 hours post-dose in the fast acetylator phenotype and a mean $C_{max}$ of 17.9-89.6 ng/mL was reached in 0.83-1.29 hours post-dose in slow acetylator phenotypes. Across each of the single dose groups, the ratio of mean $C_{max}$ slow acetylators to $C_{max}$ fast acetylators ranged from 3.5 to 4.5 fold (FIG. 22 and FIG. 24a). Mean plasma concentration-time profiles of 3,4-DAP phosphate for single-dose cohorts in the fast and slow acetylator groups are presented in FIG. 25. Mean terminal elimination half-lives were between 0.603 and 1.65 hours in fast acetylators and between 2.22 and 3.11 hours in slow acetylator phenotypes (FIG. 24a). The $C_{max}$ values increased essentially in a dose proportional manner with respect to a 6-fold dose range (5 to 30 mg) in both the slow (5.01 fold increase) and fast (6.41 fold increase) acetylator groups (FIG. 24a). The AUC values increased in a greater than dose proportional manner with respect to a 6-fold dose range (5 to 30 mg) in both the slow (7.64 fold increase) and fast (15.1 fold increase) acetylator groups (FIG. 23 and FIG. 24a). There were statistically significant differences (Students t-test: P≤0.01) in exposure and elimination PK parameters $C_{max}$, AUC, CL/F (observed clearance) and elimination t ½ between the fast and slow acetylator groups at all dose levels (FIG. 24a).

Differences in PK parameters between the two phenotypes is summarized by ratios of $C_{max}$ AUC, t ½ and observed clearance (CL/F) for 3,4-DAP phosphate in Table 3. Over the 5-30 mg single doses the BMN125 ratios of slow/fast ranged 3.5 to 4.50 fold for $C_{max}$, 5.29 to 10.4 fold for AUC, 1.88 to 3.68 for t ½, and 0.114 to 0.196 for observed clearance. Similarly for the metabolite the ratios of slow/fast ranged 0.498 to 0.540 for $C_{max}$, 0.661 to 0.717 for AUC, 1.13 to 1.22 for t ½ and 1.41 to 1.51 for observed clearance (FIG. 24b).

TABLE 3

For Cohort 1, Mean Ratios for 3,4-DAP phosphate Single Dose PK Parameters for Slow vs. Fast Acetylator Phenotypes: $C_{max}$, AUC, Elimination T½ and Clearance

| Ratio | Dose Level (mg) | Mean $C_{max}$ Slow/fast Ratio[a] | Mean $AUC_{0-t}$ Slow/fast Ratio[a] | Mean $t_{1/2}$ Slow/fast Ratio[a] | Mean CL/F Slow/fast Ratio[a] |
|---|---|---|---|---|---|
| 3,4-DAP | 5 | 4.50 | 10.4 | 3.68 | 0.114 |
|  | 10 | 3.47 | 6.94 | 2.15 | 0.163 |
|  | 20 | 3.50 | 5.75 | 2.38 | 0.186 |
|  | 30 | 3.51 | 5.29 | 1.88 | 0.196 |

[a]FIGS. are ratios of mean parameter values of Slow/Fast acetylator phenotypes 3,4-DAP data for Part 1 is summarized in Table 7 (day 1 of multiple dosing, fast and slow), Table 8 (day 3 of multiple dosing, fast and slow), Table 9 (day 4 of multiple dosing, fast and slow), and for the metabolite in Table 10 (day 1 of multiple dosing, fast and slow), Table 11 (day 3 of multiple dosing, fast and slow), and Table 12 (day 4 of multiple dosing, fast and slow). In Part 1 of the study there were statistically significant differences in PK parameters for exposure and elimination between the fast and slow acetylator groups at all dose levels indicate that metabolic clearance of Firdapse® by N-acetylation significantly impacts the plasma pharmacokinetic profile of oral Firdapse®.

Part 2

Figure 26A:
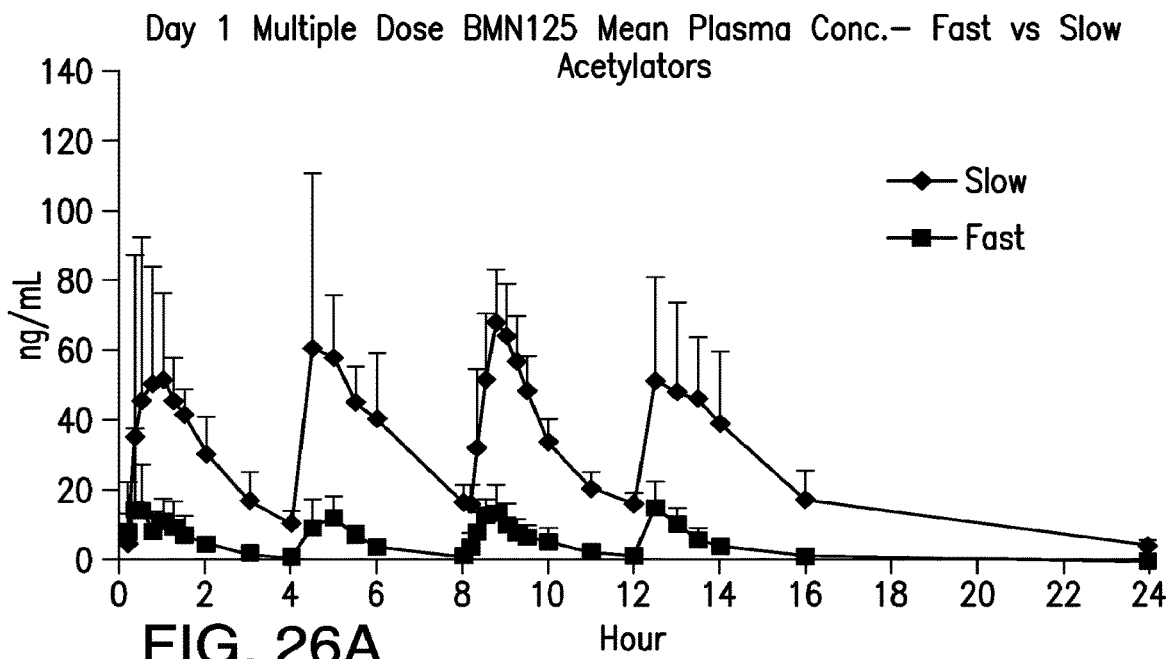
FIG. 26 depicts mean plasma concentrations of 3,4-DAP in slow and fast acetylators, QID Dosing of Firdapse® (20 mg base equiv), Day 1, 3, and 4 for the trial described in Example 18, Part 2.
Figure 26B:
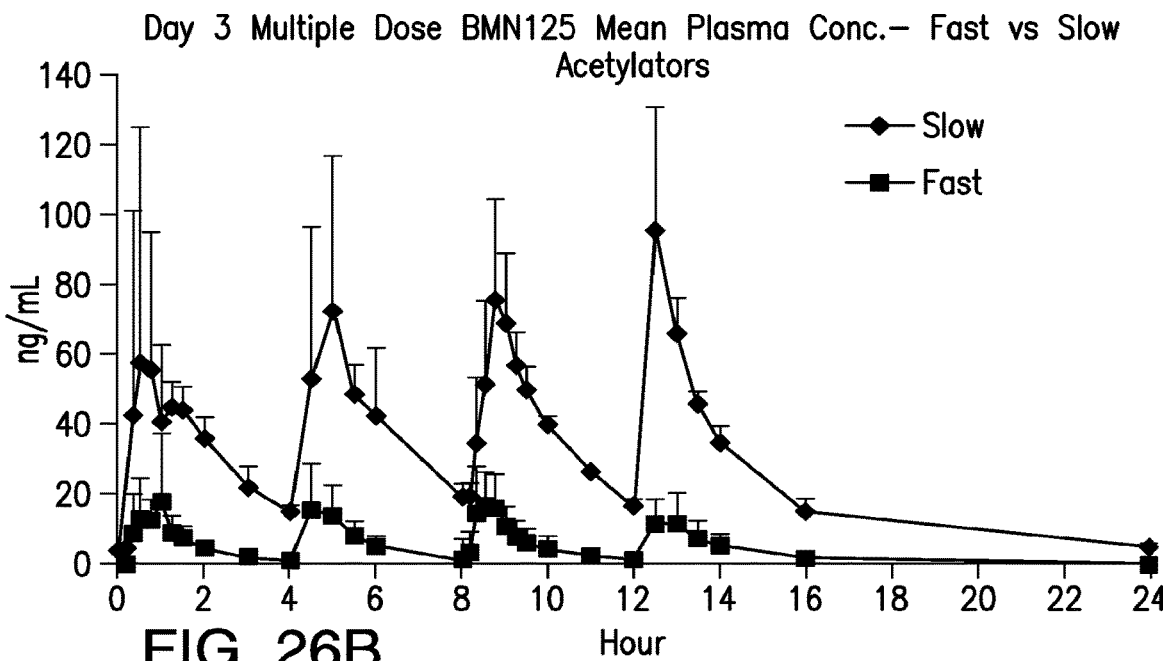
Figure 26C:
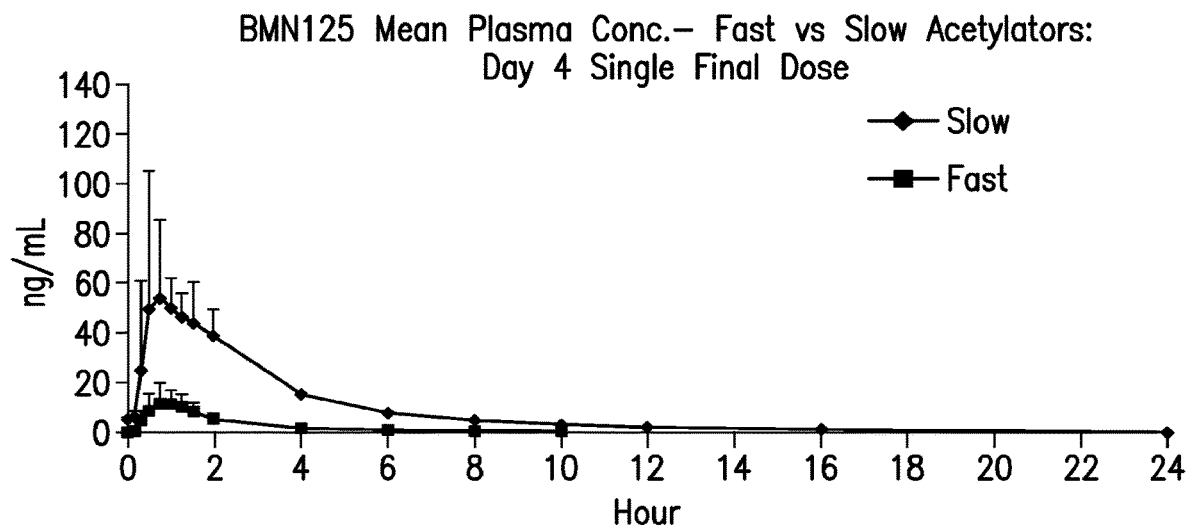

Mean plasma concentration-time profiles of for multiple-dose cohorts in the fast and slow acetylator groups are presented graphically in FIG. 26 (dosing days 1, 3 and 4). Mean plasma concentration-time plots of 3-N-acetyl metabolite for multiple-dose cohorts in the fast and slow acetylator groups are presented graphically in FIG. 27 (days 1, 3 and 4).

Figure 27A:
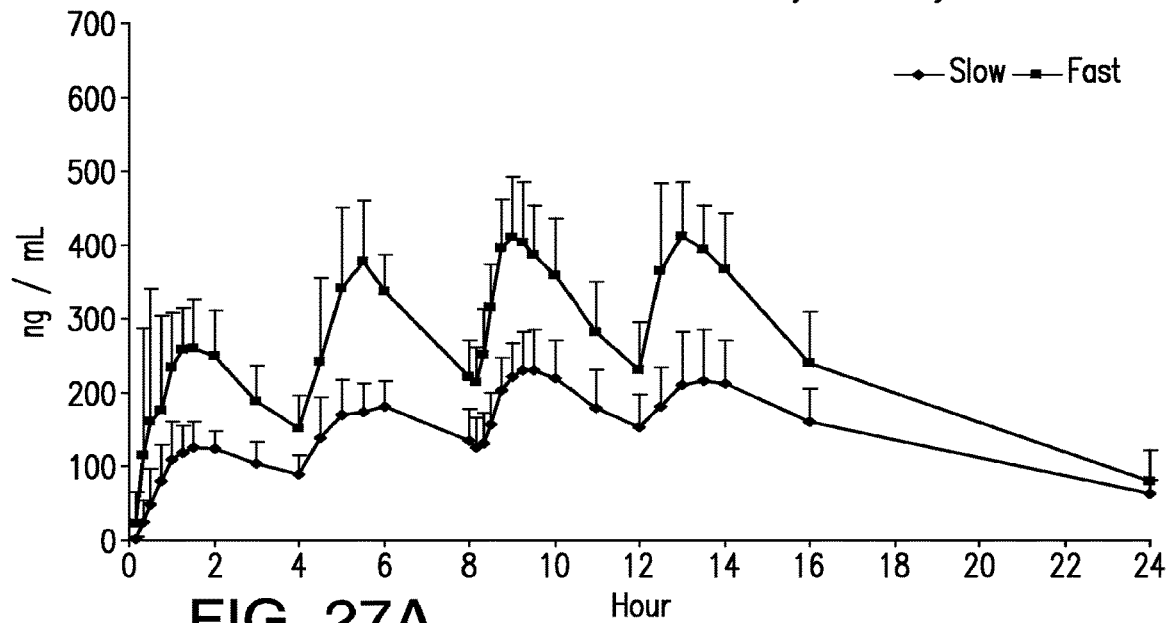
FIG. 27 depicts mean plasma concentrations of N-(4-aminopyridin-3-yl)acetamide in slow and fast acetylators, QID dosing of Firdapse® (20 mg base equiv) on Day 1, 3, and 4 for the trial described in Example 18, Part 2.
Figure 27B:
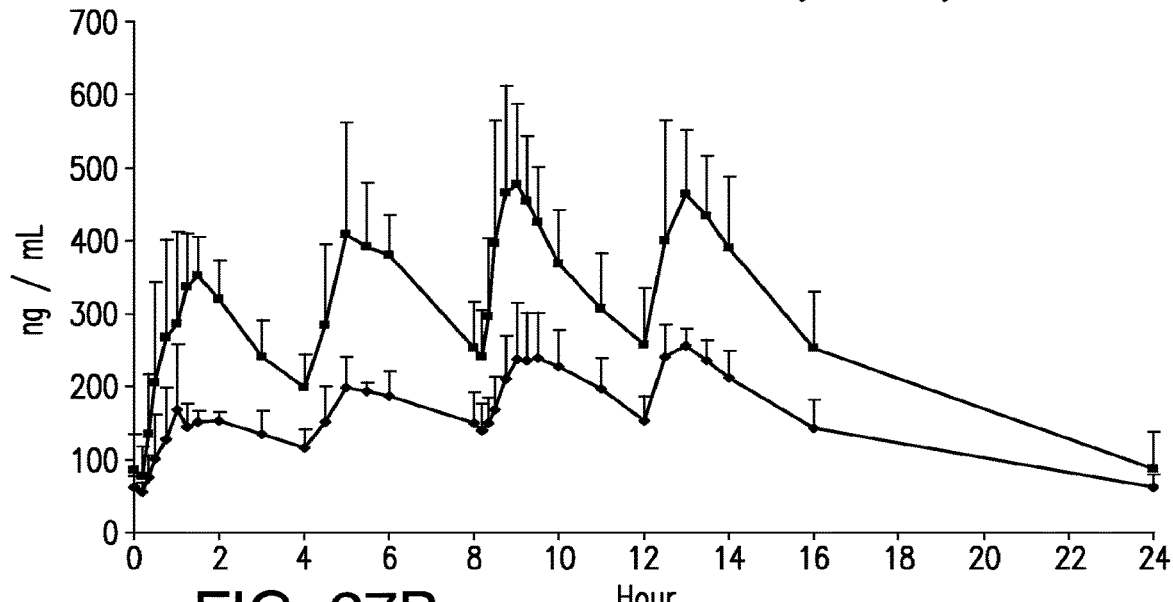
Figure 27C:
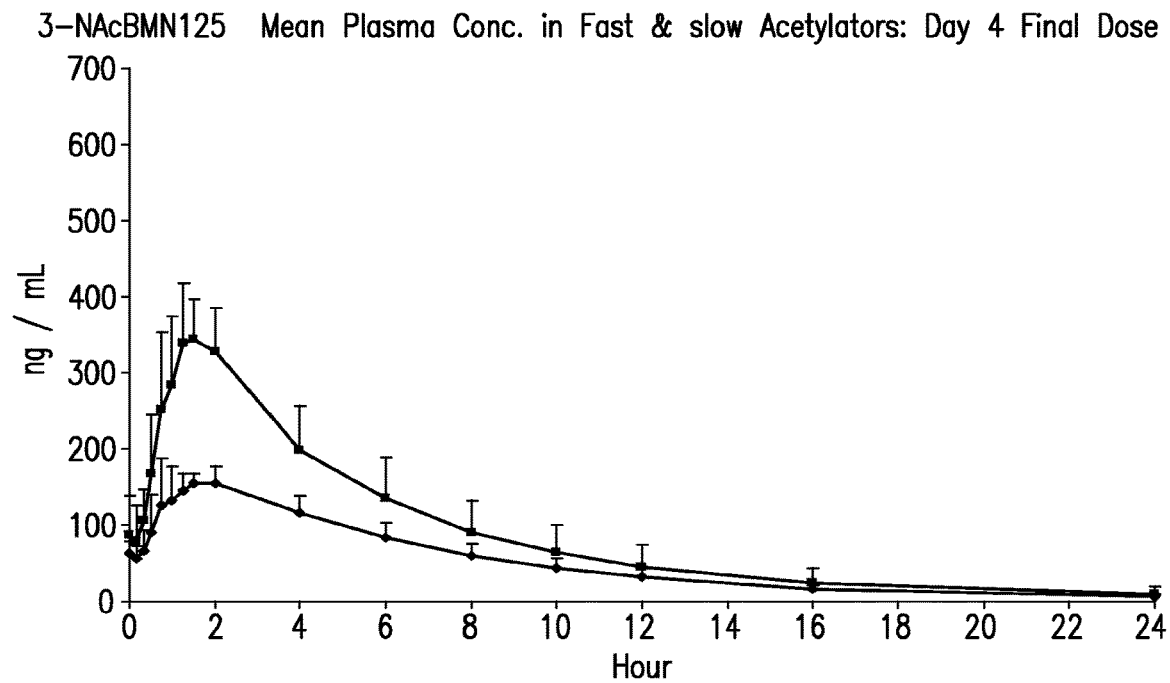

In the multiple-dose part 2 study (20 mg Firdapse®, QID, Q4 hr), Firdapse® plasma concentrations increased and declined within each of the dosing intervals evaluated on PK sampling days 1, 3 and 4 indicating rapid absorption, distribution and plasma clearance of Firdapse with fast acetylator phenotypes consistently having the lowest 3,4-DAP plasma concentrations (FIG. 26) and the highest metabolite plasma concentrations (FIG. 27). On Days 1-4 of Firdapse® dosing, 3,4-DAP plasma mean $C_{max}$ values ranged from 13.3-24.4 ng/mL in fast acetylators and from 67.1-97.1 ng/mL in slow acetylators (Table 7, 8, and 9). Firdapse® exposure measured by AUC indicated a range of dose interval $AUC_{0-4\ h}$ values of 22.5-28.5 ng-h/mL in fast acetylators and 115-168 ng-h/mL in slow acetylators on Days 1-4 of dosing (Table 7, 8, and 9). The terminal elimination half life for Firdapse® on dose day 4, after 3 days of subsequent QID dosing, was calculated to be 1.95 h in fast and 3.24 h in the slow acetylator group (Table 7, 8, and 9). Apparent volume of distribution (Vdz) and observed clearance (CL/F) were categorized as high (Vz>350 L, CL/F>85 L/h; 70 kg human) in both phenotypes for Firdapse® (Table 7, 8, and 9). Corresponding data is given for N-(4-aminopyridin-3-yl)acetamide in Tables 10, 11, and 12.

TABLE 7

Mean PK Parameter Summary for 3,4-DAP for Fast and Slow Acetylators on Day 1 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Mean PK Parameters Day 1 for Fast Acetylators (Phenotype) | | | | | | | | |
| Dose 1 | Arith. Mean | 23.5 | | 24.4 | 0.809 | 1.12 | 1334 | 898 |
| | SD | 9.34 | | 17.6 | 0.412 | 0.272 | 386 | 421 |
| | CV (%) | 39.7 | | 72.2 | 50.9 | 24.4 | 28.9 | 46.9 |
| Dose 2 | Arith. Mean | 22.5 | | 13.3 | 1.07 | 1.31 | 1336 | 757 |
| | SD | 9.81 | | 7.58 | 0.450 | 0.419 | 210 | 225 |
| | CV (%) | 43.6 | | 57.2 | 42.0 | 32.0 | 15.7 | 29.7 |
| Dose 3 | Arith. Mean | 24.1 | | 16.8 | 0.583 | 1.30 | 1725 | 879 |
| | SD | 11.1 | | 6.59 | 0.168 | 0.250 | 1132 | 466 |
| | CV (%) | 45.9 | | 39.3 | 28.7 | 19.2 | 65.6 | 53.0 |
| Dose 4 | Arith. Mean | 23.7 | | 16.4 | 0.643 | 1.49 | 1732 | 885 |
| | SD | 8.61 | | 5.76 | 0.244 | 0.590 | 847 | 531 |
| | CV (%) | 36.4 | | 35.1 | 38.0 | 39.7 | 48.9 | 60.0 |
| Dose 1-4 | Arith. Mean | | 97.9 | | | | | |
| | SD | | 39.7 | | | | | |
| | CV (%) | | 40.6 | | | | | |
| Mean PK Parameters Day 1 for Slow Acetylators (Phenotype) | | | | | | | | |
| Dose 1 | Arith. Mean | 115 | | 74.8 | 1.12 | 1.39 | 299 | 152 |
| | SD | 22.4 | | 36.8 | 0.536 | 0.257 | 48.4 | 29.7 |
| | CV (%) | 19.6 | | 49.1 | 47.9 | 18.5 | 16.2 | 19.5 |
| Dose 2 | Arith. Mean | 152 | | 83.7 | 1.14 | 1.93 | 293 | 107 |
| | SD | 17.9 | | 35.1 | 0.690 | 0.443 | 60.1 | 17.3 |
| | CV (%) | 11.8 | | 42.0 | 60.4 | 22.9 | 20.5 | 16.3 |
| Dose 3 | Arith. Mean | 140 | | 72.2 | 0.857 | 1.59 | 269 | 117 |
| | SD | 25.9 | | 17.3 | 0.197 | 0.168 | 52.5 | 29.3 |
| | CV (%) | 18.5 | | 24.0 | 22.9 | 10.6 | 19.5 | 25.1 |
| Dose 4 | Arith. Mean | 145 | | 67.1 | 1.29 | 2.52 | 338 | 101 |
| | SD | 35.6 | | 20.9 | 1.32 | 0.935 | 73.7 | 35.3 |
| | CV (%) | 24.6 | | 31.1 | 103 | 37.1 | 21.8 | 34.9 |
| Dose 1-4 | Arith. Mean | | 630 | | | | | |
| | SD | | 112 | | | | | |
| | CV (%) | | 17.8 | | | | | |

TABLE 8

PK Parameter Summary for 3,4-DAP for Fast and Slow Acetylators on Day 3 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Mean PK Parameters Day 3 for Fast Acetylators (Phenotype) | | | | | | | | |
| Dose 1 | Arith. Mean | 24.9 | | 24.0 | 0.800 | 1.07 | 1387 | 973 |
| | SD | 12.2 | | 18.1 | 0.274 | 0.209 | 753 | 695 |
| | CV (%) | 49.1 | | 75.6 | 34.2 | 19.6 | 54.3 | 71.5 |
| Dose 2 | Arith. Mean | 28.5 | | 18.7 | 0.900 | 1.34 | 1112 | 607 |
| | SD | 17.3 | | 10.9 | 0.652 | 0.258 | 310 | 248 |
| | CV (%) | 60.9 | | 58.5 | 72.4 | 19.2 | 27.8 | 40.8 |
| Dose 3 | Arith. Mean | 25.8 | | 21.9 | 0.532 | 1.73 | 2200 | 817 |
| | SD | 13.8 | | 12.4 | 0.211 | 0.573 | 1753 | 404 |
| | CV (%) | 53.5 | | 56.6 | 39.6 | 33.1 | 79.7 | 49.4 |
| Dose 4 | Arith. Mean | 25.1 | | 16.2 | 0.800 | 1.82 | 1867 | 795 |
| | SD | 13.2 | | 5.61 | 0.274 | 0.638 | 701 | 413 |
| | CV (%) | 52.7 | | 34.6 | 34.2 | 35.1 | 37.5 | 51.9 |

TABLE 8-continued

PK Parameter Summary for 3,4-DAP for Fast and Slow Acetylators on Day 3 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Dose 1-4 | Arith. Mean | | 111 | | | | | |
| | SD | | 62.1 | | | | | |
| | CV (%) | | 55.9 | | | | | |
| Mean PK Parameters Day 3 for Slow Acetylators (Phenotype) | | | | | | | | |
| Dose 1 | Arith. Mean | 130 | | 81.2 | 1.00 | 1.60 | 283 | 124 |
| | SD | 28.8 | | 51.9 | 0.395 | 0.239 | 47.9 | 19.3 |
| | CV (%) | 22.3 | | 64.0 | 39.5 | 14.9 | 16.9 | 15.6 |
| Dose 2 | Arith. Mean | 164 | | 96.1 | 1.00 | 1.97 | 260 | 92.9 |
| | SD | 17.7 | | 35.0 | 0.612 | 0.696 | 82.6 | 8.19 |
| | CV (%) | 10.8 | | 36.4 | 61.2 | 35.4 | 31.8 | 8.81 |
| Dose 3 | Arith. Mean | 156 | | 80.9 | 0.800 | 1.63 | 241 | 103 |
| | SD | 21.7 | | 20.4 | 0.274 | 0.177 | 34.0 | 12.5 |
| | CV (%) | 13.9 | | 25.2 | 34.2 | 10.9 | 14.1 | 12.1 |
| Dose 4 | Arith. Mean | 168 | | 97.1 | 0.600 | 3.56 | 376 | 73.2 |
| | SD | 21.6 | | 34.2 | 0.224 | 0.492 | 75.7 | 10.0 |
| | CV (%) | 12.9 | | 35.3 | 37.3 | 13.8 | 20.1 | 13.7 |
| Dose 1-4 | Arith. Mean | | 701 | | | | | |
| | SD | | 74.3 | | | | | |
| | CV (%) | | 10.6 | | | | | |

TABLE 9

Mean PK Parameter Summary for 3,4-DAP for Fast and Slow Acetylators (Phenotype) on Day 4 of Multiple Dosing (20 mg, Single Dose)
Mean PK Parameters Day 4, Single Dose

| | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Fast | Arith. Mean | 22.6 | 25.9 | 13.6 | 0.900 | 1.95 | 1774 | 673 |
| | SD | 10.0 | 12.9 | 6.60 | 0.454 | 0.723 | 388 | 195 |
| | CV (%) | 44.1 | 49.9 | 48.4 | 50.5 | 37.0 | 21.9 | 29.0 |
| Slow | Arith. Mean | 133 | 186 | 72.5 | 1.20 | 3.24 | 486 | 108 |
| | SD | 21.9 | 32.5 | 43.9 | 0.597 | 1.03 | 91.3 | 17.6 |
| | CV (%) | 16.5 | 17.5 | 60.6 | 49.7 | 31.9 | 18.8 | 16.3 |

TABLE 10

Mean PK Parameter Summary for 3-N-Acetyl Metabolite in Fast and Slow Acetylators on Day 1 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Mean PK Parameters Day 1 for Fast Acetylators (Phenotype) | | | | | | | | |
| Dose 1 | Arith. Mean | 773 | | 333 | 1.43 | 2.35 | 55.2 | 16.2 |
| | SD | 111 | | 79.7 | 0.875 | 0.191 | 11.6 | 2.32 |
| | CV(%) | 14.3 | | 23.9 | 61.2 | 8.15 | 21.0 | 14.3 |
| Dose 2 | Arith. Mean | 1160 | | 396 | 1.50 | 2.93 | 32.9 | 7.78 |
| | SD | 236 | | 92.6 | 0.289 | NC | NC | NC |
| | CV (%) | 20.4 | | 23.4 | 19.2 | NC | NC | NC |
| Dose 3 | Arith. Mean | 1277 | | 426 | 0.964 | 3.28 | 40.3 | 8.90 |
| | SD | 253 | | 76.9 | 0.336 | 0.818 | 7.10 | 2.23 |
| | CV (%) | 19.8 | | 18.0 | 34.9 | 24.9 | 17.6 | 25.0 |

TABLE 10-continued

Mean PK Parameter Summary for 3-N-Acetyl Metabolite in Fast and Slow Acetylators on Day 1 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Dose 4 | Arith. Mean | 1341 | | 433 | 1.14 | 3.93 | 40.0 | 7.62 |
| | SD | 272 | | 73.4 | 0.378 | 1.08 | 4.64 | 2.53 |
| | CV (%) | 20.3 | | 16.9 | 33.1 | 27.5 | 11.6 | 33.2 |
| Dose 1-4 | Arith. Mean | | 5744 | | | | | |
| | SD | | 1221 | | | | | |
| | CV (%) | | 21.3 | | | | | |
| | | Mean PK Parameters Day 1 for Slow Acetylators (Phenotype) | | | | | | |
| Dose 1 | Arith. Mean | 383 | | 150 | 1.68 | 2.95 | 120 | 28.8 |
| | SD | 62.4 | | 21.5 | 0.657 | 0.405 | 14.5 | 6.34 |
| | CV (%) | 16.3 | | 14.3 | 39.1 | 13.8 | 12.1 | 22.0 |
| Dose 2 | Arith. Mean | 627 | | 204 | 1.46 | 3.50 | 101 | 20.2 |
| | SD | 118 | | 22.6 | 0.588 | 0.657 | 3.17 | 3.17 |
| | CV (%) | 18.9 | | 11.1 | 40.4 | 18.8 | 3.15 | 15.7 |
| Dose 3 | Arith. Mean | 759 | | 240 | 1.25 | 4.00 | 71.5 | 13.5 |
| | SD | 185 | | 53.7 | 0.289 | 1.19 | 14.3 | 5.58 |
| | CV (%) | 24.4 | | 22.3 | 23.1 | 29.9 | 20.0 | 41.3 |
| Dose 4 | Arith. Mean | 769 | | 235 | 1.71 | 4.74 | 70.6 | 10.4 |
| | SD | 200 | | 61.8 | 1.07 | 1.04 | 16.1 | 1.57 |
| | CV (%) | 26.0 | | 26.3 | 62.7 | 22.0 | 22.8 | 15.1 |
| Dose 1-4 | Arith. Mean | | 3576 | | | | | |
| | SD | | 623 | | | | | |
| | CV (%) | | 17.4 | | | | | |

TABLE 11

Mean PK Parameter Summary for 3-N-Acetyl Metabolite in Fast and Slow Acetylators on Day 3 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| | | Mean PK Parameters Day 3 Phenotype: Fast Acetylators | | | | | | |
| Dose 1 | Arith. Mean | 1019 | | 374 | 1.35 | 2.77 | 44.5 | 11.5 |
| | SD | 201 | | 60.5 | 0.224 | 0.511 | 4.55 | 2.81 |
| | CV (%) | 19.7 | | 16.2 | 16.6 | 18.5 | 10.2 | 24.4 |
| Dose 2 | Arith. Mean | 1319 | | 448 | 1.30 | 3.60 | 36.6 | 7.56 |
| | SD | 281 | | 98.6 | 0.447 | 0.94 | 4.12 | 2.98 |
| | CV (%) | 21.3 | | 22.0 | 34.4 | 26.0 | 11.3 | 39.3 |
| Dose 3 | Arith. Mean | 1413 | | 490 | 0.900 | 3.74 | 39.2 | 7.72 |
| | SD | 347 | | 127 | 0.137 | 0.945 | 6.67 | 2.54 |
| | CV (%) | 24.6 | | 26.0 | 15.2 | 25.2 | 17.0 | 32.9 |
| Dose 4 | Arith. Mean | 1456 | | 509 | 1.10 | 4.17 | 42.0 | 7.03 |
| | SD | 285 | | 101 | 0.652 | 0.611 | 6.01 | 1.02 |
| | CV (%) | 19.6 | | 19.9 | 59.3 | 14.6 | 14.3 | 14.5 |
| Dose 1-4 | Arith. Mean | AUC0-24 | 6567 | | | | | |
| | SD | | 1569 | | | | | |
| | CV (%) | | 23.9 | | | | | |
| | | Mean PK Parameters Day 3 Phenotype: Slow Acetylators | | | | | | |
| Dose 1 | Arith. Mean | 523 | | 206 | 1.75 | 3.47 | 95.0 | 19.0 |
| | SD | 65.9 | | 67.1 | 0.901 | 0.437 | 11.4 | 0.118 |
| | CV (%) | 12.6 | | 32.5 | 51.5 | 12.6 | 12.0 | 0.620 |

TABLE 11-continued

Mean PK Parameter Summary for 3-N-Acetyl Metabolite in Fast and Slow Acetylators on Day 3 of Multiple Dosing (20 mg, QID)

| Dose Int. | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Dose 2 | Arith. Mean | 684 | | 222 | 1.50 | 3.89 | 81.5 | 14.5 |
| | SD | 81.6 | | 29.0 | 0.500 | 0.055 | 2.60 | 0.672 |
| | CV (%) | 11.9 | | 13.1 | 33.3 | 1.43 | 3.19 | 4.62 |
| Dose 3 | Arith. Mean | 802 | | 249 | 1.20 | 3.75 | 68.1 | 12.7 |
| | SD | 187 | | 59.8 | 0.274 | 0.672 | 14.7 | 2.75 |
| | CV (%) | 23.4 | | 24.0 | 22.8 | 17.9 | 21.7 | 21.6 |
| Dose 4 | Arith. Mean | 814 | | 258 | 0.900 | 5.70 | 78.3 | 9.65 |
| | SD | 134 | | 25.0 | 0.224 | 0.643 | 13.7 | 2.15 |
| | CV (%) | 16.5 | | 9.72 | 24.8 | 11.3 | 17.5 | 22.3 |
| Dose 1-4 | Arith. Mean | | 3649 | | | | | |
| | SD | | 654 | | | | | |
| | CV (%) | | 17.9 | | | | | |

TABLE 12

Mean PK Parameter Summary for 3-N-Acetyl Metabolite Fast and Slow Acetylators on Day 4 of Multiple Dosing (20 mg, Single Dose)
Mean PK Parameters Day 4, Single Dose

| | | $AUC_{0-4}$ (ng · h/mL) | $AUC_{0-24}$ (ng · h/mL) | $C_{max}$ (ng/mL) | $T_{max}$ (hr) | $t_{1/2}$ (hr) | Vz/F (L) | CL/F (L/hr) |
|---|---|---|---|---|---|---|---|---|
| Fast | Arith. Mean | 1028 | 2125 | 2206 | 363 | 1.40 | 4.95 | 69.4 |
| | SD | 213.7 | 756 | 835 | 53.4 | 0.379 | 0.988 | 20.2 |
| | CV (%) | 20.8 | 35.6 | 37.8 | 14.7 | 27.1 | 20.0 | 29.2 |
| Slow | Arith. Mean | 513 | 1229 | 1278 | 178 | 1.55 | 4.99 | 116 |
| | SD | 74.4 | 249 | 265 | 34.7 | 0.512 | 0.642 | 22.4 |
| | CV (%) | 14.5 | 20.3 | 20.7 | 19.5 | 33.1 | 12.9 | 19.4 |

The differences in PK parameters for exposure between the fast and slow acetylator groups at all single and multiple dose levels indicate Firdapse PK parameters are significantly influenced by NAT phenotype and that metabolic clearance of Firdapse by N-acetylation significantly impacts the plasma pharmacokinetic profile of orally administered Firdapse® tablets.

Safety Results

There were no serious adverse events. There were no clinically significant changes in the subjects' ECG and there were no other clinically significant changes observed in other clinical laboratory assessments. No subject discontinued due to any adverse event. All treatment-emergent adverse events were mild and transient and resolved without sequela.

Part 1:

Treatment-emergent drug-related adverse events by treatment and phenotype are given in FIG. 28. All adverse events were observed in slow acetylators only, even at the higher doses of 20 mg (Day 3) and 30 mg (Days 4-7).

Part 2:

Treatment-emergent drug-related adverse events by treatment and phenotype are given in FIG. 29. Adverse events were observed in both acetylator types. Forty-five drug-related adverse events were reported by 6 (86%) of 7 slow acetylators. In contrast, six drug-related adverse events were reported in 3 (43%) of 7 fast acetylators.

Example 19

Clinical Trial to Evaluate Efficacy, Safety, and Relationship Between NAT Genetic Polymorphism Status and Plasma Levels of Amifampridine and 3-N-Acetyl Amifampridine in LEMS Patients Efficacy:

In this study efficacy of amifampridine phosphate versus placebo on muscle strength in patients with LEMS at the end of a 14-day discontinuation period is to be evaluated. In addition, efficacy can be determined by determining walking speed in patients with LEMS at the end of a 14-day discontinuation period. The following parameters in patients with LEMS at the end of a 14-day discontinuation period can also be determined in evaluating efficacy: CMAP: amplitude, CGI-S: Investigator-perceived improvement in illness severity, CGI-I: Investigator-perceived global improvement or change, and SGI: Subject global impression of improvement. Finally, this study is designed to 1) confirm the exposure of amifampridine and its major metabolite, 3-N-acetyl amifampridine, based on plasma concentrations in the LEMS patient population; 2) to evaluate the relationship between NAT genetic polymorphism status and plasma levels of amifampridine and 3-N-acetyl amifampridine in LEMS patients.

Safety:

The safety objective of the study is to assess the safety, including the long-term safety, of amifampridine phosphate in patients with LEMS.

Study Design

This double-blind, placebo-controlled, randomized (1:1) discontinuation study is a 4-part study designed to evaluate the efficacy and safety of multiple dose administration of amifampridine phosphate in patients with LEMS. The long-term clinical efficacy of amifampridine phosphate is evaluated in patients with at least 91 days of previous amifampridine treatment by comparing changes (as determined by QMG) that occur in patients who discontinue treatment versus patients who continue on active treatment to the end of a 14-day double-blind efficacy evaluation period.

In addition to amifampridine, patients will continue to receive best supportive care (BSC) treatment as determined by the investigator using concomitant medications permitted per the protocol, which include the following: 1) selected oral immunosuppressants (e.g., prednisone or other corticosteroids, azathioprine, mycophenolate) and 2) peripherally acting cholinesterase inhibitors (e.g., pyridostigmine). No BSC changes should be made during Screening, Part 1 (Open-label Run-in), Part 2 (Double-blind Treatment Discontinuation), and Part 3 (Double-blind Treatment). However, modifications is allowed in Part 4 (Open-label Extension). If changes are made to BSC during Screening or Part 1, entry of the patient into Part 2 may be delayed to allow stabilization of the new regimen.

An analysis for both efficacy and safety is performed after all patients complete Part 3, Double-blind Treatment. A final safety analysis is performed at the end of the study, completion of Part 4, Open-label Extension.

Screening and Enrollment

After providing informed consent, patients undergo a Screening evaluation to determine study eligibility. Efficacy assessments is performed for all patients during Screening. For patients receiving amifampridine treatment prior to enrollment, efficacy assessments is performed at standardized times relative to the first dosing time of the day (see the standardized schedule of efficacy assessments below). For patients not receiving amifampridine treatment at the time of Screening, efficacy assessments should be completed on the same standardized schedule starting at a time consistent with anticipated future first dosing time of the day. Safety assessments are also be conducted during Screening.

Part 1: Open-Label Run-in

The purpose of the Open-label Run-in is to 1) allow the investigator to titrate amifampridine phosphate to the optimal dose regimen for each individual patient, and 2) to allow patients to achieve duration of amifampridine exposure required prior to randomized discontinuation.

All patients will start taking amifampridine phosphate on Day 1 of the Open-label Run-in. The dose of amifampridine is individually determined, for example, by the investigator, within the bounds of a 30-80 mg total daily dose and a maximum of 20 mg at any single administration. Patients with moderate renal impairment will start at a total dose of 10 mg per day.

Investigational Product(s), Dose, Route, and Regimen.

The final amifampridine phosphate dose regimen during Open-Label Run-in is determined by the investigator for each individual patient, based on the optimal observed neuromuscular benefit. Patients who do not achieve optimal neuromuscular benefit during this time period will be discontinued from treatment and withdrawn from the study following safety follow-up.

Patients are required to have a minimum of 91 days (13 consecutive weeks) of amifampridine, base or phosphate, treatment prior to randomization into Part 2, Double-blind Treatment Discontinuation. The 91 consecutive days may include time receiving amifampridine prior to Screening, during Screening, and during Run-in. Patients are also required to have a stable amifampridine phosphate dose regimen (i.e., the same total daily dose and dose regimen) for at least the 7 days immediately prior to entering Part 2. If at least 1 day with more than 50% of doses is missed during the 7 days immediately prior to entering Part 2, the 7 day run-in period must be restarted. If a patient requires more than 2 restarts, the investigator should contact the Medical Monitor to discuss.

Patients should remain on the same BSC therapy throughout the Run-in period. If a change in concomitant immunotherapy is made, the required 91 days of consecutive treatment is restarted at that point. If a change in peripheral cholinesterase inhibitor is made during the 7 days of a stable amifampridine phosphate regimen, then that 7-day period is restarted at that point. Thus changes in BSC can delay patient entry into Part 2.

Optional blood samples for NAT genetic testing will be collected on Day 1 of the Open-Label Run-in. Safety assessments will be performed bi-weekly per the schedule of assessments and as necessary. Electrocardiogram (ECG) will be performed on Day 1 and then monthly per the schedule of assessments.

Patients should begin Part 2 (Double-blind Treatment Discontinuation. Randomization) as soon as possible after meeting all of the Open-label Run-in requirements described above: 1) optimal neuromuscular benefit on amifampridine phosphate treatment; 2) at least 91 consecutive days of amifampridine treatment (base or phosphate); 3) at least 7 consecutive days of stable open-label amifampridine phosphate dosing (i.e., the same total daily dose and dose regimen) immediately prior to entering Part 2; and 4) required duration of a stable BSC regimen.

Part 2: Double-Blind Treatment Discontinuation

On Day 1 of Part 2, patients are randomized (1:1) using a centralized randomization method (interactive voice/web response system, IXRS) to one of the following blinded treatments:

Continuation of Treatment (treatment group A): Amifampridine phosphate (at a dose established during Open-label Run-in) for 7 days.

Discontinuation of Treatment (treatment group B): This involves downward titration of amifampridine phosphate dose to 0 mg. This will be accomplished by substituting an increasing proportion of matching placebo tablets for amifampridine phosphate tablets starting on Day 2 and ending on Day 7, at which point all tablets are placebo.

Blood samples are collected for pharmacokinetic analysis on Day 1 of Part 2 prior to dosing, and at 2.0 and 4.0 hours (both ±15 min) after dosing. Blood samples for PK are collected on Day 2 of Part 2 prior to dosing, at 15, 30 and 90 min (all ±5 min) post-dosing, and at 2.0 and 4.0 hours (both ±15 min) post dosing. Urine samples collected on Day 1 are assayed for 3-N-acetyl amifampridine metabolite. Also on Day 2 of Part 2, ECGs are obtained in triplicate prior to dosing and at 1.0 and 2.0 hours (±15 min) after dosing.

Standardized Schedule of Efficacy Assessments

Baseline efficacy assessments is performed on Day 1. The first dose must be taken at the same time each day of Part 2 (±15 min) and administered in the clinic on days that efficacy assessments are performed. The required schedule of efficacy assessments is listed in the table below.

| Assessment | Start Time After Dose (±15 min unless otherwise specified) |
|---|---|
| CMAP amplitude | 00:45 (−5/+15 min) |
| QMG | 01:15 |
| T25FW | 02:15 |
| CGI-S, CGI-I, SGI | In this order following prior assessments |

To prevent unblinding, the same individual rater may not perform both the CMAP and QMG tests on an individual patient.

Part 3: Double-Blind Treatment

Patients who are randomized to amifampridine phosphate in Part 2 will continue to receive the same dose regimen for 7 additional days. Patients who are downward titrated to placebo in Part 2 will remain on placebo for 7 days.

Efficacy and safety assessments are performed on Day 8 and Day 14 following the standardized schedule. Urine samples collected on Days 8 and 14 are assayed for 3-N-acetyl amifampridine metabolite to verify compliance with the prohibition against the use of other sources of amifampridine during the Double-blind Treatment period.

Rescue Treatment

In Parts 2 and 3 of the study, it is recognized that some patients may experience severe signs and symptoms of their disease upon downward titration and cessation of amifampridine phosphate. Therefore, rescue treatment will be provided to patients who experience treatment failure as defined by meeting at least 1 of the following criteria:

Becomes non-ambulatory (after having been ambulatory at Screening) as defined as a patient who was previously able to walk but who becomes unable to walk even with the use of assistive devices (e.g., cane or walker) and requires a wheelchair for mobility.

Demonstrates an increase (worsening) in QMG score by >5 points.

Develops respiratory failure as defined as the need for mechanical ventilation.

Unless the clinical condition of the patient is so severe as to dictate otherwise, patients who meet rescue treatment criteria will be discontinued from Part 2 or 3 and will proceed to Rescue Visit 1. Rescue Visit 1 should be performed as soon as a patient is identified as potentially requiring open-label amifampridine phosphate rescue treatment. If possible, a confirmatory Rescue Visit 2 should be performed approximately 8 to 24 hours following Rescue Visit 1. If possible, efficacy and safety assessments will be performed and a venous blood sample for the determination of plasma amifampridine concentration will be obtained at each rescue visit. During the interval between Rescue Visits, patients will receive standard of care as deemed appropriate by the investigator.

After completion of the assessments/procedures for Rescue Visit 2, rescue treatment may be initiated. Rescue treatment may include open-label amifampridine phosphate at a dose level determined by the investigator. Other treatments for LEMS may also be administered as judged clinically appropriate by the investigator; however, immunosuppressives that lower the seizure threshold (e.g., cyclosporine, tacrolimus) or other aminopyridines are not permitted in combination with amifampridine phosphate. The patient will be provided the option to receive open-label amifampridine phosphate in Part 4, Open-label Extension.

Part 4: Open-Label Extension

The following patients will be offered the option to participate in Part 40-pen-label Extension: 1) patients who complete Parts 1, 2, and 3; 2) patients who received per protocol rescue treatment with amifampridine phosphate; or 3) patients who are participating in Part 1 but who have not established 7 days of stable amifampridine phosphate dosing when the 30th patient is randomized in Part 2.

Amifampridine phosphate dosing is started on Day 15. Patients are seen on Day 19 (±2 days) and monthly for the next 2 visits and then quarterly thereafter. Safety assessments are performed at each visit. Patients receive their individualized dose of open-label amifampridine phosphate based on investigator assessment. Investigators determine whether or not to follow dose initiation and titration as in Part 10-pen-label Run-in. Changes to BSC may be made at the investigator's discretion, as long as prohibited medications are not used. Each patient's study participation may continue until the study is terminated (2 years after the last patient is enrolled into Part 4). If amifampridine phosphate is or becomes commercially available while the patient is enrolled in Parts 1-3 of the study, they may only participate in Part 4 for a maximum of 1 year.

Diagnosis and all Criteria for Inclusion and Exclusion:

Individuals eligible to participate in this study must have a confirmed diagnosis of LEMS as documented by acquired (typical) proximal muscle weakness and at least 1 of nerve conduction findings (CMAP that increases at least 2-fold after maximum voluntary contraction of the tested muscle) and positive anti-P/Q type voltage-gated calcium-channel antibody test; have completed an anti-cancer treatment at least 3 months (90 days) prior to Screening; have a QMG score of ≥5 is required for patients without any prior symptomatic treatment for LEMS; present with some signs and/or symptoms consistent with LEMS if currently receiving treatment for LEMS; have normal respiratory function as defined by a forced vital capacity>80% predicted (score of 0 on this dimension of QMG); and have normal swallowing function as defined by the ability to swallow 4 ounces of water without coughing or throat clearing (score of 0 on this dimension of QMG).

Individuals who meet any of the following exclusion criteria are not eligible to participate in the study: history of epilepsy or seizure (including single 1-time seizure, but excluding generalized febrile seizures occurring before the age of 5 years); known active brain metastasis; use of 4-aminopyridine and any form of 3,4-diaminopyridine; use of medications known to lower the epileptic threshold within the longer of 7 days or 5 half-lives prior to Screening; use of selected antidepressants of the selective serotonin uptake inhibitor (SSRI) class; use of medications which inhibit neuromuscular junction function within the longer of 7 days or 5 half-lives prior to Screening; use of guanidine hydrochloride within 7 days of Screening; use of rituximab within 12 months prior to Screening; treatment with a concomitant medication that prolongs the QT/QTc interval within the longer of 7 days or 5 half-lives prior to Screening; treatment with sultopride (4-amino-N-[(1-ethylpyrrolidin-2-yl) methyl]-5-ethylsulfonyl-2-methoxybenzamide) within 7 days prior to Screening; an electrocardiogram (ECG) at Screening that, in the opinion of the external reviewing cardiologist, shows any of sinus arrhythmia with unacceptable rate variation, excessive heart rate variation at rest, QTcB interval>450 msec, PR interval>210 msec, QRS interval>120 msec if 35 years of age or younger, or >110 msec if over age 35 years, or early repolarization pattern that increases the risk of participating in the study; history of arrhythmias, risk factors for torsade de pointes, or severe renal impairment or evidence of severe renal impairment on Screening laboratory tests; likely or expected to require treatment for cancer within 3 months (90 days) after entering Screening; ALT, AST, and/or total bilirubin>ULN for patients without liver metastases; or ALT/AST>5× upper limit of normal (ULN) and/or total bilirubin>3×ULN in patients with liver metastases from cancer.

Investigational Product(s), Dose, Route, and Regimen:

IP is provided in 250 mg tablets, containing the equivalent of 10 mg amifampridine base per tablet.

During Parts 1 and 4 (open-label), patients receive a total daily dose of amifampridine phosphate 30 to 80 mg per day given 3 to 4 times per day, with a maximum single dose of 20 mg; with the exception of patients with moderate renal impairment, who will start at a total daily dose of 10 mg. Amifampridine phosphate is to be taken with food. In Part 1, determination of initial dose level are as follows:

In patients already taking amifampridine base, amifampridine phosphate should be started at an equivalent or lower dose of amifampridine phosphate, at the investigator's discretion.

In patients not currently taking amifampridine, amifampridine phosphate should be initiated at a low dose (10 mg, 3 to 4 times per day).

In patients with moderate renal impairment who are not taking amifampridine phosphate prior to the study, the starting total daily dose will be 10 mg. Moderate renal impairment is defined as a creatinine clearance of 30 to 59 mL/min where creatinine clearance is calculated using the Cockcroft-Gault equation as [(140−Age)*Mass (in kg)]/[72*serum creatinine (in mg/dL)] (Note: If the patient is a female, multiply the output of the equation by 0.85.) Note, a brief deviation from the usual requirement that the total daily dose fall in the 30-80 mg/day range is allowed during initial titration in patients with moderate renal impairment.

The titration schedule is an increase by 10 mg increments every 4 to 5 days to a maximum of 80 mg per day based on optimal neuromuscular benefit and at the discretion of the investigator.

During Part 2 (Double-blind Treatment Discontinuation), patients randomized to treatment Group A continue for 7 days on the amifampridine phosphate dose established during the Open-label Run-in phase. Patients randomized to treatment Group B have their amifampridine phosphate dose downward titrated to 0 mg. This is accomplished by substituting an increasing proportion of matching placebo tablets for amifampridine phosphate tablets starting on Day 2 and ending on Day 7, at which point all tablets are placebo. Patients in treatment Group B continue to take the same number of tablets daily throughout this period.

During Part 3 (Double-blind Treatment), patients who are randomized to amifampridine phosphate in Part 2 Group A continue to receive the same dose regimen for 7 additional days. Patients who are downward titrated to placebo in Part 2 Group B remain on placebo for 7 days.

During Part 4 (Open-label Extension) patients receive their individualized dose of open-label amifampridine phosphate based on investigator assessment at 30 to 80 mg per day given 3 to 4 times per day, up to a maximum of 20 mg in a single dose.

Reference Therapy, Dose, Route, and Regimen:

The reference therapy during the Double-blind Treatment Discontinuation and Double-blind Treatment period is a placebo, provided as tablets indistinguishable from amifampridine phosphate tablets. The placebo will be administered consistent with the dose and dose regimen of the investigational product (amifampridine phosphate).

No reference therapy is to be administered in Part 1 0-pen-label Run-in or in Part 4 Open-label Extension.

Duration of Treatment:

Part 1: 7-91 days (Open-label Run-in); Part 2: 7 days (Double-blind Treatment Discontinuation); Part 3: 7 days (Double-blind Treatment); Part 4: Open-label Extension To maintain the completeness and integrity of the data, patients who discontinue from treatment early should continue to have study assessments performed until completion of the Double-blind Treatment phase as long as in the judgment of the investigator such continued participation would not detrimentally affect the health, safety, or welfare of the patient.

Criteria for Evaluation:

All efficacy evaluations is obtained during the Double-Blind phase of the study (to Day 14).

Efficacy:

Efficacy endpoints that could be evaluated include one or more of the following the change from baseline to Day 14 in QMG score, the change from baseline to Day 14 in walking speed assessed by the T25FW test, change from baseline to Day 14 in CMAP amplitude, the Day 14 CGI-I and SGI scale measurements, the proportion of patients in each treatment group with a Day 14 CGI-I scale rating of 1, 2, 3, or 4, the proportion of patients in each treatment group with a Day 14 SGI scale rating of 4, 5, 6, or 7, and The change from baseline to Day 14 in CGI-S scale measurements.

PK of amifampridine and 3-N-acetyl metabolite in plasma will be conducted in the LEMS patient population. The relationship between NAT genetic status and exposure to amifampridine and 3-N-acetyl metabolite will be evaluated and described.

Safety:

Safety will be assessed by the incidence of AEs, including SAEs. Safety will also be assessed by changes from baseline in the following: Abnormal and clinically significant laboratory tests, vital signs, physical examination, concomitant medications, and ECG.

Statistical Methods:

An analysis for both efficacy and safety is performed after all patients complete Part 3, Double-blind Treatment. A final safety analysis is performed at the end of study, completion of Part 4, Open-label Extension.

Sample Size Determination

A total of 30 patients are provided 80% power to detect a 3.0 unit difference in the mean change of the QMG scores between the 2 treatment groups, assuming a type I error of 0.05 and a common standard deviation of 2.7.

Efficacy Analysis

Efficacy analysis is conducted on all patients randomized into the study. All endpoints are summarized using descriptive statistics at each measurement time point, including for Part 1 of the study. Treatment differences will be assessed at a significance level of 0.05 for all endpoints. Baseline is defined as the measurements obtained at the beginning of Part 2 Double-blind Treatment Discontinuation (Day 1).

The change in QMG scores from baseline (Day 1, Part 2) to Day 14 (Part 3) is compared between treatment groups using an analysis of covariance (ANCOVA) where the covariate adjusted for will be baseline QMG. If significant departures from normality are observed, then the Wilcoxon Rank Sum test comparing the treatment groups will be performed on the QMG change from baseline scores. Alternatively a Rank ANCOVA analysis may be performed.

Change in the T25FW test walking speed from baseline to Day 14 is compared between treatment groups, using the same analysis method which is used for the primary efficacy endpoint.

Change in CMAP amplitude, as well as other continuous efficacy endpoints, is analyzed in a manner similar to the analysis performed for the QMG scores and walk test. All categorical endpoints will be analyzed using contingency table approach and the comparisons between the 2 treatment groups will be performed using Fisher's Exact Test. Due to the exploratory nature of the analysis, no adjustments for multiple testing will be done.

Pharmacokinetic and Genetic Analysis

Data from all patients who have PK blood samples taken are included in the PK analysis to determine amifampridine and N-acetyl metabolite exposure levels at key time points post dosing. Sparse or limited exposure data from this study may be analyzed in combination with available full PK data (and PK models derived thereof) from other clinical studies to derive exposure parameters for the LEMS patient population. Amifampridine and 3-N-acetyl amifampridine exposure with NAT genotype status, along with descriptive statistics, will be evaluated.

Safety Analysis

All patients who receive at least 1 dose of IP or placebo, and have any post-treatment safety information collected are included in the safety analysis. The safety analysis will be descriptive and will be performed separately for each part of the study. All AEs are coded using the Medical Dictionary for Regulatory Activities (MedDRA). Only treatment-emergent AEs (TEAEs) will be included in the safety analysis. The incidence of AEs will be summarized by system organ class, preferred term, relationship to treatment, and severity for each treatment group. All AEs, as well as AEs leading to premature discontinuation and serious AEs (SAEs), will be listed. All other safety measures including laboratory tests, vital signs, ECGs, and concomitant medications data will also be summarized descriptively.

Handling of Dropouts and Missing Values:

Missing efficacy values for the primary and secondary endpoints will be imputed. Imputation methods for missing data will be described in the Statistical Analysis Plan.

Because the completeness of the data affects the integrity and accuracy of the final study analysis, every effort will be made to ensure complete, accurate, and timely data collection and, therefore, avoid missing data. Patients who discontinue from IP treatment early should continue to have study assessments performed until completion of Part 3, Double-blind Treatment, as long as in the judgment of the investigator such continued participation would not detrimentally affect the health, safety, or welfare of the patient.

All patents, publications and references cited herein are hereby fully incorporated by reference. In case of conflict between the present disclosure and incorporated patents, publications and references, the present disclosure will control.

What is claimed is:

1. A method of treating a human patient diagnosed with a 3,4-diaminopyridine (3,4-DAP) sensitive disease in need of treatment thereof comprising administering a dose of about 2.5 mg to about 30 mg of 3,4-DAP or a pharmaceutically acceptable salt thereof to a human patient who is a slow acetylator having an N-acetyl transferase 2 (NAT2) gene comprising: a C282T mutation on both alleles of the NAT2 gene; a T341C mutation on both alleles of the NAT2 gene; or a C282T mutation on one allele of the NAT2 gene and a T341C mutation on the other allele of the NAT2 gene.

2. The method of claim 1, wherein the 3,4-DAP-sensitive disease is Lambert-Eaton myasthenic syndrome (LEMS), myasthenia gravis, or congenital myasthenia.

3. The method of claim 1, wherein the patient has a maximum plasma concentration of about 90 ng/mL of 3,4-DAP following administration of the dose.

4. The method of claim 1, wherein the patient has a maximum plasma concentration of about 15 ng/mL to about 40 ng/mL of 3,4-DAP following administration of the dose.

5. The method of claim 1, wherein the pharmaceutically acceptable salt is a phosphate salt.

6. The method of claim 1, wherein the dose administered is a total daily dose.

7. The method of claim 6, wherein the total daily dose is orally administered in one, two, three, four, or five single doses per day.

8. The method of claim 7, wherein the single dose is provided as one or more scored tablets or portions thereof.

9. The method of claim 8, wherein the scored tablet comprises about 10 mg of 3,4-DAP or a pharmaceutically acceptable salt thereof.

10. The method of claim 7, wherein each single dose comprises about 5 mg to about 30 mg of 3,4-DAP or a pharmaceutically acceptable salt thereof.

11. The method of claim 6, wherein the total daily dose is about 15 mg to about 30 mg of 3,4-DAP or a pharmaceutically acceptable salt thereof.

12. The method of claim 11, wherein the total daily dose is orally administered in 3 or 4 single doses per day.

13. The method of claim 11, wherein the total daily dose is about 15 mg of 3,4-DAP or a pharmaceutically acceptable salt thereof orally administered in 3 single doses per day.

14. The method of claim 11, wherein the total daily dose is about 30 mg of 3,4-DAP or a pharmaceutically acceptable salt thereof orally administered in 3 single doses per day.

15. The method of claim 6, wherein the total daily dose is about 7.5 mg to about 15 mg of 3,4-DAP or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 10,793,893 B2 |
| APPLICATION NO. | : 14/128672 |
| DATED | : October 6, 2020 |
| INVENTOR(S) | : Garovoy et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this
Fifteenth Day of November, 2022

Katherine Kelly Vidal
*Director of the United States Patent and Trademark Office*